United States Patent
Sommer et al.

(10) Patent No.: US 12,036,312 B2
(45) Date of Patent: Jul. 16, 2024

(54) NON-AQUEOUS TOPICAL COMPOSITIONS COMPRISING A HALOGENATED SALICYLANILIDE

(71) Applicants: UNION therapeutics A/S, Hellerup (DK); UNIVERSITY OF COPENHAGEN, København K (DK)

(72) Inventors: Morten Otto Alexander Sommer, Hellerup (DK); Ping Li, Dyssegård (DK); Camilla Hasling Frandsen, Copenhagen N (DK); Hanne Mørck Nielsen, Hillerød (DK); Petra Alexandra Priemel, Dyssegård (DK); Thomas Rades, Copenhagen (DK)

(73) Assignees: UNION THERAPEUTICS A/S, Hellerup (DK); KØBENHAVNS UNIVERSITET (UNIVERSITY OF COPENHAGEN), Copenhagen (DK)

( * ) Notice: Subject to any disclaimer, the term of this patent is extended or adjusted under 35 U.S.C. 154(b) by 0 days.

(21) Appl. No.: 16/084,741

(22) PCT Filed: Mar. 15, 2017

(86) PCT No.: PCT/EP2017/056083
§ 371 (c)(1),
(2) Date: Sep. 13, 2018

(87) PCT Pub. No.: WO2017/157997
PCT Pub. Date: Sep. 21, 2017

(65) Prior Publication Data
US 2019/0151231 A1 May 23, 2019

(30) Foreign Application Priority Data

Mar. 16, 2016 (GB) .................................... 1604484

(51) Int. Cl.
| | | |
|---|---|---|
| *A61K 31/277* | (2006.01) | |
| *A61K 9/00* | (2006.01) | |
| *A61K 9/06* | (2006.01) | |
| *A61K 31/167* | (2006.01) | |
| *A61K 31/203* | (2006.01) | |
| *A61K 31/327* | (2006.01) | |
| *A61K 31/609* | (2006.01) | |
| *A61K 45/06* | (2006.01) | |
| *A61K 47/10* | (2017.01) | |
| *A61K 47/32* | (2006.01) | |
| *A61K 47/38* | (2006.01) | |
| *A61P 17/10* | (2006.01) | |
| *A61P 31/04* | (2006.01) | |

(52) U.S. Cl.
CPC .............. *A61K 9/0014* (2013.01); *A61K 9/06* (2013.01); *A61K 31/167* (2013.01); *A61K 31/203* (2013.01); *A61K 31/327* (2013.01); *A61K 31/609* (2013.01); *A61K 45/06* (2013.01); *A61K 47/10* (2013.01); *A61K 47/32* (2013.01); *A61K 47/38* (2013.01); *A61P 17/10* (2018.01); *A61P 31/04* (2018.01)

(58) Field of Classification Search
None
See application file for complete search history.

(56) References Cited

U.S. PATENT DOCUMENTS

| | | |
|---|---|---|
| 2,731,386 A | 1/1956 | Reiner |
| 3,152,039 A | 10/1964 | Mattson |
| 3,674,850 A | 7/1972 | Osborne |
| 3,914,418 A | 10/1975 | Patchett et al. |
| 4,671,957 A | 6/1987 | Holtshousen et al. |
| 4,883,660 A | 11/1989 | Blackman et al. |
| 5,719,197 A | 2/1998 | Kanios et al. |
| 6,251,869 B1 | 6/2001 | Bohanon |
| 6,399,629 B1 | 6/2002 | Chamberland et al. |
| 8,198,326 B2 | 6/2012 | Scholz et al. |
| 8,846,646 B2 | 9/2014 | Chiou |
| 9,949,988 B2 | 4/2018 | Delavenne et al. |
| 10,463,680 B2 | 11/2019 | Sommer et al. |
| 10,758,553 B2 | 9/2020 | Delavenne et al. |
| 10,857,164 B2 | 12/2020 | Sommer et al. |
| 11,045,434 B1 | 6/2021 | Sommer et al. |
| 11,285,164 B2 | 3/2022 | Delavenne et al. |
| 11,324,708 B1 | 5/2022 | Sommer et al. |
| 11,331,237 B2 | 5/2022 | Smith |

(Continued)

FOREIGN PATENT DOCUMENTS

| | | |
|---|---|---|
| CN | 104053632 A | 9/2014 |
| DE | 19859426 A1 | 7/2000 |

(Continued)

OTHER PUBLICATIONS

United Kingdom Intellectual Property Office, Search Report for GB1604484.4, Dec. 16, 2016, 5 pages.
Unknown Author, OECD guideline for testing of chemicals, Jul. 28, 2015, 8 pages.
European Patent Office, International Search Report and Written Opinion for PCT International Patent Application No. PCT/EP2017/056083, May 4, 2017, 13 pages.
Thiboutot, et al., New insights in to the management of acne: An update from the Global Alliance to Improve Outcomes in Acne Group, J. Am. Acad. Dermatol., 2009, pp. S1-S50, vol. 60.

(Continued)

*Primary Examiner* — Layla Soroush
(74) *Attorney, Agent, or Firm* — Mintz, Levin, Cohn, Ferris, Glovsky and Popeo, P.C.

(57) ABSTRACT

The present invention relates to non-aqueous topical compositions comprising a halogenated salicylanilide and the use of such compositions in the topical treatment or prevention of diseases and infections, particularly conditions caused by Gram-positive bacteria, for example the topical treatment or prevention of skin infections such as acne, atopic dermatitis and impetigo. Also disclosed are methods for preparing the gel composition.

30 Claims, 8 Drawing Sheets

(56) References Cited

U.S. PATENT DOCUMENTS

| | | |
|---|---|---|
| 11,419,834 B2 | 8/2022 | Mylonakis et al. |
| 11,529,361 B2 | 12/2022 | Sommer et al. |
| 2006/0052452 A1 | 3/2006 | Scholz |
| 2006/0280783 A1 | 12/2006 | Dipietro et al. |
| 2009/0011007 A1 | 1/2009 | Meier et al. |
| 2009/0016990 A1 | 1/2009 | Alberte et al. |
| 2009/0098069 A1 | 4/2009 | Vacca |
| 2010/0016442 A1 | 1/2010 | Cohen et al. |
| 2010/0029781 A1 | 2/2010 | Morris |
| 2010/0317643 A1 | 12/2010 | Goodacre et al. |
| 2011/0028460 A1 | 2/2011 | Kisak et al. |
| 2013/0005802 A1* | 1/2013 | Chen .................. A61K 31/00 514/521 |
| 2014/0018323 A1 | 1/2014 | Friedman et al. |
| 2014/0294957 A1 | 10/2014 | Stein et al. |
| 2016/0008471 A1 | 1/2016 | Batt et al. |
| 2017/0014325 A1 | 1/2017 | Carola et al. |
| 2017/0056347 A1 | 3/2017 | Glick et al. |
| 2017/0172943 A1 | 6/2017 | Hardas et al. |
| 2017/0258816 A1 | 9/2017 | Delavenne et al. |
| 2017/0304372 A1 | 10/2017 | Kim et al. |
| 2018/0207179 A1 | 7/2018 | Sommer et al. |
| 2018/0224470 A1 | 8/2018 | Leung et al. |
| 2019/0201422 A1 | 7/2019 | Sommer et al. |
| 2020/0268693 A1 | 8/2020 | Mylonakis et al. |
| 2020/0306269 A1 | 10/2020 | Delavenne et al. |
| 2020/0306270 A1 | 10/2020 | Delavenne et al. |
| 2020/0306271 A1 | 10/2020 | Delavenne et al. |
| 2021/0137948 A1 | 5/2021 | Sommer |
| 2021/0308153 A1 | 10/2021 | Sommer et al. |
| 2021/0369650 A1 | 12/2021 | Guttman-Yassky et al. |
| 2022/0323384 A1 | 10/2022 | Sommer et al. |
| 2023/0147683 A1 | 5/2023 | Sommer et al. |
| 2023/0190685 A1 | 6/2023 | Sommer et al. |

FOREIGN PATENT DOCUMENTS

| | | | |
|---|---|---|---|
| EP | 0487973 | | 11/1991 |
| EP | 0487973 | | 3/1996 |
| EP | 0487973 B1 * | 3/1996 | ........... A61K 9/0014 |
| EP | 1674068 A1 | | 6/2006 |
| EP | 2219603 A1 | | 8/2010 |
| FR | 1340175 A1 | | 10/1963 |
| GB | 1421589 A | | 1/1976 |
| GB | 1527638 | | 10/1978 |
| GB | 2456376 | | 1/2009 |
| GB | 2465633 A * | 6/2010 | .............. A61P 17/10 |
| JP | 2004-331577 A | | 11/2004 |
| JP | 2007007189 A | | 1/2007 |
| JP | 2009-519709 A | | 5/2009 |
| JP | 2009533415 A | | 9/2009 |
| JP | 2010-528098 A | | 8/2010 |
| JP | 2011-511774 A | | 4/2011 |
| JP | 2011526934 A | | 10/2011 |
| JP | 2012012338 | | 1/2012 |
| JP | 20120505867 | | 10/2012 |
| JP | 2013-529668 A | | 7/2013 |
| JP | 2013224320 A | | 10/2013 |
| RU | 2227025 C2 | | 4/2004 |
| SU | 597671 | | 3/1978 |
| WO | 9619220 A1 | | 6/1996 |
| WO | WO-1996/40086 A2 | | 12/1996 |
| WO | WO-1998/056390 | | 5/1998 |
| WO | 9965449 A2 | | 12/1999 |
| WO | WO-2000/025822 A1 | | 5/2000 |
| WO | WO-01/60157 | | 8/2001 |
| WO | WO-2002-45662 | | 6/2002 |
| WO | WO-2003/072113 A1 | | 9/2003 |
| WO | 03/103665 A1 | | 12/2003 |
| WO | WO-2004/006906 | | 1/2004 |
| WO | WO-2005/007129 A2 | | 1/2005 |
| WO | WO-2005/025598 | | 3/2005 |
| WO | WO-2005/074912 A2 | | 8/2005 |
| WO | WO-2005/074912 A3 | | 8/2005 |
| WO | WO-2006/104763 A1 | | 10/2006 |
| WO | WO-2007/066130 A2 | | 6/2007 |
| WO | WO-2007-066130 A3 | | 6/2007 |
| WO | 2007119151 A1 | | 10/2007 |
| WO | 2008006848 A1 | | 1/2008 |
| WO | 2008021088 A2 | | 2/2008 |
| WO | WO-2008/155535 A1 | | 6/2008 |
| WO | 2009/111040 A1 | | 9/2009 |
| WO | WO-2009/140215 | | 11/2009 |
| WO | 2010003568 A1 | | 1/2010 |
| WO | WO 2010/043717 A2 | | 4/2010 |
| WO | WO-2012/032360 A2 | | 9/2011 |
| WO | WO-2013/182990 | | 12/2013 |
| WO | WO-2014/117236 A1 | | 8/2014 |
| WO | WO-2014/200705 A1 | | 12/2014 |
| WO | WO-2015/143654 | | 10/2015 |
| WO | WO-2016/038035 | | 3/2016 |
| WO | WO-2016/080846 | | 5/2016 |
| WO | 2016193136 A1 | | 12/2016 |
| WO | WO-2016/210247 | | 12/2016 |
| WO | WO-2017/040864 | | 3/2017 |
| WO | 2018051102 A1 | | 3/2018 |
| WO | 2018141063 A1 | | 8/2018 |
| WO | 2019192968 A1 | | 10/2019 |
| WO | 2020039073 A1 | | 2/2020 |
| WO | 2020/091804 A1 | | 5/2020 |
| WO | 2020176067 A1 | | 9/2020 |
| WO | 2021/076922 A1 | | 4/2021 |
| WO | 2021198116 A1 | | 10/2021 |

OTHER PUBLICATIONS

Bonacucina, et al., Rheological, mucoadhesive and release properties of Carbopol gels in hydrophilic cosolvents, International Journal of Pharmaceutics, 2004, pp. 115-130, vol. 282.

Chirife, J. et al., Antimicrobial Agents and Chemotherapy, In vitro antibacterial activity of concentrated polyethylene glycol 400 solutions, Sep. 1983, pp. 409-412, vol. 24, No. 3.

Macielag, et al., Substituted Salicylanilides as inhibitors of twocomponent regulatory systems in bacteria, J. Med. Chem., 1998, pp. 2939-2945, vol. 41.

Rajamuthiah, et al, Repurposing Salicylanilide Anthelmintic Drugs to Combat Drug Resistant *Staphylococcus aureus*, PLOS One, 2015, e0124595, vol. 10, No. 4.

Beers, et al., The Merck Manual of Medical Information, Second Home Edition, 2003, pp. 1222-1223.

Fischer, et al., Online article http://www.pharmazeutische-zeitung. de/index.php?id=1481&no_cache=1&sword_list%5B0%5D=holger &sword_list%5B1%5D=reimann, 2006, 6 pages [English Translation Previously Filed on Sep. 27, 2018].

Carvalho et al., "Nitazoxanide Disrupts Membrane Potential and Intrabacterial pH Homeostasis of *Mycobacterium tuberculosis*," ACS Medicinal Chemistry Letters, vol. 2, No. 11, pp. 849-854 (2011).

Tharmalingham et al., "Repurposing the anthelmintic drug niclosamide to combat Helicobacter pylori," Sci. Rep., 8:3701, pp. 1-12 (2018).

"Study ATx201-004, Ointment 2% or 4% in Impetigo," 2 pages.

Enroth, International Encyclopedia of Public Health, 2nd edition, 3:527-531.

Yu et al. (2018) "Niclosamide Exhibits Potent Anticancer Activity and Synergizes with Sorafenib in Human Renal Cell Cancer Cells", Cell Physiol Biochem, 47(3):957-971.

Ahn et al. (Mar. 16, 2017) "Anti-helminthic Niclosamide Inhibits Ras-driven Oncogenic Transformation Via Activation of GSK-3", Oncotarget, 8(19):31856-31863.

Amieva and El-Omar (Jan. 1, 2008) "Host-Bacterial Interactions in Helicobacter pylori Infection", Gastroenterology, 134(1):306-323.

Backert et al. (Jul. 15, 2016) "The Role of CagA in the Gastric Biology of Helicobacter pylori", Author manuscript, Published in final edited form as: Cancer Research, 76(14):4028-4031.

Burock et al. (2018) "Niclosamide a New Chemotherapy Agent? Pharmacokinetics of the Potential Anticancer Drug In a Patient Cohort of the NIKOLO Trial", Journal of Clinical Oncology, 36(15 suppl):e14536-e14536.

(56) References Cited

OTHER PUBLICATIONS

Burock et al. (2018) "Phase II Trial to Investigate the Safety and Efficacy of Orally Applied Niclosamide in Patients with Metachronous or Sychronous Metastases of a Colorectal Cancer Progressing after Therapy: The NIKOLO Trial", BMC Cancer, 18(1):297(7 pages).

Celli et al. (Aug. 25, 2009) "Helicobacter pylori Moves Through Mucus by Reducing Mucin Viscoelasticity", Proceedings of the National Academy of Sciences, 106(34):14321-14326.

Censini et al. (Dec. 1996) "cag, a Pathogenicity Island of Helicobacter pylori, Encodes Type I-specific and Disease-associated Virulence Factors", Proceedings of the National Academy of Sciences, 93(25):14648-14653.

Chan (Oct. 4, 2008) "Proton-pump Inhibitors in Peptic Ulcer Disease", The Lancet, 372(9645):1198-1200.

Cheung (Oct. 4, 2008) "Atrophic Gastritis Increases the Risk of Gastric Cancer in Asymptomatic Population in Korea", Gut and Liver, Sep. 2017, 11(5):575-576.

Chey et al. (Feb. 2017) "ACG Clinical Guideline: Treatment of Helicobacter pylori Infection", American Journal of Gastroenterology, 112(2):212-238.

Choi et al. (Mar. 22, 2018) "Helicobacter pylori Therapy for the Prevention of Metachronous Gastric Cancer", The New England Journal of Medicine, 378(12):1085-1095.

Chung et al. (Oct. 24-28, 2015) "23rd United European Gastroenterology Week".

Correa (Jun. 2013) "Gastric Cancer: Overview", Author manuscript, Published in final edited form as: Gastroenterology Clinics of North America, 42(2):211-217(8 pages).

Damjanov (May 2005) "Robbins and Cotran Pathologic Basis of Disease, 7th Edition", Shock, 23(5):482-483.

Deen et al. (May 2013) "The Impact of Autophagic Processes on the Intracellular Fate of Helicobacter pylori", Autophagy, 9(5):639-652.

Dubois and Borén (2007) "Helicobacter pylori is Invasive and it may be a Facultative Intracellular Organism", Author manuscript, Published in final edited form as: Cellular Microbiology, 9(5):1108-1116.

Eom et al. (Feb. 22, 2011) "Use of Acid-suppressive Drugs and Risk of Pneumonia: A Systematic Review and Meta-analysis", CMAJ, 183(3):310-319.

Galmiche and Rassow (Nov./Dec. 2010) "Targeting of Helicobacter pylori VacA to Mitochondria", Gut Microbes, 1(6):392-395.

Giannouli et al. (2014) "Use of Larvae of the Wax Moth Galleria Mellonella as an in Vivo Model to Study the Virulence of Helicobacter pylori", BMC Microbiology, 14(228):1-10.

Gisbert et al. (2015) "Helicobacter pylori Second-line Rescue Therapy with Levofloxacin- and Bismuth-containing Quadruple Therapy, after Failure of Standard Triple or Non-bismuth Quadruple Treatments", Alimentary Pharmacology & Therapeutics, 41(8):768-775.

Graham et al. (2010) "Helicobacter pylori Treatment in the Era of Increasing Antibiotic Resistance", Gut, 59(8):1143-1153.

Graham (2015) "Helicobacter pylori Update: Gastric Cancer, Reliable Therapy, and Possible Benefits", Gastroenterology, 148(4):719-731.

Gu (2008) "The Study on the Mechanisms of Helicobacter pylori Motility in Gastric Mucosal Colonization", Chinese Journal of Laboratory Medicine, 31:733-736.

Guruge et al. (Mar. 31, 1998) "Epithelial Attachment Alters the Outcome of Helicobacter pylori Infection", Proceedings of the National Academy of Sciences, 95(7):3925-3930.

Hagymási and Tulassay (Jun. 7, 2014) "Helicobacter Pylori Infection: New Pathogenetic and Clinical Aspects", World Journal of Gastroenterology, 20(21):6386-6399.

Hamdoun et al. (Mar. 2017) "Drug Repurposing of the Anthelmintic Niclosamide to Treat Multidrug-Resistant Leukemia", Frontiers in Pharmacology, 8(110):1-11.

Hamilton and Rath (2018) "Repurposing of Anthelminthics as Anticancer Drugs", Oncomedicine, 3:1-8.

Hessey et al. (1990) "Bacterial Adhesion and Disease Activity in Helicobacter Associated Chronic Gastritis", Gut, 31:134-138.

Huemer et al. (2018) "Impact of Antibiotic Treatment on Immune-checkpoint Blockade Efficacy in Advanced Non-squamous Non-small Cell Lung Cancer", Oncotarget, 9(23):16512-16520.

Imhann et al. (2016) "Proton Pump Inhibitors Affect the Gut Microbiome", Gut, 65(5):740-748.

Imramovsky et al. (2009) "Salicylanilide esters of N-protected amino acids as novel antimicrobial agents", Bioorganic and Medicinal Chemistry Letters, 19(2): 348-351.

Jakobsson et al. (Mar. 2010) "Short-Term Antibiotic Treatment Has Differing Long-Term Impacts on the Human Throat and Gut Microbiome", PLoS One, 5(3):1-12.

Kao et al. (Aug. 20, 2018) "The Antiparasitic Drug Niclosamide Inhibits Dengue Virus Infection by Interfering with Endosomal Acidification Independent of mTOR", PLoS One, 12(8):16 pages.

Kato et al. (2002) "Antibiotic Resistance of Helicobacter pylori Strains in Japanese Children", Journal of Clinical Microbiology, 40(2):649-653.

Kita et al. (2001) "CYP2C19 Genotype Related Effect of Omeprazole on Intragastric pH and Antimicrobial Stability", Pharmaceutical Research, 18(5):615-621.

Kuipers et al. (Apr. 18, 1996) "Atrophic Gastritis and Helicobacter pylori Infection in Patients with Reflux Esophagitis Treated with Omeprazole or Fundoplication", The New England Journal of Medicine, 334(16):1018-1122.

Kuipers (2006) "Proton Pump Inhibitors and Helicobacter pylori Gastritis: Friends or Foes?", Basic & Clinical Pharmacology & Toxicology, 99(3):187-194.

Lee et al. (2014) "Helicobacter pylori CagA Promotes Snail-mediated Epithelial-mesenchymal Transition by Reducing GSK-3 Activity", Nature Communications, 5(4423):1-13.

Malfertheiner et al.(2012) "Management of Helicobacter pylori infectiondthe Maastricht IV/ Florence Consensus Report", Gut, 61:646-664.

Matos et al. (2013) "Helicobacter pylori CagA and VacA Genotypes and Gastric Phenotype: A Meta-analysis", European Journal of Gastroenterology & Hepatology, 25(12):1431-1441.

McGuckin et al. (Oct. 2007) "Muc1 Mucin Limits Both Helicobacter pylori Colonization of the Murine Gastric Mucosa and Associated Gastritis", Gastroenterology, 133(4):1210-1218.

Mohammad et al. (2018) "Repurposing Niclosamide for Intestinal Decolonization of Vancomycin-resistant Enterococci", Author manuscript, Published in final edited form as: International Journal of Antimicrobial Agents, 51(6):897-904.

Nemeth et al. (Feb. 2015) "Bacteriostatic Versus Bactericidal Antibiotics for Patients with Serious Bacterial Infections: Systematic Review and Meta-analysis", The Journal of Antimicrobial Chemotherapy, 70(2):382-395.

Nguyen et al. (Sep. 1999) "Host Determinants of Helicobacter Pylori Infection and its Clinical Outcome", Helicobacter pylori, 4(3):185-197.

Noto et al. (2016) "The Mongolian Gerbil: A Robust Model of Helicobacter pylori-Induced Gastric Inflammation and Cancer", Author manuscript, Published in final edited form as: Methods in Molecular Biology, 1422:263-280(20 pages).

Odenbreit (2005) "Adherence Properties of Helicobacter pylori: Impact on Pathogenesis and Adaptation to the Host", International Journal of Medical Microbiology, 295(5):317-324.

Ottemann and Lowenthal (Apr. 2002) "Helicobacter pylori Uses Motility for Initial Colonization and to Attain Robust Infection", Infection and Immunity, 70(4):1984-1990.

Papastergiou et al. (Jan. 14, 2016) "Helicobacter pylori and Colorectal Neoplasia: Is there a Causal Link?", World Journal of Gastroenterology, 22(2):649-658.

U.S. Appl. No. 17/290,386, "Treatment of Inflammatory Conditions" filed Apr. 30, 2021, 127 pages.

Devine et al. (Feb. 1970) "Spectra of Susceptibility of Neisseria meningitidis to Antimicrobial Agents In Vitro", Journal of Applied Microbiology, 19(2):329-334.

Fifer et al. (Jun. 2016) "Failure of Dual Antimicrobial Therapy in Treatment of Gonorrhea", New England Journal of Medicine, 374(25):2504-2506.

Gwisai et al. (Jul. 12, 2017) "Repurposing Niclosamide as a Versatile Antimicrobial Surface Coating Against Device-

(56) References Cited

OTHER PUBLICATIONS

Associated, Hospital-Acquired Bacterial Infections", Biomedical Materials, 12(4):045010 (25 pages).
Hu et al. (May 5, 2017) "Novel and Effective Therapeutic Regimens for Helicobacter pylori in an Era of Increasing Antibiotic Resistance", Frontiers in Cellular and Infection Microbiology, 7:168 (20 pages).
Kadri et al. (Jun. 6, 2018) "Niclosamide, a Drug with Many (Re)purposes", ChemMedChem, 13(11):1088-1091.
Kratky et al. (Mar. 15, 2016) "Salicylanilide N-monosubstituted Carbamates: Synthesis and in Vitro Antimicrobial Activity", Bioorganic & Medicinal Chemistry, 24(6):1322-1330.
Lau et al. (Jul. 2001) "Provision of Phenotype-Matched Blood Units: no Need for Pre-Transfusion Antibody Screening", Haematologica, 86(7):742-748.
Sun et al. (1999) "Antituberculosis Activity of Certain Antifungal and Antihelmintic Drugs", Tubercle and Lung Disease: The Official Journal of the International Union against Tuberculosis and Lung Disease, 79(5):319-320.
Unemo Magnus (2015) "Current and Future Antimicrobial Treatment of Gonorrhoea—The Rapidly Evolving Neisseria Gonorrhoeae Continues to Challenge", BMC Infectious Diseases, 15(364):15 pages.
Van Doorn et al. (Mar. 2000) "Importance of Helicobacter Pylori CagA and VacA Status for the Efficacy of Antibiotic Treatment", Gut, 46(3):321-326.
Zhu et al. (Jul. 15, 2009) "Quantitative High-Throughput Screening Identifies Inhibitors of Anthrax-Induced Cell Death", Bioorganic & Medicinal Chemistry, 17(14):5139-5145.
"UK Standards for Microbiology Investigations: Identification of *Clostridium* species," Issued by the Standards Unit, Microbiology Services, PHE, Bacteriology—Identification, ID 8, Issue No. 4, 27 pages (2015).
Yutin et al., "A genomic update on clostridial phylogeny: Gram-negativespore-formers and other misplaced clostridia," Author Manuscript, Published in final edited form as: *Environ Microbiol.*, 15(10), pp. 263-2641 (2013).
Papastergiou et al. (Aug. 7, 2014) "Treatment of Helicobacter pylori Infection: Meeting the Challenge of Antimicrobial Resistance", World Journal of Gastroenterology, 20(29):9898-9911.
Pauk et al. (2013) "New Derivatives of Salicylamides: Preparation and Antimicrobial Activity Against Various Bacterial Species", Bioorganic & Medicinal Chemistry, 21:6574-6581.
Peek Jr. et al. (Jan. 2002) "Helicobacter pylori and Gastrointestinal Tract Adenocarcinomas", Nature Reviews Cancer, 2(1):28-37.
Pereira and Medeiros (Jan. 21, 2014) "Role of Helicobacter pylori in Gastric Mucosa-associated Lymphoid Tissue Lymphomas", World Journal of Gastroenterology, 20(3):684-698.
Romano MD et al. (2004) "Eradication of Helicobacter pylori: A Clinical Update", MedGenMed : Medscape general medicine, 6(1):19.
Schenk et al. (2000) "Effect of Helicobacter pylori Eradication on Chronic Gastritis During Omeprazole Therapy", Gut, 46:615-621.
Sekirov et al. (Oct. 2008) "Antibiotic-induced Perturbations of the Intestinal Microbiota Alter Host Susceptibility to Enteric Infection", Infection and Immunity, 76(10):4726-4736.
Sherwood et al. (2002) "Impact of Acid Secretion, Gastritis, and Mucus Thickness on Gastric Transfer of Antibiotics In Rats", Gut, 51(4):490-495.
Shimada et al. (Oct. 2007) "Role of Helicobacter Pylori Eradication in the Prevention of Peptic Ulcer in NSAID Users", Nihon Rinsho, 65(10):1824-1829.
Shiota et al. (Sep. 2015) "Antibiotic Resistance of Helicobacter pylori Among Male United States Veterans", Clin Gastroenterol Hepatol, 13(9):1616-1624(17 pages).
Stiefel et al. (Nov. 2006) "Suppression of Gastric Acid Production by Proton Pump Inhibitor Treatment Facilitates Colonization of the Large Intestine by Vancomycin-Resistant *Enterococcus* spp. and Klebsiella pneumoniae in Clindamycin-Treated Mice V", Antimicrob Agents Chemother, 50(11):3905-3907.
Takagi et al. (2018) "The Influence of Long-term Use of Proton Pump Inhibitors on the Gut Microbiota: An Age-sex-matched Case-control Study", Journal of Clinical Biochemistry and Nutrition, 62(1):100-105.
Tam et al. (Dec. 7, 2018) "Host-targeted Niclosamide Inhibits C. Difficile Virulence and Prevents Disease in Mice Without Disrupting the Gut Microbiota", Nature Communications, 9(5233):11 pages.
Thompson et al. (Nov. 1, 2017) "P1.07-008 Microbiome & Immunotherapy: Antibiotic Use Is Associated with Inferior Survival for Lung Cancer Patients Receiving PD-1 Inhibitors", Journal of Thoracic Oncology, Abstract Only, 12(11S2):S1998.
Thung et al. (Feb. 2016) "Review Article: the Global Emergence of Helicobacter Pylori Antibiotic Resistance", Aliment Pharmacol Ther., 43(4): 514-533.
Uemura and Okamoto (Aug. 1997) "Effect of Helicobacter Pylori Eradication on Subsequent Development of Cancer After Endoscopic Resection of Early Gastric Cancer", Cancer Epidemiol Biomarkers Prev, 6(8):639-642.
Wu et al.(Jan. 2013) "Diagnostic Accuracy of Narrow-band Imaging for the Differentiation of Neoplastic From Non-heoplastic Colorectal Polyps: a Meta-analysis", Colorectal Dis, 15(1):3-11.
Yamaoka et al. (1997) "Induction of Various Cytokines and Development of Severe Mucosal Inflammation by cagA Gene Positive Helicobacter Pylori Strains", Gut, 41(4):442-451.
Hassan et al., "Topical Niclosamide as a Protective Agent Against Schistosome Infection," Journal of the Egyptian Society of Parasitology, 1991, 21(3), 817-822.
Jabs et al. (Oct. 2000) "Guidelines for the Use of Immunosuppressive Drugs in Patients with Ocular Inflammatory Disorders: Recommendations of an Expert Panel", American Journal of Ophthalmology, 130(4): 492-513.
Ofori-Adjei et al. (Jan. 2008) "A Review of the Safety of Niclosamide, Pyrantel, Triclabendazole and Oxamniquine", The International Journal of Risk & Safety in Medicine, 20(3):113-122.
Pearson et al. (Apr. 1985) "Niclosamide Therapy for Tapeworm Infections", Annals of Internal Medicine, 102(4):550-551.
Cheng et al. (Dec. 15, 2010) "High-Throughput Identification of Antibacterials Against Methicillin-Resistant *Staphylococcus aureus* (MRSA) and the Transglycosylase", Bioorganic & Medicinal Chemistry, 18(24):8512-8529.
Garza-Gonzalez et al. (Feb. 14, 2014) "A Review of Helicobacter Pylori Diagnosis, Treatment, and Methods to Detect Eradication", World Journal of Gastroenterology, 20(6):1438-1449.
Huang et al. (Oct. 2013) "New Continuous Fluorometric Assay for Bacterial Transglycosylase Using Forster Resonance Energy Transfer", Journal of the American Chemical Society, 135(45):17078-17089.
Akiyama, et al., Recent Investigations of *Staphylococcus aureus* in Dermatology (Abstract cited in U.S. Appl. No. 15/662,691).
Cooper, et al., Systematic review of Propionibacterium acnes resistance to systemic antibiotics, Med J Aust., Med J Aust., Sep. 7, 1998), pp. 259-261, vol. 169, No. 5.
Cunliffe, et al., A Randomized, Double-Blind Comparison of a Clindamycin Phosphate/Benzoyl Peroxide Gel Formulation and a Matching Clindamycin Gel with Respect to Microbiologic Activity and Clinical Efficacy in the Topical Treatment of Acne Vulgaris, Clinical Therapeutics, 2002, pp. 1117-1133, vol. 24, No. 7.
Dobie, et al., Fusidic Acid Resistance in *Staphylococcus aureus*, Archives of Disease in Childhood, Jun. 14, 2017, pp. 74-77, vol. 89.
Fischer, et al., Niclosamide Cream: Recipe against bath Dermatitis, Online article http://www.pharmazeutische-zeitung.de/index.php?id=1481&no_cache=1&sword_list%5B0%5D=holger&sword_list%5B1%5D=reimann, 2006, 6 pages (Machine Translation).
Ghazi, et al., Antibacterial Effect and Toxicity of Synthesized Salicylanilide Derivatives, Zentralblatt für Mikrobiologie, 1986, pp. 225-232, vol. 3.
Hassanzadeh, et al., Bacterial Resistance to Antibiotics in Acne Vulgaris: An In Vitro Study, Indian Journal of Dermatology, 2008, pp. 122-124, vol. 53, No. 3.
Higaki, et al., Susceptibility of Propionibacterium acnes, *Staphylococcus aureus* and *Staphylococcus epidertnidis* to Kampo Formulations, The Journal of International Medical Research, 1997, pp. 318-324.

(56) References Cited

OTHER PUBLICATIONS

Hlasta, D.J., et al. Novel inhibitors of bacterial two-component systems with gram positive antibacterial activity: pharmacophore identification based on the screening hit closantel, Bioorganic & Medicinal Chemistry Letters, Jul. 1998, pp. 1923-1928, vol. 8, No. 14, 21.
Imperi, et al., New Life for an old drug: Antimicrobial, Agents and Chemotherapy, 2013, pp. 996-1005, vol. 557, No. 2.
Kratky, et al., New amino acid esters of salicylanilides active against MDR-TB and other microbes, European Journal of Medicinal Chemistry, Dec. 2010, pp. 6106-6113, vol. 45, No. 12.
Lundberg, et al., Efficacy of topical and systemic antibiotic treatment of meticillin-resistant *Staphylococcus aureus* in a murine superficial skin wound infection model, Int. J Antimicrob. Agents, 2013, pp. 272-275, vol. 42, No. 3.
Muir, et al., Degradation of Niclosamide (2, 5-Dichloro-4'-nitrosalicylanilide) in sediment and water systems, J. Agricultural and Food Chemistry, 1982, pp. 1028-1032, vol. 30, No. 6.
Nomura, et al., *Staphylococcus aureus* and atopic dermatitis, IRYO, 2002, pp. 62-66, vol. 54, No. 2. (Abstract cited in U.S. Appl. No. 15/662,691).
Rajamuthiah, et al., Whole Animal Automated Platform for Drug Discovery against Multi-Drug Resistant *Staphylococcus aureus*, PloS One, 2014, e89189, vol. 9, No. 2.
Rodriguez-Cavallini, et al., Etiologia bacteriana y susceptibilidad an antibioticos en pacientes con acne, Rev. Biomed., 2004, pp. 101-106, vol. 15.
Sanphui, et al., Pharmaceutical Cocrystals of Niclosamide, Crystal Growth & Design, 2012, pp. 4588-4599, vol. 12, No. 9.
Thiboutot, et al., New Insights into the Management of Acne: An update from the Global Alliance to Improve Outcomes in Acne Group, Journal of American Academy of Dermatology, May 2009, pp. S1-S50.
Unknown Author, OECD Guideline for the Testing of Chemicals, Acute Eye Irritation/Corrosion, OECD/OCDE, Adopted Apr. 24, 2002, 14 pages.
Van Tonder, et al, Preparation and physicochemical properties of niclosamide anhydrate and two monohydrates, Int. J. Pharm., 2004, pp. 417-432, vol. 269, No. 2.
Vinsova, et al., Salicylanilide acetates, Molecules, 2007, 12 pages, vol. 12, No. 1.
Wulff, et al., Cream formulations protecting against cercarial dermatitis by Trichobilharzia, Parasitology Research, Jun. 2007, pp. 91-97, vol. 101, No. 1 (Abstract cited in U.S. Appl. No. 15/662,691).
Zhao, et al., In vitro antimicrobial activity of closantel to *Staphylococcus aureus*, 2012, pp. 2019-2021, vol. 22, No. 10 (English Abstract).

* cited by examiner

NON-AQUEOUS TOPICAL COMPOSITIONS COMPRISING A HALOGENATED SALICYLANILIDE

This invention relates to non-aqueous topical compositions comprising a halogenated salicylanilide; the use of such compositions in the topical treatment or prevention of diseases and infections, particularly those caused by Gram-positive bacteria. For example for use in the topical treatment or prevention of skin infections, acne, atopic dermatitis and impetigo and for bacterial decolonisation, e.g. prior to surgical procedures. Also disclosed are methods for preparing the composition.

BACKGROUND

Bacterial resistance to antibiotics is becoming more prevalent and there is an ongoing need to identify new antibiotic drugs, particularly drugs which are effective against bacteria resistant to conventional antibiotics, for example methicillin-resistant *Staphylococcus aureus* ("MRSA").

MRSA infections on the skin and in the airways are common in hospital settings and the broad spectrum resistance of the bacteria to almost all classes of antibiotics (e.g. methicillin, fusidic acid and mupirocin) make it particularly difficult to combat.

Topical antibiotics are an attractive treatment option for infections of the skin and soft tissue because the active agent can be applied directly to the site of infection and may reduce side-effects associated with systemic use of antibiotics. However, there are currently limited topical antibiotics available.

Fusidic acid is an antibiotic derived from *Fusidium coccineum* that has been used for over 35 years to treat infections with *Staphylococcus aureus*. Fusidic acid is commonly prescribed for the treatment of skin infections caused by *Staphylococcus aureus*. Such infections include impetigo, angular cheilitis (an infection around the mouth), and infected dermatitis. However, *S. aureus* can rapidly develop resistance to fusidic acid, even after a short course of treatment. As a result, fusidic acid is generally used systemically in combination with another antibiotic agent to reduce the risk of resistance developing. Topical use of fusidic acid as a monotherapy is considered to be a high risk factor in the development of resistance. Topical use of fusidic acid is therefore restricted to short courses of treatment and for patients outside hospital without underlying skin conditions, together with close monitoring of local antibiotic susceptibility patterns (Dobie et al; *Arch Dis Child* 2004; 89:74-77). There are currently limited alternative topical antibiotics available.

Resistance to fusidic acid may also be linked to the development of resistance in other bacteria, potentially leading to the spread of multiply-drug resistant *Staphylococcus aureus* such as MRSA.

Mupirocin is a topical antibiotic used to treat superficial skin infections and to control the spread of MRSA. Mupirocin resistance was observed shortly after it became available. The prevalence of mupirocin resistance among MRSA isolates has been described mostly in hospitalized adult and elderly patients with wide variability, ranging from 0 to 65% of isolates. Rates of resistance have been shown to correlate with increased use in closed inpatient settings. Very restrictive mupirocin prescriptions for local treatment are now recommended.

Impetigo is a highly contagious bacterial infection of the superficial layers of the epidermis. Impetigo is one of the most common skin diseases among children, accounting for about 10% of skin diseases treated in US pediatric clinics. The bacteria typically considered to be responsible are *Staphylococcus aureus* and *Streptococcus pyogenes*, and often a combination of the two. Impetigo is usually transmitted by direct contact but fomites also play an important role. MRSA is being found with increasing frequency as a causative bacteria of impetigo. Impetigo has three common clinical varieties: impetigo contagiosa (common impetigo), bullous impetigo, and ecthyma. Features of all three types of impetigo, however, may coexist in any individual patient.

Topical mupirocin (commercially available as 2% Bactroban ointment and cream) is a treatment option for impetigo. For some patients, mupirocin is a viable treatment option for MRSA, however, resistance to mupirocin has been widely reported.

Topical fusidic acid (commercially available as 2% Fucidin cream) is used for treatment of impetigo, and is thought to be equally as effective as mupirocin. However, the utility of fusidic acid for the treatment of impetigo is limited by the problem of resistance development, as discussed above.

Fusidic acid-resistant *Staphylococcus aureus* (FRSA) has been identified as a causative bacteria in outbreaks of impetigo and its emergence has been associated with increased use of topical fusidic acid. Accordingly, the utility of fusidic acid as first-line agent for the treatment of impetigo has become questionable.

Retapamulin (commercially available as 1% Altabax ointment), is a recently approved pleuromutilin antibiotics for the topical treatment of impetigo caused by *Staphylococcus aureus* (methicillin-susceptible only) or *Streptococcus pyogene*.

Wounds and burns are often colonized by microbiologic pathogens, including Gram-positive bacteria, such as *Staphylococcus aureus* and/or *Streptococcus pyogenes*. Despite the common occurrence of wound infections, only a limited number of topical antibiotics are approved for the treatment of infected wounds. Mupirocin is approved for the topical treatment of infected wounds, however, emerging bacterial resistance to mupirocin is becoming a concern. In coagulase-negative staphylococci isolates, mupirocin resistance rates are high, ranging from 12.7% in Europe to 38.8% in the United States. Retapamulin is also used topically for wound treatment. Fusidic acid (commercially available as Fucidin, LEO Pharma) is approved for use in the treatment of primary and secondary skin infections caused by sensitive strains of *Staphylococcus aureus, Streptococcus* species and *Corynebacterium minutissimum*. However, as discussed above, development of resistance is common with these agents.

The Gram-positive bacteria, *Propionibacterium*, particularly *Propionibacterium acnes* are implicated in the pathogenesis of acne. Topical antibiotics have been used for many years in the treatment of acne. However, current treatment guidelines discourage such use due to the emergence of antibiotic resistance. The incidence of antibiotic resistance in acne has risen steadily over the last 40 years from 20% in 1978 to 72.5% in 1995 (Cooper et al. Systematic review of *Propionibacterium acnes* resistance to systemic antibiotics. *Med J Aust*. 1998, Sep. 7; 169(5):259-61). The most commonly prescribed topical antibiotics for acne are erythromycin and clindamycin. However, resistance to these topical antibiotic monotherapies has been observed, even after relatively short periods of treatment of 8 weeks (Cunliffe et al A randomized, double-blind comparison of a clindamycin phosphate/benzoyl peroxide gel formulation and a matching clindamycin gel with respect to microbiologic activity and clinical efficacy in the topical treatment of acne vulgaris; *Clin Ther.* 2002 July; 24(7):1117-33). The development of resistant Propionibacteria increases the pathogenicity of the organism. Additionally, prolonged treatment regimens using topical antibiotics for the treatment of acne have resulted in selection pressure or the transfer of resistant genes to potentially more pathogenic bacteria, such as certain strains of Staphylococci or Streptococci. The Global Alliance to Improve Outcomes in Acne (*J Am Acad. Dermatol.* 2009 May; 60(5 Suppl):S1-50) recommends that topical antibiotics should be used for the shortest duration possible and should not be used as monotherapy but in combination with benzoyl peroxide to reduce the emergence of resistant *Propionibacterium acnes*.

There is therefore a need for new topical antibiotics, for which development of resistance is not widespread in the target bacteria, for the prevention and treatment of topical infections caused or contributed to by Gram-positive bacteria such as *Staphylococcus aureus, Streptococcus pyogenes* and *Propionibacterium acnes*.

The halogenated salicylanilides are a series of compounds generally used as anthelmintic agents. Such compounds include niclosamide.

Niclosamide is a known taenicide effective against several parasitic tapeworms of livestock and pets (e.g. *Taenia* spp, *Moniezia* spp) and also against rumen flukes (*Paramphistomum* spp) and blood flukes (*Schistosoma* spp.). This is in contrast with most other salicylanilides, which generally exhibit activity as flukicides but not as taenicides.

Niclosamide is currently used in humans as an anthelmintic drug to treat intestinal infections and displays overall low toxicity, it is poorly soluble in water, shows low intestinal absorption, and once in the bloodstream, it is quickly cleared via the urinary tract or by enzymatic metabolism in the liver. Therapeutically it is useful against cestoda in humans.

Niclosamide has also been shown to prevent the penetration of *Schistosoma mansoni* through the human skin. As well as used as an anticancer drug, pesticide and as an anti-trypanosoma drug. Virtually all applications and proposed applications of niclosamide target eukaryotic organisms.

Niclosamide has also been shown to inhibit viral replication in human cells. However, the mechanism is believed to be through targeting human host cells to provide conditions that prevent the viral life rather than specifically targeting the virus. Accordingly, the anti-viral application of niclosamide results from its ability to target eukaryotic processes.

Niclosamide is commercially available in a number of formulations including, but not limited to Bayer73®, Bayer2353®, Bayer25648®, Bayluscid®, Baylucide®, Cestocid®, Clonitralid, Dichlosale®, Fenasal®, HL 2447®, Iomesan®, Iomezan®, Manosil®, Nasemo®, Niclosamid®, Phenasal®, Tredemine®, Sulqui®, Vermitid®, Vermitin® and Yomesan®.

Other known halogenated salicylanilides include closantel, rafoxanide, and oxyclozanide. These compounds are also primarily used as anthelmintic agents.

Niclosamide has been proposed as a possible systemic treatment for chronic lung infections caused by the proteobacterium *Pseudomonas aeruginosa* and the actinobacterium *Mycoplasmum tuberculosis*. Niclosamide has been shown to reduce the quorum sensing response as well as the production of quorum sensing metabolites in *P. aeruginosa*. Since quorum sensing is considered an important process for the pathogenicity during chronic lung infections caused by this bacterium, it led to proposal that niclosamide could be used as an adjuvant therapy for these infections. Niclosamide does not affect the growth of *P. aeruginosa* and accordingly does not have any direct antibacterial activity. The concentration required for optimal activity was 20 µM, however, some inhibition was detected at 1 µM. (F. Imperi et al., *Antimicrobial, Agents and Chemotherapy*, 557(2), 996-1005 (2013)).

Ghazi et al. (*Zentralbl. Mikrobiol.* 141 (1986), 225-232) tested the antibacterial effect and toxicity of synthesized salicylanilide derivatives against *Escherichia coli, Bacillus subtilis, Pseudomonas aeruginosa* and *Staphylococcus aureus*.

J. Vinsova et al. describe the antibacterial activity of salicylanilides (*Molecules, vol.* 12, no. 1, pp. 1-12, 2007; *Bioorganic and Medicinal Chemistry Letters*, vol. 19, no. 2, pp. 348-351, 2009; *European Journal of Medicinal Chemistry*, vol. 45, no. 12, pp. 6106-6113, 2010).

M. J. Macielag et al. tested the antibacterial activity of closantel and related derivatives against the drug-resistant organisms, methicillin-resistant *Staphylococcus aureus* (MRSA) and vancomycin-resistant *Enterococcus faecium* (VREF) (*J. Med. Chem.*, 41(16), 2939-45 (1998)).

D. J. Hlasta et al found that closantel had antibacterial activity against drug resistant *S. aureus* and *E. faecium* (Bioorg. Med. Chem. Letters, 8(14), 1923-28 (1998)).

R. Rajamuthiah et al. identified closantel as a hit in a high throughput liquid screening assay and found anti-staphylococcal activity of closantel against vancomycin-resistant *S. aureus* isolates and other Gram-positive bacteria. (*PloS One*, 2014, 9(2): e89189).

GB 2,456,376 and WO 2008/155535 describes the use of halogenated salicylanilides for the treatment of acne, wherein propionibacteria is the bacteria causing the acne. There is no mention of the problem with development of resistance.

U.S. Pat. No. 8,846,646 discloses compositions comprising propylene glycol have antibacterial activity against *Propionibacterium Acnes* and may be used to treat acne.

Chirife et al. (*Antimicrobial Agents and Chemotheer.*, 24(3), (1983), 409-412) discloses aqueous solutions of PEG 400 had an antibacterial effect against certain bacteria.

As disclosed herein, the inventors have found that halogenated salicylanilides (for example, closantel, rafoxanide, oxyclozanide, or niclosamide) are potent against Gram-positive bacteria, such as *Staphylococcus aureus, Streptococcus pyogenes* or *Propionibacterium acnes*. The inventors have found that Gram-positive bacteria treated with a halogenated salicylanilide exhibit a low frequency of developing spontaneous resistant mutants compared to that observed with commonly used topical antibiotics. The reduced frequency of resistant mutants is expected to enable the halogenated salicylanilides to be used topically for prolonged treatment periods for the treatment and/or prevention of Gram-positive infections with a minimal risk of bacterial resistance to the halogenated salicylanilide emerging.

Effective topical administration of an antibiotic drug to for example the skin requires the drug to permeate into and through the stratum corneum and into the epidermis and dermis in sufficient concentration to provide an antibacterial effect against the bacteria present in the skin at the site of infection. Optimal topical compositions provide drug concentrations in excess of the MIC of the bacteria for prolonged periods of time, thereby ensuring effective killing or inhibition of the bacteria.

Halogenated salicylanilides, such as niclosamide, are very insoluble in water. Niclosamide in anhydrous form readily absorbs moisture and the forms niclosamide monohydrate, which is even less soluble than the anhydrate. Aqueous compositions of niclosamide are therefore prone to instability and precipitation of the niclosamide (*Int. J. Pharm.*, 269(2), 2004, 417-32; Crystal Growth & Design, 12(9), 4588-4599 (2012)). Furthermore, in aqueous media, an undesirable growth of particle size of the niclosamide or niclosamide salts is observed even after relatively short periods of time. The presence of niclosamide in solid form is undesirable for the topical administration of a drug, because it limits absorption of the drug. Furthermore precipitation of the drug either during storage of the composition or when topically applied and may result in variable rates of absorption.

Niclosamide is also reported in J. Agricultural and Food Chemistry, 30(6), 1028-1032 (1982) to be sensitive to light induced degradation in water.

GB 1,527,638 discloses an oil-based suspension of niclosamide with particles of less than 2 μm.

WO1998/056390 describes a solution in the form of an anthelmintic composition for oral administration, which comprises a pharmacologically acceptable dissolved salt of niclosamide in a pharmacologically acceptable (polar) organic solvent.

U.S. Pat. No. 3,152,039 discloses compositions comprising certain brominated salicylanilides, wherein an alkanolamine is used to enhance the solubility of the brominated salicylanilide.

RU 2,227,025 discloses a composition comprising rafoxanide, benzyl alcohol, triethanolamine, dimethyacetamide and polyethylene glycol.

Bonacucina et al. *Int. Journal of Pharmaceutics* 282, 2004, 115-130 discloses gels formed from carbopol and PEG 400 comprising paracetamol.

There remains a need for compositions suitable for the topical delivery of halogenated salicylanilides, which provides a potent antibacterial effect against Gram-positive skin infections when applied topically applied to the skin. Suitably the topical compositions provide good penetration into the skin thereby providing high concentration of the halogenated salicylanilide in, for example the dermis and epidermis. Suitably the topical compositions result in minimal systemic exposure to the halogenated salicylanilide following topical application of the composition. Suitably the topical compositions are well tolerated when applied topically, for example and result in little or no skin irritation following application.

BRIEF SUMMARY OF THE DISCLOSURE

According to a first aspect of the invention there is provided a non-aqueous topical composition comprising:
(i) a halogenated salicylanilide selected from niclosamide, rafoxanide, oxyclozanide and closantel, or a pharmaceutically acceptable salt thereof; and
(ii) polyethylene glycol (PEG) with a melting point of less than 40° C.;
with the proviso that when the composition comprises niclosamide or rafoxanide, or a pharmaceutically acceptable salt thereof, the composition further comprises a gel forming agent or a non-polymeric glycol (for example propylene glycol).

In this first aspect of the invention when the composition comprises niclosamide or rafoxanide, or a pharmaceutically acceptable salt thereof, the composition further comprises a gel forming agent or a non-polymeric glycol (for example propylene glycol), the gel forming agent may be any gel-forming agent provided it is not a PEG with a melting point of less than 40° C. Examples of gel forming agents which may be used include any of the gel-forming agents disclosed herein.

The compositions of the invention are for use in the topical treatment diseases or infections. As such the composition is suitably in a form wherein it can be readily applied topically to, for example, the skin. The composition may be in the form of a liquid, lotion, ointment, cream or gel.

Suitably the PEG in the composition is selected such that the composition together with any other components of the composition (e.g. in the form of a liquid, semi-solid or gel composition) can easily be applied to, spread over and/or rubbed into the skin. It may be that the PEG has a melting point that is less than 35° C. In certain embodiments the PEG is selected such that it is soft or, suitably molten at body temperature. For example, the PEG may have a melting point of 32° C. or less, or less than 30° C., or less than 25° C.

In certain embodiments of the compositions of the invention the PEG has an average molecular weight of 1000 or less, for example 800 or less or particularly 600 or less. In a particular embodiment the PEG has an average molecular weight of about 400 (i.e. PEG 400). In another embodiment the PEG has an average molecular weight of from about 200 to about 600.

In certain embodiments of the compositions of the invention the PEG is present in an amount of at least 5% by weight of the composition. For example the PEG is present in an amount of at least: 10%, 15%, 20%, 25%, 30%, 35% or 40% by weight of the composition.

The inventors have found that the presence of high concentrations of PEG in the compositions of the invention provide particularly high concentrations of the halogenated salicylanilide (for example niclosamide) in the dermis and/or epidermis following topical administration to the skin which are well in excess of the minimum inhibitory concentration of Gram-positive bacteria residing in, for example skin tissue. The compositions of the invention are therefore expected to be effective in the topical treatment or prevention of infections or diseases caused by Gram-positive bacteria. Accordingly in certain embodiments the PEG is present in an amount of at least 45%, at least 50%, at least 55%, at least 60%, at least 65%, at least 70%, at least 75%, at least 80%, at least 85%, at least 90% or at least 95% by weight of the composition.

In certain embodiments the composition of the invention comprises a glycol. The glycol is suitably a non-polymeric glycol. Non-polymeric glycols are glycols which do not comprise polymeric moieties as present in for example polyethylene glycol. Particular non-polymeric glycols include, for example an alkylene glycol (e.g. a $C_{2-8}$ alkyleneglycol or particularly a $C_{2-6}$ alkyleneglycol), especially propylene glycol. In these embodiments the non-aqueous composition comprises the glycol, the PEG and the halogenated salicylanilide and optionally other excipients. The presence of a non-polymeric glycol (e.g. propylene glycol is particularly suitable when the composition of the invention is in the form of a topical ointment or cream composition.

In certain embodiments the compositions of the invention comprise a non-polymeric glycol (e.g. propylene glycol) in an amount of at least: 5%, 10%, 15%, 20%, 25%, 30%, 35%, 40%, 45%, 50% or 55% by weight of the composition. For example the composition comprises from 5% to 35%, or from 8% to 30%, or from 10 to 30% by weight glycol (e.g. propylene glycol).

In certain embodiments the composition of the invention is in the form of a non-aqueous topical gel and further comprises a gel-forming agent. Examples of gel-forming agents which may be used in the compositions are set out below.

In certain embodiments the composition comprises an absorption enhancer in addition to the PEG and the halogenated salicylanilide. Suitable absorption enhancers are disclosed in the detailed description below. It may be that the absorption enhancer is selected from be 2-(2-ethoxyethoxy) ethanol (Transcutol) and glycerol.

Also provided is a non-aqueous topical composition comprising:
 (i) a halogenated salicylanilide selected from niclosamide, rafoxanide, oxyclozanide and closantel, or a pharmaceutically acceptable salt thereof; and
 (ii) polyethylene glycol (PEG) with an average molecular weight of 600 or less;
 (iii) an absorption enhancer selected from 2-(2-ethoxyethoxy)ethanol (Transcutol) and glycerol.

Also provided is a non-aqueous topical composition comprising:
 (i) from about 0.1% to about 10% by weight (for example from about 0.5% to about 5% by weight) of a halogenated salicylanilide selected from niclosamide, rafoxanide, oxyclozanide and closantel, or a pharmaceutically acceptable salt thereof; and
 (ii) at least 10% (for example at least 20%, 30%, 40%, 50% or 60%) by weight polyethylene glycol (PEG) with an average molecular weight of 600 or less;
 (iii) from about 1% to about 40% (for example about 5% to about 20%) by weight an absorption enhancer selected from 2-(2-ethoxyethoxy)ethanol (Transcutol) and glycerol or a mixture thereof.

Also provided is a non-aqueous topical composition comprising:
 (i) from about 0.1% to about 10% by weight (for example from about 0.5% to about 5% by weight) of a halogenated salicylanilide selected from niclosamide, rafoxanide, oxyclozanide and closantel, or a pharmaceutically acceptable salt thereof; and
 (ii) at least 10% (for example at least 20%, 30%, 40%, 50% or 60%) by weight polyethylene glycol (PEG) with an average molecular weight of 600 or less;
 (iii) from about 10 to about 30% (for example about 10 to about 25%) by weight propylene glycol; and
 (iv) from about 1% to about 40% (for example about 5% to about 20%) by weight an absorption enhancer selected from 2-(2-ethoxyethoxy)ethanol (Transcutol) and glycerol or a mixture thereof.

The inventors have found that the topical compositions of the invention comprising more than 60% by weight of PEG provide an enhanced antibacterial effect compared to the use of PEG alone or a halogenated salicylanilide (for example niclosamide) alone.

Accordingly a further aspect of the invention provides a non-aqueous topical composition comprising:
 (i) a halogenated salicylanilide, or a pharmaceutically acceptable salt thereof; and
 (ii) greater than 60% by weight of a polyethylene glycol (PEG), wherein the average molecular weight of the PEG is less than 600.

Also provided is a non-aqueous topical composition comprising:
 (i) a halogenated salicylanilide selected from niclosamide, rafoxanide, oxyclozanide and closantel, or a pharmaceutically acceptable salt thereof; and
 (ii) greater than 60% by weight of a polyethylene glycol (PEG), for example a PEG with an average molecular weight of 600 or less.

Also provided is a non-aqueous topical composition comprising:
 (i) a halogenated salicylanilide selected from niclosamide, rafoxanide, oxyclozanide and closantel, or a pharmaceutically acceptable salt thereof; and
 (ii) greater than 60% by weight of a polyethylene glycol (PEG), wherein the average molecular weight of the PEG is 600 or less.

In certain embodiments the composition of the invention is in the form of a non-aqueous topical gel. Accordingly there is provided a non-aqueous topical gel composition comprising:
 (i) a halogenated salicylanilide, or a pharmaceutically acceptable salt thereof;
 (ii) greater than 60% by weight of a PEG, wherein the average molecular weight of the PEG is less than 600; and
 (iii) a gel-forming agent.

Also provided is a non-aqueous topical gel composition comprising:
 (i) a halogenated salicylanilide selected from niclosamide, rafoxanide, oxyclozanide and closantel, or a pharmaceutically acceptable salt thereof;
 (ii) polyethylene glycol (PEG) with a melting point of less than 40° C.; and
 (iii) a gel forming agent.

Suitably the PEG is a PEG with an average molecular weight of 800 or less, preferably 600 or less. Also provided is a non-aqueous topical gel composition comprising:
 (i) a halogenated salicylanilide selected from niclosamide, rafoxanide, oxyclozanide and closantel, or a pharmaceutically acceptable salt thereof;
 (ii) greater than 60% by weight of a PEG, wherein the average molecular weight of the PEG is 600 or less; and
 (iii) a gel-forming agent.

When the composition is in the form of a topical non-aqueous gel composition, the gel-forming agent may, for example, be a carbomer. It may be that the gel forming agent is a carbomer selected from the group consisting of carbomer 910, carbomer 934P, carbomer 940GE, carbomer 941GE, carbomer 971P and carbomer 974P. It may be that the gel-forming agent is carbomer 974P. Other examples of gel-forming agents are disclosed in the Detailed Description below.

It may be that the halogenated salicylanilide, or a pharmaceutically acceptable salt thereof is a compound of the formula (I), or a pharmaceutically acceptable salt thereof; wherein the compound of formula (I) is as described in the Detailed Description below.

It may be that the halogenated salicylanilide, or a pharmaceutically acceptable salt thereof is a compound of the formula (II), or a pharmaceutically acceptable salt thereof; wherein the compound of formula (II) is as described in the Detailed Description below.

It may be that the halogenated salicylanilide is selected from the group consisting of niclosamide, closantel, oxyclozanide and rafoxanide, or a pharmaceutically acceptable salt thereof. It may be that the halogenated salicylanilide is niclosamide or a pharmaceutically acceptable salt thereof. It may be that the halogenated salicylanilide is niclosamide or a hydrate thereof. It may be that the halogenated salicylanilide is niclosamide. In particular the halogenated salicylanilide is anhydrous niclosamide.

It may be that the halogenated salicylanilide is dissolved in the non-aqueous composition, for example the non-aqueous composition (for example a non-aqueous gel composition described herein). In other embodiments a proportion of the halogenated salicylanilide is dissolved in the non-aqueous composition and a proportion is dispersed in the composition.

It may be that the halogenated salicylanilide is present in an amount of up to 10% by weight of the composition, for example from 0.05% to 4.5% by weight of the composition, from 1% to 3% by weight, from 1.5% to 4.5% by weight. For example, at about 2% by weight of the composition or at about 4% by weight of the composition.

It may be that the non-aqueous gel composition comprises or consists of:
(i) 0.1% to 5% by weight of niclosamide, or a pharmaceutically acceptable salt thereof;
(ii) 70% to 98% (for example 85% to 98%) by weight PEG, wherein the average molecular weight of the PEG is 600 or less; and
(iii) a gel forming agent.

It may be that the non-aqueous gel composition comprises or consists of:
(i) 0.1% to 5% by weight of niclosamide, or a pharmaceutically acceptable salt thereof;
(ii) 85% to 98% by weight PEG, wherein the average molecular weight of the PEG is 600 or less; and
(iii) 0.5% to 10% by weight of gel forming agent.

It may be that the non-aqueous gel composition comprises or consists of:
(i) 0.1% to 4.5% by weight of niclosamide, or a pharmaceutically acceptable salt thereof;
(ii) 86% to 98% by weight PEG, wherein the average molecular weight of the PEG is 600 or less, for example PEG 400; and
(iii) 0.5% to 10% by weight of gel forming agent.

It may be that the non-aqueous gel composition comprises or consists of:
(i) 0.1% to 3% (for example 1.5% to 2.5%, or about 2%) by weight of niclosamide, or a pharmaceutically acceptable salt thereof;
(ii) 94% to 98% by weight of PEG 400; and
(iii) a gel forming agent.

It may be that the non-aqueous gel composition comprises or consists of:
(i) 0.1% to 3% (for example 1.5% to 2.5%, or about 2%) by weight of niclosamide, or a pharmaceutically acceptable salt thereof;
(ii) 94% to 98% by weight of PEG 400; and
(iii) 1% to 3% by weight of a gel forming agent.

It may be that the non-aqueous gel composition comprises or consists of:
(i) 0.1% to 4.5% by weight of niclosamide, or a pharmaceutically acceptable salt thereof;
(ii) 70% to 98% (for example 86% to 98%) by weight PEG 400; and
(iii) 0.5% to 10% by weight of a carbomer gel forming agent.

It may be that the non-aqueous gel composition comprises or consists of:
(i) 1.5% to 4.5% by weight (for example about 2% or about 4%) by weight of niclosamide, or a pharmaceutically acceptable salt thereof;
(ii) 70% to 98% (for example 86% to 98%) by weight PEG 400; and
(iii) 0.5% to 10% by weight of a carbomer gel forming agent.

It may be that the non-aqueous gel composition comprises or consists of:
(i) 0.1% to 3% (for example 1% to 3%, 1.5% to 2.5%, or about 2%) by weight of niclosamide, or a pharmaceutically acceptable salt thereof;
(ii) 70% to 98% (for example 94% to 98%) by weight of PEG 400; and
(iii) 1% to 3% by weight of a carbomer, for example carbomer 974P.

It may be that the non-aqueous gel composition comprises or consists of:
(i) 3.5% to 4.5% (for example about 4%) by weight of niclosamide, or a pharmaceutically acceptable salt thereof;
(ii) 70% to 92.5% (for example 92.5% to 95.5%) by weight of PEG 400; and
(iii) 1 to 3% by weight of a carbomer, for example carbomer 974P.

It may be that any of the non-aqueous compositions described herein do not comprise short-chain alkyl monohydroxy alcohol (e.g. $C_{1-6}$-alkyl monohydroxy alcohol, or more particularly a $C_{1-4}$-alkyl monohydroxy alcohol such as ethanol, propanol or isopropanol), or benzyl alcohol. For example the composition does not contain methanol, ethanol, propanol or isopropyl alcohol. For example the composition does not comprise ethanol or benzyl alcohol.

It may be that the non-aqueous compositions described herein (for example a non-aqueous gel composition) does not comprise ethanol. Thus the composition may be a non-aqueous, non-ethanol composition. Suitably the composition may be a non-aqueous, ethanol free topical gel composition.

It may be that the non-aqueous compositions described herein do not comprise an alkanol amine, for example wherein the composition does not comprise triethanolamine.

It may be that the non-aqueous composition provides a local pH of greater than 4.5 at the site of infection following topical application of the composition. It may be that the non-aqueous composition provides a local pH of less than 6 at the site of infection following topical application of the composition. Suitably the non-aqueous composition provides a local pH in the range of from about 4.5 to about 6 at the site of infection following topical application of the composition (for example topical application to skin infected with Gram-positive bacteria).

The non-aqueous compositions, for example the non-aqueous gel compositions, according to the present invention are expected to provide a number of advantageous properties. Certain non-aqueous compositions of the invention may provide high permeability of the halogenated salicylanilide into the skin following topical application, thereby providing high local drug content if the dermis, epidermis and/or stratum corneum and thus provide a potent antibacterial effect in the skin at the site of infection. Topical administration of the composition of the invention (for example a non-aqueous gel composition) is expected to result in very low systemic exposure to the halogenated salicylanilides, thereby reducing the likelihood of undesirable systemic side-effects.

Certain non-aqueous compositions of the invention exhibit good tolerability when applied topically to a site of infection, such as the skin. For example, the compositions suitably exhibit acceptable, or preferably no undesirable effects on the skin following topical application such as skin inflammation or sensitisation, for example, skin dryness, exfoliation, itching, burning sensations or erythema. A favourable tolerability profile may provide topical treatments that are suitable for prolonged topical treatment regimens with a low risk of undesirable local side-effects which, if present, could reduce patient compliance and/or exacerbate the effects of a skin infection (for example arising through a patient scratching an infected lesion).

The compositions of the invention (for example the non-aqueous gel compositions) described herein may provide advantageous chemical and physical stability properties, particularly when compared to aqueous based compositions comprising a halogenated salicylanilide. Such advantages may comprise one or more of no or low rates of precipitation of the drug from the composition during storage and/or upon topical application to the skin. The non-aqueous compositions of the invention are suitably chemically stable against degradation of the halogenated salicylanilide during storage or use of the non-aqueous composition. For example the compositions may be thermally stable and/or light stable during storage and use. As illustrated in the examples herein, certain of the non-aqueous gel compositions of the invention are photo-stable.

Successful treatment of an infection requires exposure to the antibacterial agent for sufficient time and at a sufficient concentration to ensure the bacterial cells are reduced or eradicated from the site of infection. However, a problem associated with topical treatment of infections, for example skin infections, is poor patient compliance with the prescribed treatment regimen. Patient compliance is a particular problem in topical treatment regimens, because patients will often forget to apply the topical treatment especially towards the end of a treatment regimen when the signs and symptoms of the infection start to improve. Poor compliance, for example, application of the incorrect dose or missing doses can result in variable concentrations of the antibacterial agent and an increased risk of resistant strains emerging, potentially resulting in failure of the treatment. The low frequency of mutations conferring resistance to the halogenated salicylanilides is expected to reduce the risk of resistance emerging even if patient compliance is poor. The non-aqueous compositions of the invention comprising a halogenated salicylanilide are therefore expected to provide an effective topical treatment of bacterial infections.

A further aspect of the invention provides a non-aqueous composition of the invention for use in the topical prevention or treatment of an infection or disease caused by Gram-positive bacteria.

A further aspect of the invention provides a method of treating or preventing a disease or infection caused by Gram-positive bacteria in a subject, the method comprising topically administering to the subject a therapeutically effective amount of the non-aqueous composition to the subject.

A further aspect of the invention provides processes for the preparation of the non-aqueous gel composition.

Further aspects and features of the invention are set out in the detailed description below.

BRIEF DESCRIPTION OF THE DRAWINGS

FIG. 7 shows the median accumulated niclosamide in the receptor fluid for the tested compositions F1 and F4.

DETAILED DESCRIPTION

Figure 1:
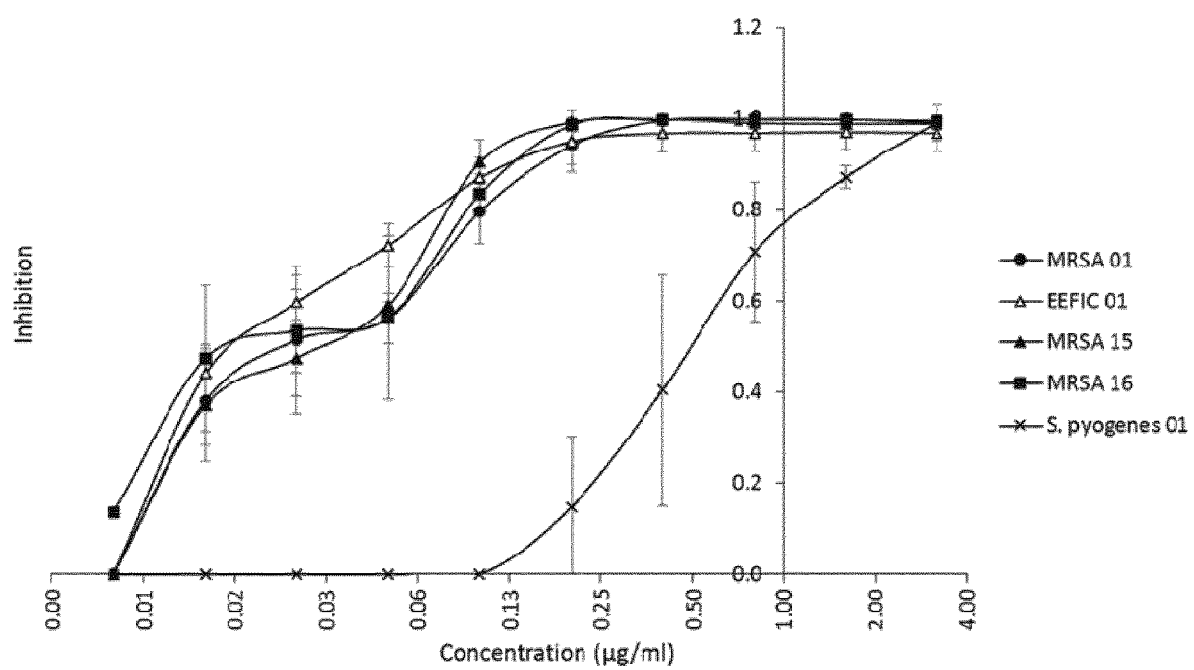
FIG. 1 shows microbiological data of niclosamide tested against MRSA, MSSA and S. pyogenes strains. The MIC of niclosamide was ≤0.4 µg/ml against S. aureus strains, including the strains resistant to fusidic acid (*) and the strains resistant to mupirocin (+), and ≤3.2 µg/ml against Streptococcus pyogenes strains.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Definitions

In the context of the present application and invention, the following definitions apply:

The term "*Staphylococcus aureus*" or "*S. aureus*" as used herein, without further description, relates to any strain of the gram-positive bacteria classified as *Staphylococcus aureus*, and which have been associated with a number of infections, including pneumonia, osteomyelitis, arthritis, endocarditis, sepsis and toxic shock syndrome, as well as cause less severe infections of the skin and soft tissues.

The term "methicillin-resistant *Staphylococcus aureus*" or "MRSA" as used herein includes strains of *Staphylococcus aureus* that are resistant to methicillin and can also broadly relate to Gram-positive bacteria strains (e.g. beta-lactamase-producing bacteria) that are resistant to antibiotics falling within the general classification of penicillins. Methicillin is the common name for (2S,5R,6R)-6-[(2,6-dimethoxybenzoyl)amino]-3,3-dimethyl-7-oxo-4-thia-1-azabi-cyclo[3.2.0]heptane-2-carboxylic acid, which is a narrow spectrum beta-lactam antibiotic that has been used to treat infections caused by susceptible Gram-positive bacteria (e.g. including *Staphylococcus aureus*).

Reference to "a halogenated salicylanilide" is unless stated otherwise intended to include any of the halogenated salicylanilides disclosed herein including closantel, rafoxanide, oxyclozanide and niclosamide and derivatives thereof including salts, hydrates and esters thereof. For example, a halogenated salicylanilide selected from the group consisting of closantel, rafoxanide, oxyclozanide and niclosamide or a pharmaceutically acceptable salt thereof, and particularly niclosamide. Unless specifically stated otherwise herein reference to a halogenated salicylanilide, for example selected from the group consisting of closantel, rafoxanide, oxyclozanide and niclosamide or a pharmaceutically acceptable salt thereof, is intended to encompass hydrates of the halogenated salicylanilide as well as hydrates of salts of the halogenated salicylanilide.

The term "pharmaceutically acceptable salt" refers to salts that retain the biological effectiveness and properties of the compounds described herein and, which are not biologically or otherwise undesirable. Pharmaceutically acceptable salts are well known to skilled persons in the art. Particular salts include ethanolamine or piperazine salts. Accordingly, it may be that a reference to a salt of a halogenated salicylanilide herein may refer to a pharmaceutically acceptable salt of the halogenated salicylanilide.

The term "solvate" is used herein to refer to a complex of solute, such as a compound or salt of the compound, and a solvent. If the solvent is water, the solvate may be termed a hydrate, for example a monohydrate, dihydrate, trihydrate etc., depending on the number of water molecules present per molecule of substrate.

The term "halo" or "halogen" refers to one of the halogens, group 17 of the periodic table. In particular the term refers to fluorine, chlorine, bromine and iodine. Preferably, the term refers to fluorine or chlorine.

The term $C_m$-$C_n$ refers to a group with m to n carbon atoms.

The term "$C_1$-$C_6$-alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. "$C_1$-$C_4$-alkyl" similarly refers to such groups containing up to 4 carbon atoms. The alkyl groups may be unsubstituted or substituted by one or more substituents. Substituents for the alkyl group may be halogen, e.g. fluorine, chlorine, bromine and iodine, OH, $C_1$-$C_4$ alkoxy.

Reference to an "ester" of the halogenated salicylanilide refers to an ester (RC(O)O— or ROC(O)—) formed with an available hydroxy or carboxy group on the halogenated salicylanilide. For example an ester formed by the esterification of the 2-hydroxy group of the benzamide in a halogenated salicylanilide. The ester may be cleavable following topical application of the salicylanilide to provide the free hydroxy or carboxy group of the parent molecule thereby providing a prodrug of the halogenated salicylanilide. The ester may be for example a $C_{1-6}$-alkyl ester.

Reference to an "alkyl monohydroxy alcohol" refers to an alkyl alcohol which has one hydroxyl group, representative examples of alkyl monohydroxy alcohols include short chain alkyl monohydroxy alcohols, particularly $C_{1-6}$-monohydroxy alcohols such as methanol, ethanol, propanol and isopropanol.

Reference to an "alkanol amine" refers to an amine N-substituted by one, two or three alkyl alcohol moieties. Representative examples include ethanolamine, diethanolamine, triethanolamine, isopropanolamine and diisopropanolamine.

Reference to "PEG x00" herein means a polyethylene glycol with an average molecular weight of x00. For example PEG 400 refers to a PEG with an average molecular weight of 400. Unless stated otherwise reference herein to the molecular weight of polymer, such as a PEG is a reference to number average molecular weight (Mn) of the polymer. The number average molecular weight can be measured using well known methods, for example by gel permeation chromatography or 1H NMR end-group analysis. Such methods include GPC analysis as described in Guadalupe et al (*Handbook of Polymer Synthesis, Characterization, and Processing, First Edition*, 2013) and end group analysis described in e.g. Page et al *Anal. Chem.*, 1964, 36 (10), pp 1981-1985.

The halogenated salicylanilide may be applied topically in the form of a prodrug of the halogenated salicylanilide. As used herein, the term "prodrug" refers to covalently bonded moiety on the halogenated salicylanilide which modifies the biological and/or physical properties of the compound. The active halogenated salicylanilide is released following topical application of the prodrug compound composition of the invention. Prodrugs may be formed by, for example, modification of a suitable functional group in the parent compound, for example a carboxylic or hydroxy group may be modified to form an ester which is cleaved following topical application of the prodrug. Various prodrug strategies are known and are described in, for example, the following documents:

a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) *A Textbook of Drug Design and Development*, edited by Krogsgaard-Larsen
d) H. Bundgaard, Chapter 5 "Design and Application of Pro-drugs", by H. Bundgaard p. 113-191 (1991); and
e) H. Bundgaard, *Advanced Drug Delivery Reviews*, 8, 1-38 (1992).

Unless stated otherwise, reference herein to a "% by weight of a halogenated salicylanilide or a pharmaceutically acceptable salt thereof" is intended to refer to the amount of the free acid (i.e. non-salt form) salicylanilide. For example reference to a composition comprising "5% by weight of niclosamide or a pharmaceutically acceptable salt thereof" refers to a composition comprising 5% by weight of the niclosamide as the free acid. Accordingly, where such a composition comprises a salt of niclosamide, the absolute amount of the niclosamide salt in the composition will be higher than 5% by weight in view of the salt counter ion that will be also be present in the composition.

The term "gel" is used herein refers to a semi-solid, apparently homogeneous substance that may be elastic and jelly-like (as in gelatin). The gel comprises a three-dimensional polymeric or inorganic matrix within which is dispersed a liquid phase. The matrix of the gel comprises a network of physically or chemical cross-linked polymers or copolymers that swell but do not dissolve in the presence of a solvent (for example the low molecular weight PEG). The cross-linking within the gel matrix may be physical cross linking (for example by hydrogen bonding or ionic cross-linking) or may be covalently cross-linked. Generally in the non-aqueous gel compositions described herein the halogenated salicylanilide is dissolved in the PEG and the PEG/halogenated salicylanilide solution is dispersed within the polymeric cross-linked network of the gel. The gels are generally clear in appearance, however, turbid gels are also contemplated. Generally the gel-forming agent, for example gel-forming polymer is present in the gel in an amount of from about 0.5-15% by weight, typically 0.5-2% by weight. The U.S.P. defines gels as a semi-solid system consisting of dispersion made up of either small inorganic particles or large organic molecule enclosing and interpenetrated by liquid.

The compositions (for example the gel compositions) of the present invention are "non-aqueous" compositions, by which is meant that the composition is anhydrous and therefore substantially water free. For example the compositions disclosed herein including the gel compositions contain less than 5%, less than 1% or suitably less than 0.01%, preferably less than 0.001% by weight water. Preferably the compositions of the invention are anhydrous and contain no detectable water.

Protic organic solvents are those that are capable of hydrogen bonding. The most common examples of protic organic solvents include but are not limited to alcohols and carboxylic acids.

Aprotic organic solvents are those that are not capable of hydrogen bonding. Common aprotic organic solvents include but are not limited to ethers, dimethylformamide (DMF), dimethylsulfoxide (DMSO) and acetonitrile.

The partition coefficient is a ratio of concentrations of un-ionized compound between the two liquid phases. The logarithm of the ratio of the concentrations of the un-ionized solute (drug) in the solvents is called log P. When one of the solvents is water and the other is a non-polar solvent (usually octanol), then the log P value is known as a measure of lipophilicity.

The term "treatment" herein encompasses both therapeutic and prophylactic treatment, of either an infectious or a non-infectious condition, in a mammal such as a human or animal, but in particular a human. It may involve complete or partial eradication of the condition, removal or amelioration of associated symptoms, arresting subsequent development of the condition, and/or prevention of, or reduction of risk of, subsequent occurrence of the condition. Treatment includes, for example (i) the prevention of the disease caused by Gram-positive bacteria, for example *Staphylococcus aureus* and/or *Streptococcus pyogenes* and/or *Propionibacterium acnes* (ii) the suppression of the disease caused by bacteria, for example *Staphylococcus aureus* and/or *Streptococcus pyogenes* and/or *Propionibacterium acnes*; and (iii) the relief of the disease caused by bacteria, for example *Staphylococcus aureus* and/or *Streptococcus pyogenes* and/or *Propionibacterium acnes*; v) the eradication of a non-symptomatic colonization by *Staphylococcus aureus* from an area on the body, (v) the eradication of Gram-positive bacteria for example *Staphylococcus aureus* and/or *Streptococcus pyogenes* and/or *Propionibacterium acnes* symptomatic infection, (vi) the eradication of Gram-positive bacteria for example *Staphylococcus aureus* and/or *Streptococcus pyogenes* and/or *Propionibacterium acnes*; from an area of the body affected by another disease that could enable establishment of an infection more readily, than in a non-disease affected area—e.g. an area of the skin affected by eczema, atopic dermatitis or diabetic ulcer, (vii) the suppression of the disease caused by Gram-positive bacteria, for example *Staphylococcus aureus* and/or *Streptococcus pyogenes* and/or *Propionibacterium acnes*; from an area of the body affected by another non-infectious disease that enables establishment of an infection more readily, than in a non-disease affected area—e.g. an area of the skin affected by eczema or atopic dermatitis.

The bacterial strain causing an infection may be characterized by a spontaneous mutation frequency of less than $10^{-6}$, such as less than $10^{-7}$ or $10^{-8}$, such as less than $4\times10^{-9}$, for example less than $1\times10^{-9}$. The treatment will typically involve the use of the halogenated salicylanilides closantel, rafoxanide, oxyclozanide or niclosamide or derivatives thereof against Gram-positive bacteria such as *Staphylococcus aureus* and *Streptococcus pyogenes*. One example which is of special interest is niclosamide.

When a compound or salt described in this specification is administered to treat a disorder, a "therapeutically effective amount" is an amount sufficient to reduce or completely alleviate symptoms or other detrimental effects of the disorder; cure the disorder; reverse, completely stop, or slow the progress of the disorder; or reduce the risk of the disorder getting worse.

Reference to The "rate of resistance development", "mutation frequency" or "frequency of mutation" herein indicates the in vitro frequency at which detectable mutants arise in a bacterial population in the presence of a given antibiotic concentration. The frequency of mutation is calculated as the number of resistant colonies per inoculum after 48 hours incubation at 37° C. at a given antibiotic concentration. Unless stated otherwise the frequency of mutation stated herein is the mutation frequency calculated at the MIC×1 of the antibiotic. Mutation frequency may be determined using standard methods described in Drago et al. *The Journal of Antimicrobial Chemotherapy*, 56(2), (2005) 353-359). The rate of resistance development is quantified as the frequency of spontaneous mutants in a population of bacteria that is able to resist a given concentration of the antibiotic. For example the frequency of mutation may be $10^{-9}$ if on average 1 cell in $10^9$ cells is able to survive a concentration of antibiotic corresponding to 1×MIC.

The Minimum inhibitory concentration (MIC) is the lowest concentration of an antibacterial that will inhibit the visible growth of a microorganism after overnight incubation.

The median lethal dose, $LD_{50}$ (abbreviation for "lethal dose, 50%") refers to the dose of a substance required to kill half the members of a tested population after a specified test duration. $LD_{50}$ figures are frequently used as a general indicator of a substance's acute toxicity.

Therapeutic index (therapeutic ratio) is defined as the amount of a therapeutic agent causing the therapeutic effect measured as MIC to the amount that causes death in animal studies measured as $LD_{50}$.

Colony-forming unit (CFU) is an approximate estimate of the number of viable bacterial cells in a sample. Viable is defined as the ability of the cell to multiply via binary fission under the controlled conditions.

As used herein, the term "lesion" refers to, for example, pustules, papules, open and closed comedones and nodules. Inflammatory lesions include, but are not limited to, pustules, papules and nodules. Non-inflammatory lesions include, but are not limited to, open and closed comedones. One of skill in the art will recognize that the methods of the present invention are useful for treating other types of lesions of acne vulgaris.

A "topical medication" is a medication that is applied to body surfaces such as the skin or mucous membranes to treat. Topical medications differ from many other types of drugs because mishandling them can lead to certain complications in a patient or administrator of the drug. Suitably the non-aqueous gel compositions described herein are epicutaneous, meaning that they are applied directly to the skin. Topical medications may also be applied to the surface of tissues other than the skin, for example to the surface of a tooth, rectally or vaginally. Suitably the gel composition is topically applied epicutaneously.

Reference to the "composition of the invention" a "non-aqueous gel composition" of the invention or "gel composition" of the invention is intended to be a reference to any of the non-aqueous compositions described herein in the description, examples and claims unless stated otherwise.

Reference to "about" in the context of a numerical is intended to encompass the value +/−10%. For example about 20% includes the range of from 18% to 22%.

Non-Aqueous Compositions

In certain embodiments the non-aqueous topical composition of the invention comprises:
 (i) a halogenated salicylanilide selected from niclosamide, rafoxanide, oxyclozanide and closantel, or a pharmaceutically acceptable salt thereof; and
 (ii) polyethylene glycol (PEG) with a melting point of less than 40° C.;
with the proviso that when the composition comprises niclosamide or rafoxanide, or a pharmaceutically acceptable salt thereof, the composition further comprises a non-polymeric glycol (for example an alkylene glycol, e.g. a 02-8 alkylene glycol and especially propylene glycol).

In certain embodiments the non-aqueous composition comprises:
 (i) a halogenated salicylanilide (for example niclosamide, rafoxanide, oxyclozanide and closantel), or a pharmaceutically acceptable salt thereof; and
 (ii) greater than 60% by weight of a PEG, preferably wherein the average molecular weight of the PEG is 800 or less and particularly 600 or less. For example the average molecular weight of the PEG is less than 800. For example the average molecular weight of the PEG is less than 400.

In certain embodiments the non-aqueous topical composition of the invention comprises propylene glycol. Accordingly the composition of the invention may comprise:
 (i) a halogenated salicylanilide selected from niclosamide, rafoxanide, oxyclozanide and closantel, or a pharmaceutically acceptable salt thereof;
 (ii) polyethylene glycol (PEG) with a melting point of less than 40° C.; and
 (iii) propylene glycol.

In certain embodiments the non-aqueous topical composition of the invention comprises:
 (i) 0.1 to 5% by weight of a halogenated salicylanilide selected from niclosamide, rafoxanide, oxyclozanide and closantel, or a pharmaceutically acceptable salt thereof;
 (ii) polyethylene glycol (PEG) with a melting point of less than 40° C.; and
 (iii) 0.5 to 30% (for example 5 to 25%) by weight propylene glycol.

Examples of PEG, preferably with an average molecular weight of less than 600, which may be used in the non-aqueous composition are described in more detail below under the section "Polyethylene Glycol (PEG)"

It may be that the non-aqueous composition comprises up to 10%, up to 20%, up to 30%, up to 35%, up to 40%, up to 45%, up to 50% or up to 55% by weight of PEG. For example wherein the lower limit of PEG is 1% by weight and the upper limit is any of the values set out in this paragraph. For example wherein the lower limit of PEG is 5% by weight and the upper limit is any of the values set out in this paragraph.

In certain embodiments it has been found that a high concentration of PEG in the composition provides a non-aqueous topical compositions with advantageous properties, for example one or more of enhanced antibacterial activity, improved transdermal penetration and/or good tolerability when topically applied to the skin. Certain compositions described herein provide high concentration of the halogenated salicylanilide in skin tissues (e.g. the dermis and epidermis) and very low levels of systemic exposure (e.g. in the plasma) to the halogenated salicylanilide. The compositions are therefore expected to provide an effective local topical treatment of, for example, a dermal condition, with little or no systemic side-effects, because the systemic exposure is low. Such compositions are expected to provide a wide therapeutic window between the beneficial therapeutic effects and the onset of undesirable systemic side effects that may be associated with the halogenated salicylanilide. Such side effects could be systemic toxicity or undesirable systemic effects such as disruption to the gut microbiome which may result from systemic exposure to an antibacterial agent.

It may be that the non-aqueous composition comprises more than 65%, more than 70%, more than 75%, more than 80%, more than 85%, more than 90%, more than 95%, more than 96%, more than 97%, more than 98% or more than 99% PEG (preferably with an average molecular weight of 600 or less, less than 600 or 400 or less); and wherein the % is by weight of the composition. Further amount of the PEG which may be present in the composition are described under the section "Polyethylene Glycol (PEG)"

It may be that the halogenated salicylanilide, or a pharmaceutically acceptable salt thereof is present in the non-aqueous composition in an amount of 0.01% to 10%, for example from 0.01% to 5%, from 0.01% to 4.5%, from 0.01% to 4%, from 0.01% to 3.5%, from 0.01% to 3%, from 0.1% to 5%, from 0.1% to 4.5%, from 0.1% to 4%, from 0.1% to 3.5%, from 0.1 to 3%, from 0.1 to 2.5%, from 0.1 to 2%, from 0.1 to 1.5%, from 0.1 to 1%, or from 0.5 to 3%, for example about 1%, about 2% about 2.5% about 3%, about 4% or about 5%, wherein the % are by weight based upon the weight of the composition. Suitable examples of halogenated salicylanilides which may be used are described below.

It may be that the non-aqueous composition of the invention comprises:
(i) 0.01 to 3.5% (for example 0.1 to 3% or about 2%) by weight of a halogenated salicylanilide, or a pharmaceutically acceptable salt thereof; and
(ii) at least 70% (for example at least 90%) by weight of a PEG, wherein the average molecular weight of the PEG is 600 or less (for example less than 600 or from about 200 to about 600 or about 400).

It may be that the non-aqueous compositions described herein further comprise a polar organic solvent for example a polar organic solvent selected from an alkylene glycol (e.g. propylene glycol), 2-(2-ethoxyethoxy)ethanol, glycerol, a macrogol stearyl ether (e.g. macrogol 15 stearyl ether) or a macrogol isostearate or a fatty alcohol, for example a $C_{12}$-$C_{18}$-alcohol such as cetostearyl alcohol or a mixture two or more thereof. It may be that the polar organic is present in the composition in an amount of from about 5% to about 65%, about 10% to about 55% or about 25% to about 50% by weight of the composition.

It may be that the non-aqueous compositions described herein further comprise a glycol, for example an alkylene glycol (e.g. propylene glycol). It may be that the composition comprises from about 5% to about 30%, about 10% to about 30%, or about 14% to about 28% by weight of a glycol, particularly propylene glycol.

It may be that the non-aqueous compositions described herein further comprise 2-(2-ethoxyethoxy)ethanol. It may be that the composition comprises from about 1% to about 25%, about 5% to about 20% or about 10% to about 20% by weight of 2-(2-ethoxyethoxy)ethanol.

It may be that the non-aqueous compositions described herein further comprise glycerol. It may be that the composition comprises from about 5% to about 30%, about 10% to about 30%, or about 15% to 25% by weight of glycerol.

It may be that the composition comprises one or more non-polar excipients, for example one or more non-polar oils, hydrocarbon solvents or waxes. It may be that the composition comprises one or more non-polar excipients selected from aromatic or aliphatic esters, a mineral oil, a vegetable oil and long-chain or medium chain triglycerides. For example the non-polar excipients may be selected from one or more of a mineral oil, (e.g. liquid paraffin or a paraffin wax) and medium chain triglycerides. It may be that the non-polar excipients are present in the composition in an amount of from about 2% to about 50%, about 5% to about 40%, about 5% to about 30%, or about 5% to 25% by weight of the composition.

It may be that the non-aqueous compositions described herein further comprise one or more surfactant or emulsifiers, for example an ionic or non-ionic surfactant or emulsifiers. Representative examples of surfactants or emulsifiers include any of those described herein, for example a PEGylated fatty acid glyceride (labrasol), polyoxyethylene glycol sorbitan alkyl ester (polysorbate), a polyoxyethylene glycol alkyl ether (Brij), polyoxyethylene ethers of fatty alcohols (ceteareth), or a fatty acid ester of glycerol (e.g. glyceryl stearate). It may be that the surfactant or emulsifiers are present in the composition in an amount of from about 0.1% to about 15%, about 0.2% to about 10%, or about 0.2% to about 5% by weight of the composition.

In certain embodiments the non-aqueous composition comprises a non-aqueous emulsion or microemulsion. Non-aqueous emulsion or microemulsion compositions are particularly suitable for providing compositions in the form of a non-aqueous topical cream composition. The non-aqueous emulsion comprise a non-aqueous hydrophilic phase (suitably comprising polar excipients) and a non-aqueous hydrophobic phase which is immiscible with the hydrophilic phase (suitably comprising non-polar excipients such as an oil). It may be that the hydrophilic phase comprises the continuous phase of the emulsion and the hydrophobic phase is dispersed within the hydrophilic phase as the discontinuous phase of the emulsion. In certain embodiments the non-aqueous hydrophobic phase comprises the continuous phase of the emulsion and the non-aqueous phase is dispersed within the non-aqueous hydrophobic phase as the discontinuous phase of the emulsion.

Generally the non-aqueous hydrophilic phase comprise the halogenated salicylanilide, the PEG and optionally one or more of the polar solvents described herein. Accordingly it may be that the non-aqueous hydrophilic phase comprises niclosamide, PEG and optionally one or more polar solvents selected from propylene glycol, 2-(2-ethoxyethoxy)ethanol, glycerol, a macrogol stearyl ether (e.g. macrogol 15 stearyl ether) and a fatty alcohol, for example a $C_{12}$-$C_{18}$-alcohol such as cetostearyl alcohol.

It may be that the non-aqueous hydrophobic phase of the emulsion or microemulsion comprises one or more of the non-polar excipients described herein, for example, a mineral oil, a vegetable oil and long-chain or medium chain triglycerides.

In those embodiments where the composition is in the form of a non-aqueous emulsion or microemulsion the composition suitably comprises a surfactant or emulsifier, for example one or more of the surfactants or emulsifiers described herein.

Suitably the non-aqueous composition comprises a solution of the halogenated salicylanilide. Accordingly it is preferred that the halogenated salicylanilide is completely dissolved in the non-aqueous composition. However, it is contemplated that the halogenated salicylanilide may present as a dispersion in the composition. Alternatively in some embodiments at least a proportion of the halogenated salicylanilide is dissolved in the composition. In this embodiment it is preferred that at least 80%, preferably at least 90%, more preferably at least 95% by weight of the halogenated salicylanilide is dissolved in the composition.

Non-Aqueous Gel Compositions

In certain embodiments the non-aqueous topical composition of the invention is in the form of a non-aqueous topical gel composition In certain embodiments there is provided a non-aqueous topical gel composition comprising:
(i) a halogenated salicylanilide (for example selected from niclosamide, rafoxanide, oxyclozanide and closantel), or a pharmaceutically acceptable salt thereof; and
(ii) PEG with a melting point of less than 40° C.; and
(iii) a gel forming agent.

In certain embodiments there is provided a non-aqueous topical gel composition comprising:

(i) a halogenated salicylanilide (for example selected from niclosamide, rafoxanide, oxyclozanide and closantel), or a pharmaceutically acceptable salt thereof;

(ii) greater than 60% by weight of a PEG, preferably wherein the average molecular weight of the PEG is less than 600; and (iii) a gel-forming agent.

Particular aspects of the non-aqueous gel compositions of the invention are described below.

Gel-Forming Agent

It may be that the gel-forming agent present in the compositions disclosed herein is an inorganic gel-forming agent. It may be that the gel-forming agent is a gel-forming polymer.

Inorganic Gel Forming Agents

It may be that the gel-forming agent is an inorganic gel-forming agent, for example a bentonite or a silica. It may be that the gel-forming agent is magnesium aluminium silicate (Veegum®).

Gel-Forming Polymers

The gel-forming agent may be a gel-forming polymer. The gel-forming polymer may be a hydrophilic gel-forming polymer. The gel-forming polymer may be selected from the group consisting of: gelatin; agar; agarose; pectin; carrageenan; chitosan; alginate; starch; starch components (e.g. amylose or amylopectin); tragacanth gum; xanthan gum; gum Arabic (acacia gum); guar gum; gellan gum; locust bean gum; polyurethane; polyether polyurethane; cellulose; cellulose ethers (for example methylcellulose, carboxymethyl cellulose, ethylcellulose, hydroxyethyl cellulose or hydroxypropyl cellulose), cellulose esters, cellulose acetates, cellulose triacetates; cross-bonded polyvinyl alcohol; polymers and copolymers of acrylic acid, hydroxyalkyl acrylates, hydroxyethyl acrylate, diethylene glycol monoacrylate, 2-hydroxypropylacrylate or 3-hydroxypropyl acrylate; carbomers (cross-linked poly(acrylic acids), for example carbomer 910, 934P, 940GE, 941GE, 971P, 974P; polymers and copolymers of methacrylic acid, hydroxyethyl methacrylate, diethyleneglycol monomethacrylate, 2-hydroxypropyl methacrylate, 3-hydroxypropyl methacrylate or dipropylene glycol monomethylacrylate; vinylpyrrolidone polymers; polymers and copolymers or acrylamide, N-methylacrylamide, N-propylacrylamide; methacrylamide, N-isopropylmethacrylamide, or N-2-hydroxyethylmethacrylamide; poloxamers (triblock copolymers comprising a central polyoxypropylene block flanked by two polyoxyethylene blocks, for example a Pluronic®); and gels comprising cross-linked polyalkylene glycols, for example gels comprising cross-linked polyethylene glycol or cross-linked polypropylene glycol. In specific embodiments binary or tertiary etc combinations of any of the above gel-forming agents are foreseen. When the gel forming agent comprises a PEG, the PEG is suitably a higher molecular weight than the PEG used as a solvent to dissolve or disperse the halogenated salicylanilide in the gel composition. Accordingly it is to be understood that when the gel-forming agent is a PEG, the PEG of the gel-forming agent is different to the PEG present in component (ii) of the compositions of the invention. For example, where the gel forming agent comprises a PEG, the PEG suitably has a molecular weight greater than 600, for example greater than 1000, greater than 10000 or greater than 20000. Suitably, when the gel forming agent comprises a PEG it has an average molecular weight of from about 600 to about 35,000, for example from about 800 to about 25,000, or from about 1000 to about 20,000.

Other gel-forming agents are also contemplated, for example as disclosed in Gels handbook Vols 1-4, Osada et al. 2001 Elsevier.

The gel-forming polymer may be a gum, for example a gum selected from tragacanth gum, xanthan gum; gum arabic (acacia gum); guar gum; gellan gum locust bean gum.

The gel-forming polymer may be a cellulose ether, for example methylcellulose, carboxymethyl cellulose, ethylcellulose, hydroxyethyl cellulose, hydroxy propyl methyl cellulose or hydroxypropyl cellulose.

Carbomer Gel-Forming Polymers

In a particular embodiment the gel-forming agent is a carbomer. Carbomers are high molecular weight cross-linked poly(acrylic acid) polymers. The polymers may be cross-linked by polyalcohol allyl ethers, for example, allyl sucrose or allyl pentaerythritol The carbomer may be a homopolymer, for example 910, 934P, 940GE, 941GE, 971P, 974P, wherein "GE" refers to medical grade and "P" oral grade. Derivatives of Carbomer polymers may also be used, for example Carbopol interpolymers comprising a carbomer polymer comprising a block copolymer of polyethylene glycol and a long chain alkyl acid ester, such derivatives are commercially available as ETD 2020 NF and Ultrez 10 NF from Lubrizol.

Carbomers (also known as Carbopols) are well known and are characterised in the United States Pharmacopeia/National Formulary (USP/NF) monograph for Carbomers and the European Pharmacopeia (Ph. Eur.) monograph for Carbomers, reference to which is incorporated herein.

The carbomer may have a viscosity of from about 4,000 to about 70,000, for example about 10,000 to about 60,000, for about 20,000 to about 50,000, about 25,000 to about 45,000 or about 29,400 to about 39,400 cP, wherein the viscosity is that of a 0.5 wt % solution of the carbomer in water, neutralised to pH 7.3-7.8 at 25° C., measured using a Brookfield RVT, 20 rpm, spindle #6.

Suitably the carbomer comprises from about 56% to about 68.0% by weight carboxylic acid (—COOH) groups, measured by titrating an aqueous solution or dispersion of the polymer against NaOH.

Suitably the carbomer is substantially free of residual benzene (for example containing less than 0.5 parts per million). Accordingly, it is preferred that the carbomer is prepared without using benzene as a solvent during the polymerisation process. Preferred carbomers are those are prepared using ethyl acetate and optionally cyclohexane as the solvent during polymerisation.

A particular carbomer for use as a gelling agent in the present invention is Carbomer 974P. This carbomer suitably has a viscosity of 29400 to 39400 cP (0.5% solution in water neutralized to pH 7.3-7.8 and measured at 25° C. using a Brookfield RVT, 20 rpm with spindle #6). The carbomer typically has a carboxylic acid content of from 56 to 68%.

Conventionally carbomer gels are formed by dispersing the carbomer in water, which results in ionisation of the carboxy groups present in the polymer. The resulting solution or dispersion is then neutralised using a base, resulting in an increase in viscosity and gel formation. However, in the present invention the gel is a non-aqueous gel and gel formation may be achieved by dissolving or dispersing the carbopol in the organic solvent together with the halogenated salicylanilides and heating the mixture to about 70° C.

The gel-forming polymer may also be referred to as a colloid i.e. a colloid system wherein the colloid particles are disperse in the organic solvent and the quantity of solvent available allows for the formation of a gel. In embodiments it is preferred to use reversible colloids preferably thermoreversible colloids (e.g. agar, agarose and gelatin etc.) as opposed to irreversible (single-state) colloids. Thermo-reversible colloids can exist in a gel and sol state, and alternate between states with the addition or elimination of heat. Thermoreversible colloids which may be used according to the invention, whether individually or in combination, include for example, gelatin, carrageenan, gelatin, agar, agarose (a polysaccharide obtained from agar), pectin and cellulose derivatives for example methylcellulose, carboxymethyl cellulose, ethylcellulose, hydroxyethyl cellulose, hydroxy propyl methyl cellulose or hydroxypropyl cellulose. Another term which may be applied to gel forming polymers is "thermotropic": a thermotropic gelling agent is one caused to gel by a change in temperature. In embodiments of the invention, therefore, the gel former is a thermotropic gel-forming polymer or a combination of such polymers.

The gel-forming polymer may be or comprise a ionotropic gel-forming polymer whose gelling is induced by ions. Suitable ionotrophic gel-forming agents are anionic or cationic polymers which can be cross-linked by multivalent counter ions to form a gel. The ionotrophic gel-forming polymers may be, for example chitosan, an alginate, carrageenan or pectin.

The gel-forming polymer may comprise or be a single polymer of a mixture of two or more polymers, for example a combination of two or more of the gel-forming polymers listed herein.

The amount of gel forming agent present in the composition should be selected so as to provide a gel composition having the required rheological properties, for example viscosity for topical application. Generally the gel will be of a viscosity such that it can be readily dispensed and spread over and rubbed in the area of, for example, skin that is infected. The rheology of the gel composition will depend upon the particular gelling agent used, the molecular weight of the PEG, the particular halogenated salicylanilide and the amounts thereof in the composition. Generally the gelling agent, for example a carbomer, will be present in the gel composition is an amount of up to about 10% by weight, for example up to about 1%, 2%, 3%, 4%, 5%, 5.5%, 6%, 6.5%, 7%, 7.5%, 8%, 8.5%. 9% or 9.5% by weight of the gel composition. Suitably the gelling agent, for example a carbomer, may be present in an amount of from about 0.01% to about 10% by weight of the gel composition, for example about 0.01% to about 8%, about 0.05% to about 7%, about 0.05% to about 6%, about 0.05% to about 5%, about 0.05% to about 4%, about 1% to about 6%, about 1% to about 5% or about 1% to about 4%, about 2% to about 5%, about 2% to about 4% or about 2% to about 3%, wherein the % is by weight based on the weight of the gel composition.

Polyethylene Glycol (PEG)

As illustrated in the Examples, the inventors have found that when polyethylene glycol (PEG) is used as a solvent in the non-aqueous gel composition, the antibacterial effect of the halogenated salicylanilide, for example niclosamide, is enhanced compared to the use of PEG alone or the halogenated salicylanilide alone when tested in a mouse model.

Suitably the PEG is liquid at ambient temperature (for example 20 to 25° C.), accordingly the solvent may be a low molecular weight PEG. Particularly, the PEG has an average molecular weight of 600 or less, suitably less than about 600. For example the PEG may have an average molecular weight of from about 200 to about 600, about 200 to about 500 or about 200 to about 400. A particular PEG is selected from PEG 200, PEG 300 and PEG 400. In one particular embodiment the PEG is PEG 400.

Suitably the PEG is present in an amount at least sufficient to provide a solution of the halogenated salicylanilide in the non-aqueous composition. As will be realised the amount of PEG required to dissolve the halogenated salicylanilide will depend upon the particular halogenated salicylanilide used and the other components of the composition. In certain embodiments the PEG is present in the non-aqueous composition of the invention an amount of at least 60%, suitably greater than 60% by weight of the composition. Non-aqueous compositions containing high amounts of PEG provide topical compositions which give high levels of the halogenated salicylanilide in skin tissues and only minimal systemic exposure to the halogenated salicylanilide. Such compositions have also been found to be well tolerated, despite containing high PEG concentrations. Suitably the PEG is present in an amount of greater than 60%, 65%, 70%, 75%, 80%, 85%, 90%, 91%, 92%, 93%, 94%, 95%, 96%, 97% 98% or 99% wherein the % is by weight based upon the weight of the gel composition. It may be that the PEG, preferably a PEG with an average molecular weight of 600 or less (particularly less than 600) is present in the non-aqueous composition of the invention in an amount of for example 65 to 98%, for example from 65% to 95%, 65% to 90%, 65% to 80%, 70% to 98%, 70% to 95%, 70% to 85%, 70% to 80%, 80% to 98%, 80% to 95%, 80% to 90%, 85% to 98% or 85% to 95%, wherein the % is by weight based upon the weight of the non-aqueous composition of the invention.

In certain embodiments the non-aqueous compositions comprise lower concentrations of PEG, for example 50% or less, 45% or less, 40% or less, 35% or less, 30% or less, 25% or less, 20% or less, 15% or less, wherein the % is % by weight of the composition. It may be that the PEG is present from about 1% to about 50%, from about 5% to about 40%, from about 5% to about 35%, or from about 5 to about 30% by weight of the composition.

Halogenated Salicylanilide

Salicylanilides are also known as 2-hydroxy-N-phenyl-benzamides or 2-hydroxybenzanilides. Salicylanilides are weakly acidic phenolic compounds. Halogenated salicylanilides are salicylanilides substituted by at least one halo group. The halogenated salicylanilide may be any halogenated salicylanilide possessing antibacterial activity against Gram-positive bacteria.

It may be that the halogenated salicylanilide is any of the niclosamide analogues described in WO 2008/021088, which are incorporated herein by reference thereto.

The halogenated salicylanilide may be a halogenated salicylanilide of the formula (I):

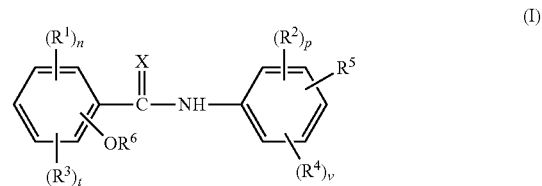

(I)

wherein
X is O or S;
R$^1$ and R$^2$ are at each occurrence independently selected from halo;
R$^3$ and R$^4$ are at each occurrence independently selected from H, C$_{1-6}$-alkyl, —OR$^{A1}$, —NO$_2$ and —CN;
R$^5$ is H or -L$^1$-R$^7$;

$R^6$ is H or —C(O)$R^{A2}$;
$R^5$ is -$L^1$-$R^7$;
$L^1$ is selected from a bond, O, S, or —(C$R^{A3}R^B$)$_o$—, wherein o is 1 or 2;
$R^7$ is phenyl, unsubstituted or substituted with 1, 2, or 3 groups selected from halo, $C_{1-4}$-alkyl, —O$R^{A4}$, —NO$_2$ and —CN;
$R^{A1}$, $R^{A2}$, $R^{A3}$ and $R^{A4}$ are at each occurrence independently selected from H and $C_{1-4}$-alkyl;
$R^B$ is at each occurrence selected from H, $C_{1-4}$-alkyl and —CN;
n and p are each independently selected from 0, 1, 2, 3 or 4, with the proviso that n+p is at least 1;
t and v are independently selected from 0, 1 and 2;
or a pharmaceutically acceptable salt, solvate (e.g. hydrate) or ester thereof.

The halogenated salicylanilide of formula (I) may be of the formula (II), or a pharmaceutically acceptable salt, solvate (e.g. hydrate) or ester thereof.

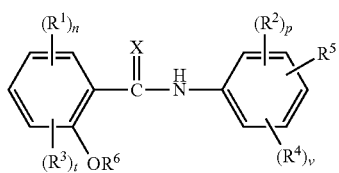

(II)

The following statements in the numbered paragraphs below apply to compounds of the formulae (I) or (II). These statements are independent and interchangeable. In other words, any of the features described in any one of the following statements may (where chemically allowable) be combined with the features described in one or more other statements below. In particular, where a compound is exemplified or illustrated in this specification, any two or more of the statements below which describe a feature of that compound, expressed at any level of generality, may be combined so as to represent subject matter which is contemplated as forming part of the disclosure of this invention in this specification.
1. X is O.
2. $R^1$ and $R^2$ are at each occurrence independently selected from fluoro, chloro, bromo and iodo.
3. $R^1$ and $R^2$ are at each occurrence independently selected from chloro, bromo and iodo.
4. $R^1$ is chloro.
5. $R^1$ is bromo.
6. $R^1$ is iodo.
7. $R^2$ is chloro.
8. $R^2$ is bromo.
9. $R^2$ is iodo.
10. $R^3$ and $R^4$ are at each occurrence independently selected from H, $C_{1-4}$-alkyl, —O$R^{A1}$, —NO$_2$ and —CN.
11. $R^3$ and $R^4$ are at each occurrence independently selected from H, $C_{1-4}$-alkyl, —O$R^{A1}$ and —NO$_2$.
12. $R^3$ and $R^4$ are at each occurrence independently selected from H, $C_{1-4}$-alkyl, —OH, —OMe, —NO$_2$ and —CN, for example H, $C_{1-4}$-alkyl, —OH or —NO$_2$.
13. $R^5$ is H.
14. $R^5$ is -$L^1$-$R^7$.
15. $L^1$ is selected from —O—, —CH$_2$— and —CH(CN)—, for example —O— or —CH(CN)—.
16. $R^7$ is phenyl, unsubstituted or substituted with 1, 2, or 3 groups selected from halo, $C_{1-4}$-alkyl and —CN
17. $R^7$ is phenyl unsubstituted or substituted with 1, 2, or 3 groups (for example 1 or 2 groups) selected from halo.
18. $R^7$ is unsubstituted phenyl.
19. $L^1$ is selected from —O— and —CH(CN)—; and $R^7$ is phenyl unsubstituted or substituted with 1, 2, or 3 groups selected from halo.
20. $R^6$ is H.
21. $R^6$ is —C(O)$R^{A2}$, for example —C(O)CH$_3$.
22. t=0 or 1.
23. t=0.
24. v=0 or 1.
25. v=0.
26. o is 1.
27. v=1 and $R^4$ is selected from —OH, $C_{1-4}$-alkyl and —NO$_2$.
28. A compound of any of formulae (I) or (II), or a pharmaceutically acceptable salt thereof.

Particular compounds are compounds of formula (I) or formula (II), or a pharmaceutically acceptable salt, solvate or ester thereof wherein:
X is O;
$R^1$ and $R^2$ are at each occurrence independently selected from halo;
$R^3$ and $R^4$ are at each occurrence independently selected from H, $C_{1-4}$ alkyl, —O$R^{A1}$, —NO$_2$ and CN;
$R^5$ is H or -$L^1$-$R^7$;
$R^6$ is H or —C(O)$R^{A2}$;
$L^1$ is selected from O and —CH(CN)—;
$R^7$ is phenyl unsubstituted or substituted with 1, 2, or 3 groups selected from halo;
$R^{A1}$ and $R^{A2}$ are at each occurrence independently selected from H and $C_{1-4}$-alkyl;
n and p are each independently selected from 0, 1, 2, 3 or 4, with the proviso that n+p is at least 1;
t and v are independently selected from 0, 1 and 2;
or a pharmaceutically acceptable salt, or ester thereof.

It may be that the halogenated salicylanilide is selected from:

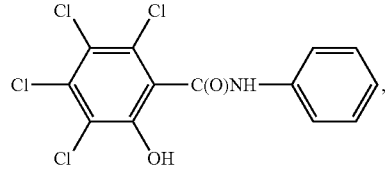

tetrachlorosalicylanilide

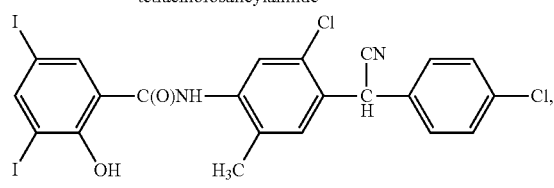

Closantel

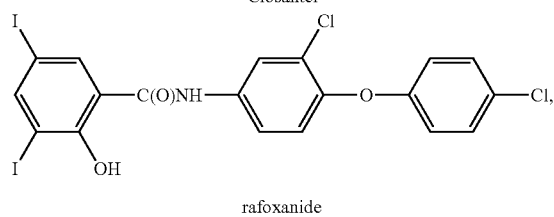

rafoxanide

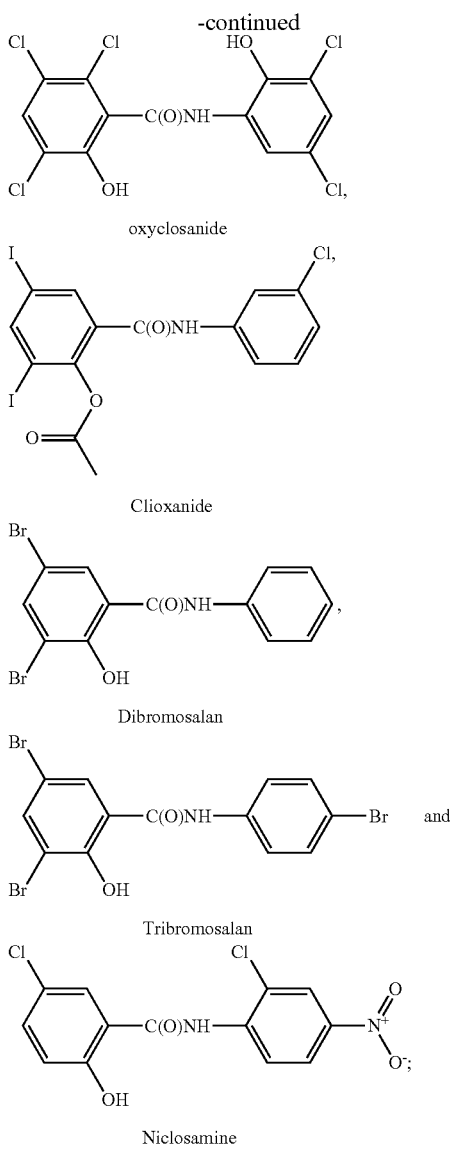

or a pharmaceutically acceptable salt, solvate, prodrug or derivative thereof.

The halogenated salicylanilide may be a thioamide derivative, for example brotianide:

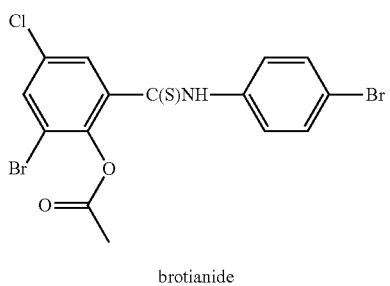

or a pharmaceutically acceptable salt, solvate, prodrug or derivative thereof.

The halogenated salicylanilide may be selected from the group consisting of tetrachlorosalicylanilide, closantel, rafoxanide, oxyclozanide, resorantel, clioxanide, dibromosalan, tribromosalan, brotianide and niclosamide, or a pharmaceutically acceptable salt or prodrug or derivative thereof.

The halogenated salicylanilide may be selected from the group consisting of tetrachlorosalicylanilide, closantel, rafoxanide, oxyclozanide, resorantel, dibromosalan, tribromosalan and niclosamide, or a pharmaceutically acceptable salt or ester thereof.

The halogenated salicylanilide may be selected from the group consisting of clioxanide, closantel, oxyclozanide, rafoxanide, tribromosalan or a pharmaceutically acceptable salt or ester thereof.

The halogenated salicylanilide may be selected from the group consisting of tetrachlorosalicylanilide, closantel, rafoxanide, oxyclozanide, resorantel, clioxanide, dibromosalan, tribromosalan, brotianide and niclosamide, or a pharmaceutically acceptable salt thereof.

The halogenated salicylanilide may be selected from the group consisting of tetrachlorosalicylanilide, closantel, rafoxanide, oxyclozanide, resorantel, clioxanide, dibromosalan, tribromosalan and niclosamide, or a pharmaceutically acceptable salt thereof.

The halogenated salicylanilide may be selected from the group consisting of niclosamide, clioxanide, closantel, oxyclozanide, rafoxanide and tribromosalan, or a pharmaceutically acceptable salt thereof.

The halogenated salicylanilide may be selected from the group consisting of clioxanide, closantel, oxyclozanide, rafoxanide and tribromosalan, or a pharmaceutically acceptable salt thereof.

The halogenated salicylanilide may be selected from the group consisting of clioxanide, closantel, rafoxanide and tribromosalan, or a pharmaceutically acceptable salt thereof.

The halogenated salicylanilide may be selected from the group consisting of tetrachlorosalicylanilide, closantel, rafoxanide, oxyclozanide, resorantel, clioxanide, dibromosalan, tribromosalan, brotianide and niclosamide.

The halogenated salicylanilide may be selected from the group consisting of niclosamide, closantel, oxyclozanide and rafoxanide, or a pharmaceutically acceptable salt thereof.

The halogenated salicylanilide may be clioxanide, or a pharmaceutically acceptable salt or ester thereof, for example the halogenated salicylanilide is clioxanide or a pharmaceutically acceptable salt thereof, suitably the halogenated salicylanilide is clioxanide.

The halogenated salicylanilide may be closantel, or a pharmaceutically acceptable salt or ester thereof, for example the halogenated salicylanilide is closantel or a pharmaceutically acceptable salt thereof, suitably the halogenated salicylanilide is closantel.

The halogenated salicylanilide may be oxyclozanide, or a pharmaceutically acceptable salt or ester thereof, for example the halogenated salicylanilide is oxyclozanide or a pharmaceutically acceptable salt thereof, suitably the halogenated salicylanilide is oxyclozanide.

The halogenated salicylanilide may be rafoxanide, or a pharmaceutically acceptable salt or ester thereof, for example the halogenated salicylanilide is rafoxanide or a pharmaceutically acceptable salt thereof, suitably the halogenated salicylanilide is rafoxanide.

The halogenated salicylanilide may be tribromosalan, or a pharmaceutically acceptable salt or ester thereof, for example the halogenated salicylanilide is tribromosalan or a pharmaceutically acceptable salt thereof, suitably particularly the halogenated salicylanilide is tribromosalan.

The halogenated salicylanilide may be niclosamide, or a pharmaceutically acceptable salt or ester thereof, for example the halogenated salicylanilide is niclosamide or a pharmaceutically acceptable salt thereof.

In certain embodiments the halogenated salicylanilide is niclosamide in the free acid form.

In certain embodiments the halogenated salicylanilide is a pharmaceutically acceptable salt of niclosamide, for example an ethanolamine salt, or piperazine salt.

The halogenated salicylanilide may be a hydrate of niclosamide or pharmaceutically acceptable salt thereof. However, generally it is preferred that the niclosamide is not present in the gel composition as a hydrate. Accordingly it is preferred that the niclosamide is anhydrous niclosamide, or a pharmaceutically acceptable salt thereof. In a particular embodiment the niclosamide is anhydrous niclosamide.

Suitably the halogenated salicylanilides is present in the non-aqueous composition in an amount of up to 10%, up to 8%, up to 6%, up to 5% up to 4.5%, up to 4%, up to 3.5%, up to 3% or up to 2%, wherein the % is by weight based upon the weight of the composition.

The halogenated salicylanilides may, for example, be present in the non-aqueous composition in an amount of from about 0.01% to about 6%, about 0.01% to about 5.5%, about 0.01% to about 5%, about 0.01% to about 4.5%, about 0.01% to about 4%, about 0.01% to about 3.5%, about 0.01% to about 3%. about 0.01% to about 2.5%, about 0.05 to about 5%, about 0.05% to about 4.5%, 0.05% to about 4%, 0.05% to about 3.5%, 0.05% to about 3%, 0.05% to about 2.5%, about 0.1% to about 6%, about 0.1% to about 5%, about 0.1% to about 4.5%, about 0.1% to about 4%, about 0.1% to about 3.5%, about 0.1% to about 3%, about 0.1% to about 2.5%, about 0.5% to about 5%, about 0.5% to about 4.5%, about 0.5% to about 4%, about 0.5% to about 3.5%, about 0.5% to about 3%, or about 0.5% to about 2.5%, wherein the % is by weight based upon the weight of the composition. For example, the halogenated salicylanilides may is present in the composition in an amount of about 0.5%, about 1%, about 1.5%, about 2%, about 2.5%, about 3% about 3.5%, about 4%, about 4.5% or about 5%, wherein the % is by weight based upon the weight of the composition.

The halogenated salicylanilides may be present in the composition as a solution or a suspension. However, as discussed above it is preferred that the halogenated salicylanilide is substantially or fully dissolved in the composition of the invention. A solution of the halogenated salicylanilide in the composition is generally preferred because this maximises the drug available for absorption following topical administration of the composition and is expected to reduce inter and intra-patient variability in absorption. Accordingly, in preferred embodiments the amount of halogenated salicylanilide is selected such that it is fully dissolved in the composition.

Specific Non-Aqueous Gel Compositions

In an embodiment the non-aqueous gel composition comprises:
 (i) 0.05% to 5% by weight of a halogenated salicylanilide, for example closantel, niclosamide, rafoxanide or oxyclozanide, or a pharmaceutically acceptable salt thereof;
 (ii) more than 60% by weight of PEG, wherein the PEG has an average molecular weight of less than 600; and
 (ii) up to 10% by weight of a gel-forming polymer.

Suitably in this embodiment the halogenated salicylanilide, for example niclosamide, is present in the composition in an amount of from 0.05% to 4.5%, for example from 0.5% to 3% by weight of the gel composition.

Suitably in this embodiment the gel-forming polymer may be present in an amount of 0.5% to 5% by weight, for example from about 1% to about 3%, or from about 2% to about 3% by weight. The gel-forming polymer may be any of the gel-forming polymers described herein, for example a carbomer polymer such as carbomer 974P.

In another embodiment the non-aqueous gel composition comprises or consists of:
 (i) a halogenated salicylanilide, for example closantel, niclosamide, rafoxanide or oxyclozanide, or a pharmaceutically acceptable salt thereof;
 (ii) more than 70% by weight of a PEG, wherein the average molecular weight of the PEG is less than 600; and
 (iii) a gel-forming agent.

In this embodiment the halogenated salicylanilide, for example niclosamide may be present in the composition in an amount of from 0.05 to 5% by weight, for example, 0.05% to 4.5% by weight of the gel composition.

In this embodiment the gel forming agent may be any of the gel-forming agents described herein, for example a gel-forming agent selected from the group consisting of: gelatin; agar; agarose; pectin; carrageenan; chitosan; alginate; starch; starch components (e.g. amylose or amylopectin); tragacanth gum; xanthan gum; gum Arabic (acacia gum); guar gum; gellan gum; locust bean gum; polyurethane; polyether polyurethane; cellulose; cellulose ethers (for example methylcellulose, carboxymethyl cellulose, ethylcellulose, hydroxyethyl cellulose or hydroxypropyl cellulose), cellulose esters, cellulose acetates, cellulose triacetates; cross-bonded polyvinyl alcohol; polymers and copolymers of acrylic acid, hydroxyalkyl acrylates, hydroxyethyl acrylate, diethylene glycol monoacrylate, 2-hydroxypropylacrylate, 3-hydroxypropyl acrylate, carbomers (cross-linked poly(acrylic acids), for example carbomer 910, 934P, 940GE, 941GE, 971P, 974P; polymers and copolymers of methacrylic acid, hydroxyethyl methacrylate, diethyleneglycol monomethacrylate, 2-hydroxypropyl methacrylate, 3-hydroxypropyl methacrylate, dipropylene glycol monomethylacrylate; vinylpyrrolidone polymers; acrylamide polymers and copolymers, N-methylacrylamide, N-propylacrylamide; methacrylamide polymers and copolymers, N-isopropylmethacrylamide, N-2-hydroxyethylmethacrylamide; poloxamers (triblock copolymers comprising a central polyoxypropylene block flanked by two polyoxyethylene blocks, for example a Pluronic®); and combinations thereof.

In this embodiment the gel-forming agent is suitably present in an amount of u to 10%, for example from 0.25% to 10% by weight of the gel composition, for example from 0.5% to 5%, or from 0.5% to 4%, or from 1% to 3% by weight of the composition.

In this embodiment the PEG may be a PEG with an average molecular weight of from about 200 to about 500, such as PEG 200, PEG 300 or PEG 400. Particularly the PEG is PEG 400. Suitably the PEG is present in an amount of more than 70%, for example more than 75%, 80%, 85%, 90% or 95% by weight based upon the weight of the gel composition.

In an embodiment the non-aqueous gel composition comprises or consists of:
 (i) 0.05 to 4.5% by weight of a halogenated salicylanilide, for example closantel, niclosamide, rafoxanide or oxyclozanide, or a pharmaceutically acceptable salt thereof;

(ii) more than 60% by weight of a PEG, wherein the average molecular weight of the PEG is less than 600; and (ii) up to 5% by weight of a carbomer (for example a carbomer selected from carbomer 910, carbomer 934P, carbomer 940GE, carbomer 941GE, carbomer 971P and carbomer 974P).

In this embodiment the non-aqueous gel composition suitably comprises from 0.1% to 5%, for example from 0.1% to 4%, 0.5% to 4%, 1% to 4%, 1% to 3% or from 2 to 3% of the carbomer (for example carbomer 974P).

In this embodiment the PEG may be a PEG with an average molecular weight of from about 200 to about 500, such as PEG 200, PEG 300 or PEG 400. Particularly the PEG is PEG 400. Suitably the PEG is present in an amount of more than 70%, for example more than 75%, 80%, 85% or 90% by weight based upon the weight of the gel composition.

In an embodiment the non-aqueous gel composition comprises or consists of:
(i) 1 to 3% by weight of niclosamide, or a pharmaceutically acceptable salt thereof;
(ii) 94 to 98% by weight of a PEG, wherein the average molecular weight of the PEG is less than 600 (for example an average molecular weight of from about 200 to about 500, such as PEG 200, PEG 300 or PEG 400); and
(iii) 1 to 3% by weight of a carbomer (for example a carbomer selected from carbomer 910, carbomer 934P, carbomer 940GE, carbomer 941GE, carbomer 971P and carbomer 974P).

In an embodiment the non-aqueous gel composition comprises or consists of:
(i) 1 to 3% by weight of niclosamide, or a pharmaceutically acceptable salt thereof;
(ii) 94 to 98% by weight of PEG 400; and
(ii) 1 to 3% by weight of carbomer 974P.

Optionally in all of the specific gel compositions described above, when the halogenated salicylanilide is niclosamide, the niclosamide may be present in the composition as the free acid.

Optionally in all of the specific gel compositions described above the gel composition suitably does not comprise ethanol. Accordingly such gel compositions are non-aqueous, non-ethanolic gel compositions.

Local pH

The inventors have found that the antibacterial activity of halogenated salicylanilides, e.g. niclosamide, is higher at low pH than at neutral or basic pH.

Accordingly it may be that the composition of the invention provides a local pH of less than 6 at the site of infection Thus, it may be that the composition does not comprise a buffer or pH modifier. Halogenated salicylanilides are weakly acidic by virtue of their phenolic groups. Thus, it may be that the halogenated salicylanilide, e.g. niclosamide, is in the free acid form (i.e. not in the form of a salt). In other embodiments the composition comprises excipients to provide a local pH of less than 6 when the formulation is topically applied, for example the composition may comprise pH modifier such as a suitable acid or base. The components of the formulation may be selected such that it provides a local pH of greater than 4.5 (e.g. greater than 5) at the site of infection. For example the composition may provide a local pH of from about 4.5 to 6, suitably about 5.5. Reference to a "local pH" is to the pH at the site where the formulation is applied for example the pH on the surface of the skin after applying the composition comprising the halogenated salicylanilide. Non-aqueous gel compositions of the invention wherein the gel forming agent comprises acidic moieties, for example carbomer polymers, may be particularly suitable to provide the desired low local pH following topical application without the need for additional agents to modify the pH.

The local pH following topical application, for example on the surface of the skin may be measured using known techniques, for example The pH of the skin surface can be measured using standard methods, for example using a suitable with a flat glass electrode attached to a pH meter. Such apparatus are commercially available as for example, the Skin-pH-Meter PH 905 (Courage+Khazaka electronic GmbH). Methods for measuring local skin pH are well known and include the ISO standard ISO 12505-1:2014(en), section 4.4, incorporated herein by reference thereto.

The desired local pH of less than 6 at the site of infection, for example on the skin surface, can be obtained by routine methods, for example by adding a suitable acidic or basic material to the formulation comprising the halogenated salicylanilide. For example, an inorganic or organic acid, base or buffer may be added to the formulation comprising the halogenated salicylanilide in a sufficient amount to provide the desired local pH of less than 6 at the site of infection.

Optional Components

The following components and features may optionally be present in the non-aqueous compositions of the invention, for example the non-aqueous gel compositions described herein.

Additional Solvent

The non-aqueous composition of the invention may comprise one or more additional non-aqueous solvent(s) in addition to the PEG. The presence of a further solvent may enhance the solubility of the halogenated salicylanilide and or help maintain the halogenated salicylanilide in solution during the preparation, storage and topical use of the non-aqueous composition. The additional solvent may be, for example, a polar organic solvent in which the halogenated salicylanilide is soluble, for example a polar organic solvent wherein the halogenated salicylanilides has a solubility of greater than 2% by weight in the additional solvent.

The polar organic solvent may be a protic polar organic solvent. In one embodiment the solvent is a protic polar organic solvent having a dielectric constant of from about 10 to about 45, for example a dielectric constant of from about 10 to about 25. Particular polar protic organic solvents are those which have a dielectric constant of from about 10 to about 20, wherein in each case the dielectric constant is measured at 20-25° C. The dielectric constant of organic solvents is well known or can be measured using well-known techniques Representative protic polar organic solvents with a dielectric constant in the range of 10 to 45 include those set out in Table 1:

TABLE 1

| Solvent | Dielectric Constant at 20-25° C. |
|---|---|
| 2-methylpentane-2,4-diol (pinakon) | 7.4 |
| PEG 300 | 18.0 |
| PEG 400 | 14.1-12.4 |
| PEG 600 | 12.7 |
| N-octanol | 10.3 |
| Propylene glycol | 32 |
| Glycerol | 42.5 |
| Methanol | 33 |

TABLE 1-continued

| Solvent | Dielectric Constant at 20-25° C. |
|---|---|
| Ethanol | 24.3 |
| Propanol | 22 |

Further polar organic solvents with a dielectric constant in the range are well known (see for example "Solubility and Solubilization in Aqueous Media" By Samuel H. Yalkowsky (University of Arizona). Oxford University Press: New York. 1999). For example, the polar organic solvent may be selected from ethyl acetate, dimethylformamide, dichloromethane, glycerol, propylene glycol, or 2-(2-ethoxyethoxy)ethanol (Transcutol), propylene glycol stearyl ether, propylene glycol isostearate.

In another embodiment the polar organic solvent is an aprotic polar organic solvent having a dielectric constant of from about 10 to about 45, for example a dielectric constant of from about 10 to about 25 at 25° C.

When present the additional solvent(s) is suitably present in an amount of up to 35% by weight of the composition. For example, up to 30%, 25%, 20% 15% or 10% by weight of the composition. In particular embodiments the additional solvent(s) is present in an amount of less than 10%, for example less than 8%, less than 6%, less than 5% or less than 3%, wherein the % is by weight based upon the weight of the non-aqueous composition. It may be that the additional solvent is present in an amount of 1% to 30%, from 1% to 25%, from 1% to 20%, from 1 to 10%, from 3 to 30%, from 3 to 20%, from 3 to 15%, from 5 to 30%, from, 5 to 20% or from 5 to 10%, wherein the % is by weight based upon the weight of the composition.

In some embodiments it is preferred that the non-aqueous composition of the invention does not contain an additional solvent, because the presence of another solvent with the PEG may increase the risk of undesirable precipitation of the halogenated salicylanilide when the gel composition is applied to the skin as a result of for example differential rates of solvent absorption and/or evaporation following application of the non-aqueous composition. Accordingly in may be that the non-aqueous composition of the PEG as the only solvent for the halogenated salicylanilide.

Non-Ethanolic Compositions

The presence of ethanol in topical compositions can cause dryness and/or peeling of the skin, particularly in patients with sensitive skin. This can be a particular problem in patients with acne, because the dryness resulting from the ethanol can promote excess oil production in the skin and exacerbation of the acne (R I Ceilley, Skinmed., 9(1), 2011, 15-21). Accordingly, it is preferred that non-aqueous compositions of the invention are ethanol free. This is particularly the case when the non-aqueous composition is for use in the topical treatment of acne. Thus in a preferred embodiment the composition of the invention is a non-aqueous, non-ethanol (ethanol free) composition, for example a non-aqueous, non-ethanol gel composition.

Absorption Enhancers

The non-aqueous composition may optionally comprise an absorption enhancer. The absorption may be any substance which acts to enhance the permeation of the halogenated salicylanilide into the epidermis and epidermis. Suitable absorption enhancers include the transdermal absorption enhancers disclosed in for example Smith and Maibach (2005) *Percutaneous Penetration Enhancers*, Second Edition ISBN 9780849321528, incorporated herein by reference.

It may be that the absorption enhancer, when present in the non-aqueous composition is selected from, for example, a sulfoxide (for example dimethylsulfoxide); dimethylacetamide; dimethylformamide; a urea; a fatty alcohol, for example a $C_8$-$C_{18}$ fatty alcohol, which may be saturated or unsaturated (for example caprylic alcohol or cetostearyl alcohol); a polyol (for example glycerol; a glycol (for example propylene glycol or hexylene glycol); Azone ((1-dodecylazacycloheptan-2-one); an essential oil (for example a terpene or terpenoid); a pyrrolidone (for example N-methyl-2-pyrrolidone); an oxazolidinone (for example 4-decyloxazolidin-2-one) a surfactant (for example a non-ionic, anionic or cationic surfactant, particularly a non-ionic surfactant for example a polyoxyethylene glycol sorbitan alkyl ester (for example polysorbates such as Polysorbate 80 ((polyoxyethylene (20) sorbitan monooleate), Polysorbate 60 (polyoxyethylene (20) sorbitan monostearate), Polysorbate 40 (polyoxyethylene (20) sorbitan monopalmitate) or Polysorbate 20 (polyoxyethylene (20) sorbitan monolaurate)), a polyoxyethylene glycol alkyl ether (e.g. Brij, such as Brij S721 or Brij S2), a poloxamer or a PEGylated fatty acid glyceride such as caprylocaproyl polyoxyl-8 glycerides (e.g. Labrasol), a fatty acid ester of glycerol, for example glyceryl stearate, or polyoxyethylene ethers of fatty alcohols (for example cetyl alcohol and/or stearyl alcohol, particular examples include ceteareth-15, -16, -17, -18, -19, -20, -21, -22, 23-, -24, or -25 and particularly ceteareth-20), a polyethoxylated sorbitan fatty acid ester, for example. The absorption enhancer may also be 2-(2-ethoxyethoxy)ethanol (Transcutol). Preferred absorption enhancers are those which have a minimal impact on the structure of the skin so as to minimise undesirable tolerability effects associated with the absorption enhancer, for example irritation, which could exacerbate the effects of a skin infection in a patient. Particular absorption enhancers include polyols, for example propylene glycol or glycerol. Accordingly the absorption enhancer may be propylene glycol. The absorption enhancer may be glycerol. It is to be understood that where the absorption enhancer may also act as an additional solvent in the composition, particularly when the halogenated salicylanilide is soluble in the absorption enhancer.

When present in the non-aqueous composition, the absorption enhancer may be in an amount of up to 35% by weight of the composition (e.g. a gel composition), for example from 0.5% to 35%, from 1% to 35%, from 5% to 30%, from 10% to 30%, from 5% to 35%, from 5% to 30% or from 10% to 30%, wherein the % is by weight of the composition.

As illustrated in the examples herein it was found that when a non-aqueous gel composition comprising a carbomer gelling agent (carbomer 974P) and PEG 400, the presence of an propylene glycol as an absorption enhancer did not significantly affect permeation and absorption of the halogenated salicylanilide tested (niclosamide) on human skin. Accordingly, in certain embodiments the non-aqueous composition of the invention does not comprise an absorption enhancer. This may be advantageous, because it minimises the number of components present in the composition and may reduce the risk of undesirable side-effects associated with the absorption enhancer, for example skin irritation at the site of application of the non-aqueous composition. Non-aqueous compositions which do not contain an absorption enhancer may therefore exhibit improved tolerability.

Other Ingredients

The non-aqueous compositions described herein are topical compositions. Accordingly the composition is suitably in the form of a topical non-aqueous liquid, lotion, ointment, cream or gel suitable for topical application to, for example the skin. The non-aqueous composition will generally further comprise one or more additional excipients in addition to the halogenated salicylanilide and the PEG so as to provide compositions of the required form for topical administration. The additional components of the composition may be any of those described herein and/or one or more excipients selected from viscosity modifying agents, emulsifiers, surfactants, humectants, oils, waxes, additional solvents, preservatives, pH modifying agents (for example a suitable acid or base, for example an organic acid or organic amine base), buffers, antioxidants (for example butylated hydroxyanisol or butylated hydroxytoluene), crystallisation inhibitors (for example a cellulose derivative such as hydroxypropylmethyl cellulose), colorants, fragrances. Representative examples of such additional excipients are well known, for example as listed in the *Handbook of Pharmaceutical Excipients, 7th Edition, Rowe et al. Further more specific excipients are set out in any of the non-aqueous compositions described in the Examples herein.*

Manufacture

The gel compositions of the invention may be prepared by a process comprising the steps:
(i) dissolving the halogenated salicylanilide in the PEG;
(ii) combining the solution from step (i) with the gel-forming agent to form a mixture; and
(iii) causing the mixture to gel.

Suitably the halogenated salicylanilide is completely dissolved in the PEG in step (i) to form a solution. Dissolution may be aided by agitation of the mixture by stirring or by the application ultrasound. Optionally the mixture may be heated to facilitate dissolution. However, preferably the solution is prepared at ambient temperature. Optionally any halogenated salicylanilide that remains undissolved may be removed by a suitable filtration or other separation method prior to combining the solution with the gel-forming agent in step (ii) of the process.

The solution from step (i) may be added to the gel-forming agent or, alternatively, the gel-forming agent may be added to the solution. Optionally the gel-forming agent may be dissolved in some of the PEG to form a solution or dispersion prior to combining it with the solution from step (i). Suitably any additional optional components of the gel-composition, such as absorption enhancers, additional solvents etc. are added to the mixture prior to gelation of the composition. Alternatively one or more of the optional components can be added after gel formation by mixing the additional component(s) with the gel.

Gel formation in step (iii) may be affected by various methods, depending on the nature of the gel-forming agent used. For example where the gel-forming agent is thermotropic, the gel forming agent may be heated to form a liquid prior to adding the solution from step (i). Following mixing of the gel-forming agent with the solution, the resulting mixture may be cooled thereby causing the mixture to gel. Alternatively, where gelling is effected by ionic cross-linking, a suitable ionic agent is added to the mixture in step (iii), for example a suitable salt to thereby cause the mixture to gel. Gelling may also be induced by changing the pH of the mixture using a suitable acid or base to achieve the required pH for gelling to occur. The process is suitably carried out using anhydrous reagents under anhydrous conditions to ensure that the resulting gel composition is a non-aqueous gel composition.

When the gel-forming agent is a carbomer, a particular process for the preparation of the gel composition of the invention comprises:

(i) dissolving the halogenated salicylanilide in the PEG;
(ii) combining the solution from step (i) with a carbomer to form a mixture; and
(iii) heating the mixture to form a gel.

Step (i) of this process is suitably performed at room temperature. After combining the solution with the carbomer the mixture is mixed to provide a uniform dispersion. Mixing can be performed using any suitable method, for example stirring or, preferably, by homogenisation. The resulting dispersion is suitably de-gassed prior to gel formation in step (iii).

In step (iii) the mixture is heated to a temperature of 60 to 80° C., for example at about 70° C., preferably under agitation. Suitably the mixture is held at this temperature for a sufficient time to form a homogenous and transparent dispersion and gel formation. Typically a holding time of about 30 minutes is sufficient to enable solvation of the carbomer and gel formation.

The halogenated salicylanilide may be any of those described herein, for example niclosamide or a pharmaceutically acceptable salt thereof. The halogenated salicylanilide may be present in the final gel composition in an amount as described herein, for example of from about 0.05% to about 4.5% by weight of the final gel composition.

The carbomer in this process may be any of the carbomers disclosed herein, for example carbomer 974P. The carbomer may be present may be present in the final gel composition in an amount as described herein, for example in an amount of from amount of from about 0.5% to about 4% or about 2% to about 3% by weight of the final gel composition.

As described herein, the PEG suitably has an average molecular weight of 600 or less (suitably less than 600). For example a PEG with an average molecular weight of from 200 to 500, for example PEG 400. The PEG may be present in the final gel composition in an amount as described herein, for example greater than 80%, optionally greater than 85%, for example greater than 90% by weight of the final gel composition.

As discussed in relation to the general process method above, the process is performed under anhydrous conditions using anhydrous reagents to ensure that the resulting gel composition is a non-aqueous gel.

A further aspect of the present invention provides a non-aqueous gel composition obtained by, or obtainable by the process described herein.

When the composition of the invention is in the form of a lotion, ointment or cream the composition may be prepared using known methods for the preparation of such compositions. For example lotion or ointments may be prepared by simply blending the halogenated salicylanilide, the PEG and other excipients required, for example viscosity modifiers, additional solvents or surfactants.

The non-aqueous compositions of the invention may also be prepared as non-aqueous emulsion or microemulsions to provide a composition in the form of, for example a non-aqueous cream. Non-aqueous emulsions and microemulsions may be prepared using well known methods. Non-aqueous emulsions and microemulsions may be prepared by mixing two immiscible non-aqueous phases. Suitably a non-aqueous hydrophilic phase (for example a hydrophilic phase comprising polar excipients and the halogenated salicylanilide) is emulsified with an immiscible hydrophobic phase (e.g. comprising non-polar hydrophobic excipients). The non-aqueous emulsion may comprise a continuous hydrophobic phase and a discontinuous hydrophilic phase. Generally however the non-aqueous emulsion will comprise a continuous hydrophilic phase and a discontinuous hydrophobic phase. It may be that the non-aqueous hydrophilic phase comprises the halogenated salicylanilide and PEG and the non-aqueous hydrophobic phase comprises a non-polar liquid, which is immiscible with the hydrophobic phase, for example a medium chain triglyceride, a vegetable oil, a hydrocarbon oil or a mineral oil such as a paraffin. Generally the non-aqueous emulsion will be stabilised by one or more suitable surfactants or emulsifiers, for example one or more non-ionic surfactants (e.g. macrogol cetostearyl, cetostearyl alcohol, glyceryl stearate, polysorbate 80, Brij s721, Brij S2, ceteareth-20 or macrogol stearyl ether). The emulsion or micro emulsion may be formed using well-known methods, for example by homogenisation of the hydrophilic phase with the hydrophobic phase together with the other components of the non-aqueous emulsion or microemulsion.

The processes described herein are suitably carried out under anhydrous conditions using anhydrous excipients to prevent or minimise contamination of the composition with water.

Topical Applications of the Non-Aqueous Composition for Use in the Treatment of Gram-Positive Infections The inventors have found that halogenated salicylanilides, for example, closantel, rafoxanide, oxyclozanide, or niclosamide are highly effective against Gram-positive bacteria, such as *Staphylococcus aureus, Streptococcus pyogenes* or *Propionibacterium acnes*.

Figure 2:
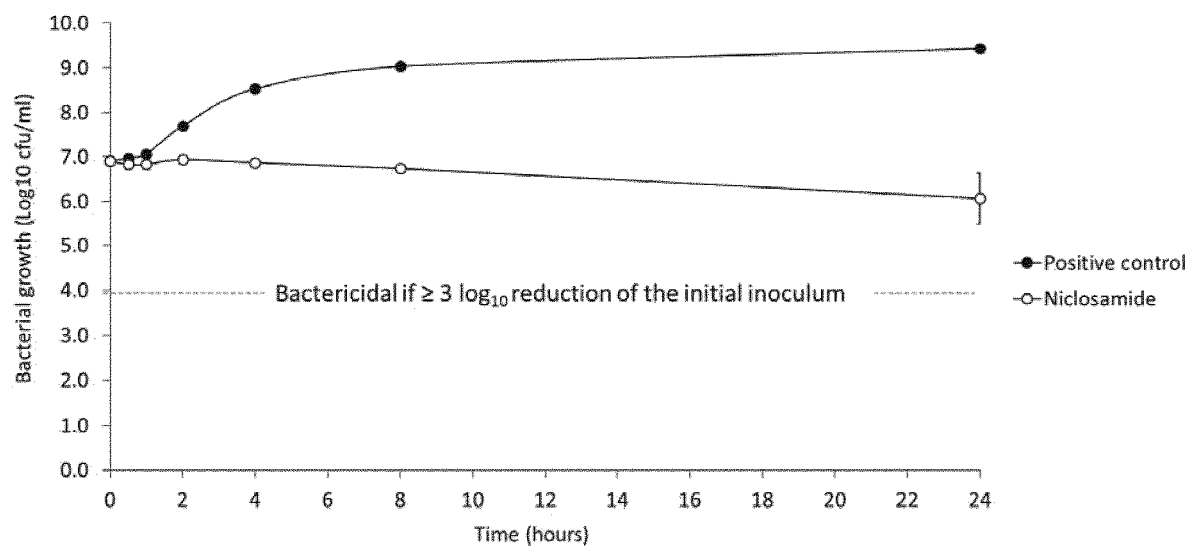
FIG. 2 shows a time-kill curve of MRSA 01 incubated with niclosamide (MIC×10). Niclosamide had a bacteriostatic effect against MRSA 01 under the tested conditions (initial inoculum: 7 $\log_{10}$ cfu/ml; niclosamide: 4 µg/ml [MIC×10]).

Niclosamide is bacteriostatic for *S. aureus* (See FIG. 1), i.e. it prevents growth of the bacterium, but does not kill it. The inventors have also found that niclosamide is equally effective against *S. aureus* strains resistant to methicillin, fusidic acid and mupirocin as it is against non-resistant strains (See FIG. 2).

Unexpectedly the inventors have also found that Gram-positive bacteria develop spontaneous mutations which confer resistance to the halogenated salicylanilide at very low frequencies. The Examples herein illustrate that halogenated salicylanilides, for example closantel, rafoxanide, oxyclozanide and particularly niclosamide, result in very low frequencies of resistance conferring mutations against MRSA 01 compared to the mutation frequencies observed with other commonly used antibacterial agents such as fusidic acid, mupirocin and retapamulin (see Table 5).

Accordingly the compositions of the invention comprising a halogenated salicylanilide are expected to provide a potent antibacterial effect, with a relatively low risk of bacterial resistance to the halogenated salicylanilide emerging. The composition of the invention comprising the halogenated salicylanilide may therefore be topically applied for prolonged treatment periods (for example more than 2 weeks) with a low risk of resistance developing.

In an embodiment there is provided a composition of the invention for use in the topical prevention and/or treatment of diseases or infections caused by Gram-positive bacteria.

It may be that the composition of the invention is for use in the topical prevention and/or treatment of a disease or condition selected from impetigo, bacterial conjunctivitis, atopic dermatitis related infections, sycosis barbae, superficial folliculitis, paronychia erythrasma, secondary infected dermatoses, carbuncles, furonculosis, ecthyma, cellulitis, erysipelas, necrotising fasciitis, secondary skin infections of wounds, dermatitis, scabies, diabetic ulcer, acne and the like. The infection or disease may be acne. The infection or disease may be atopic dermatitis or eczema infected by a Gram-positive bacteria, such as *Staphylococcus aureus, Streptococcus pyogenes*.

It may be that the composition of the invention is for use in the topical prevention and/or treatment of a disease or condition selected from skin or membrane disorders, such as infections of the skin or membranes (e.g. infections of nasal membranes, axilla, groin, perineum, rectum, dermatitic skin, skin ulcers, and sites of insertion of medical equipment such as i.v. needles, catheters and tracheostomy or feeding tubes) with any of the bacteria described above, (e.g. any of the Staphylococci, Streptococci such as *S. aureus* (e.g. methicillin resistant *S. aureus* (MRSA)). Particular bacterial conditions that may be treated by topical application of the gel composition of the invention also include the skin- and membrane-related conditions disclosed hereinbefore, as well as: rosacea (including erythematotelangiectatic rosacea, papulopustular rosacea, phymatous rosacea and ocular rosacea); erysipelas; erythrasma; ecthyma; ecthyma gangrenosum; impetigo; paronychia; cellulitis; folliculitis (including hot tub folliculitis); furunculosis; carbunculosis; staphylococcal scalded skin syndrome; surgical scarlet fever; streptococcal perianal disease; streptococcal toxic shock syndrome; pitted keratolysis; trichomycosis axillaris; pyoderma; external canal ear infections; green nail syndrome; spirochetes; necrotizing fasciitis; Mycobacterial skin infections (such as lupus vulgaris, scrofuloderma, warty tuberculosis, tuberculides, erythema nodosum, erythema induratum, cutaneous manifestations of tuberculoid leprosy or lepromatous leprosy, erythema nodosum leprosum, cutaneous *M. kansasii, M. malmoense, M. szulgai, M. simiae, M. gordonae, M. haemophilum, M. avium, M. intracellular, M. chelonae* (including *M. abscessus*) or *M. fortuitum* infections, swimming pool (or fish tank) granuloma, lymphadenitis and Buruli ulcer (Bairnsdale ulcer, Searles' ulcer, Kakerifu ulcer or Toro ulcer)); as well as infected eczema, burns, abrasions and skin wounds.

It may be that the infection or disease is selected from the group consisting of impetigo, bacterial conjunctivitis and atopic dermatitis. It may be that the infection or disease is selected from the group consisting of impetigo, bacterial conjunctivitis, atopic dermatitis related infections, sycosis barbae, superficial folliculitis, paronychia erythrasma, secondary infected dermatoses, carbuncles and furonculosis, ecthyma, cellulitis, erysipelas, necrotising fasciitis, secondary skin infections of wounds, dermatitis, scabies, diabetic ulcers and the like. It may be that the infection or disease is selected from atopic dermatitis and related infections, dermatitis, secondary infected dermatoses and impetigo. It may be that the infection or disease is cellulitis. It may be that the infection or disease is selected from sycosis barbae, superficial folliculitis, paronychia erythrasma, carbuncles, furonculosis, ecthyma, erysipelas, necrotising fasciitis, secondary skin infections of wounds, scabies and diabetic ulcers.

Examples of diseases which may be topically treated using the composition of the invention include impetigo, bacterial conjunctivitis, atopic dermatitis related infections, acne, sycosis barbae, superficial folliculitis, paronychia erythrasma, secondary infected dermatoses, carbuncles, furonculosis (ecthyma, cellulitis, erysipelas, necrotising fasciitis, secondary skin infections of wounds, dermatitis, scabies, diabetic ulcers and the like).

The infection or disease treated topically using the composition of the invention may be a skin infection, infected dermatitis or infected dermatosis, for example any of the skin infections described herein. The skin infection may, for example, be selected from impetigo (including impetigo contagiosa, bullous impetigo, and ecthyma) infected dermatitis (for example infected atopic dermatitis) infected eczema, infected skin wounds, infected burns and infected ulcers (for example diabetic ulcers).

The infection or disease treated topically using the composition of the invention may be a secondarily Gram-positive infected dermatosis, for example a secondary skin infection. Secondary Gram-positive infections are common complications of primary dermatoses, primary nonbacterial skin infections, traumatic lesions, ulcers, cutaneous infestations, and other skin diseases. Accordingly, the composition of the invention may be for use in the topical treatment of for example secondary infections of a condition selected from eczema, pediculosis, scabies, insect bites (for example papular urticaria), psoriasis (including pemphigus psoriasis), skin ulcers, kerion and a viral infection of the skin (for example herpes simplex or chicken pox).

In may be that the composition of the invention is for use in the treatment of a disease or infection selected from infected eczema, infected dermatitis, impetigo, infected diabetic ulcers, infected insect bites, infected burns, infected wounds, acne, rosacea, folliculitis, prosthetic joint infections and rhinosinusitis (including chronic rhinosinusitis).

In patients affected with a certain dermatological conditions the integrity of the skin tissue is often compromised making it easier for bacterial to penetrate the skin and become established. Such patients are therefore more prone to develop skin infections. Accordingly, the compositions of the invention may be for use in reducing or eradicating Gram-positive bacteria such as *Staphylococcus aureus* and/or *Streptococcus pyogenes* colonizing and proliferate in skin affected with a dermatological condition. The dermatological condition may be any of the conditions disclosed herein, for example dermatitis, including atopic dermatitis, eczema and diabetic ulcers. In some patients with dermatological conditions infected with a Gram-positive bacteria the infection may be non-symptomatic. However the infection could become symptomatic and/or result in a worsening or exacerbation of the dermatological condition. Accordingly the compositions of the invention may be useful as a prophylactic treatment of a dermatological condition to prevent an infection becoming symptomatic and/or to prevent or reduce the risk of exacerbation of the dermatological condition.

Gram-Positive Bacteria

It may be that the Gram-positive bacteria is methicillin-resistant *Staphylococcus aureus* (MRSA).

It may be that the Gram-positive bacteria develops spontaneous mutations which confer resistance to the halogenated salicylanilide at a frequency of less than $10^{-6}$ at the minimum inhibitory concentration (MIC) of the halogenated salicylanilide to the Gram-positive bacteria. It may be that the Gram-positive bacteria develops spontaneous mutations which confer resistance to the halogenated salicylanilide at a frequency of less than $10^{-7}$ at the MIC of the halogenated salicylanilide to the Gram-positive bacteria. It may be that the Gram-positive bacteria develops spontaneous mutations which confer resistance to the halogenated salicylanilide at a frequency of less than $10^{-8}$ at the MIC of the halogenated salicylanilide to the Gram-positive bacteria. Thus, it may be that the Gram-positive bacteria develops spontaneous mutations which confer resistance to the halogenated salicylanilide (for example niclosamide) at a frequency of less than $4 \times 10^{-9}$ at the MIC of the halogenated salicylanilide to the Gram-positive bacteria.

It may be that the Gram-positive bacteria is a *Staphylococcus* spp., *Streptococcus* spp. or *Propionibacterium* spp. The Gram-positive bacteria may be a *Staphylococcus* spp. or *Streptococcus* spp. The Gram-positive bacteria may be selected from *Staphylococcus aureus* or *Streptococcus pyogenes*. The Gram-positive bacteria may be *Propionibacterium* spp., for example *Propionibacterium acnes*. It may be that the Gram-positive bacteria is not a propionibacteria e.g. that it is not *Propionibacterium acnes*.

In some embodiments, the population of Gram-positive bacteria includes coccus Gram-positive bacteria. In some embodiments, the Gram-positive bacteria are from the *Streptococcus* or *Staphylococcus* genus.

In some embodiments, the Gram-positive bacteria are from the *Streptococcus* genus. It may be that the Gram-positive bacteria are *Streptococcus* selected from *Streptococcus pneumoniae*, *Streptococcus pyogenes*, *Streptococcus suis*, *Streptococcus agalactiae* or *Streptococcus viridans*.

In some embodiments, the Gram-positive bacteria are *Streptococcus pyogenes*

In some embodiments, the Gram-positive bacteria are from the *Staphylococcus* genus. It may be that the Gram-positive bacteria are *Staphylococcus* selected from *Staphylococcus epidermidis*, *Staphylococcus aureus*, *Staphylococcus saprophyticus* or *Staphylococcus lugdunensis*. In some embodiments, the coccus Gram-positive bacteria are *Staphylococcus aureus* (e.g. methicillin-resistant *Staphylococcus aureus*).

It may be that the population of Gram-positive bacteria includes antibiotic-resistant Gram-positive bacteria. It may be that the Gram-positive bacteria is an antibiotic resistant strain. For example, the Gram-positive bacteria described herein may be resistant to an antibiotic other than a halogenated salicylanilide (for example the bacteria is resistance to a drug other than closantel, rafoxanide, oxyclozanide or niclosamide, or a pharmaceutically acceptable salt or solvate thereof).

It may be that the Gram-positive bacteria is resistant to a drug selected from fusidic acid, mupirocin, retapamulin, erythromycin, clindamycin and a tetracycline (for example tetracycline, minocycline or doxycycline).

It may be that the Gram-positive bacteria is resistant to a drug selected from erythromycin, clindamycin or a tetracycline (for example tetracycline, minocycline or doxycycline).

It may be that the Gram-positive bacteria is resistant to a drug selected from fusidic acid, mupirocin and retapamulin.

It may be that the bacteria is resistant to a drug selected from fusidic acid, mupirocin, retapamulin, erythromycin and clindamycin.

It may be that the bacteria is resistant to a drug selected from erythromycin and clindamycin.

It may be that the bacteria is resistant to a tetracycline, for example tetracycline, minocycline or doxycycline.

It may be that the bacteria is *Propionibacterium* spp, for example *Propionibacterium acnes* resistant to a drug selected from erythromycin, clindamycin or a tetracycline (for example tetracycline, minocycline or doxycycline). It may be that the bacteria is *Propionibacterium* spp, for example *Propionibacterium acnes* resistant to a drug selected from erythromycin and clindamycin. It may be that the bacteria is *Propionibacterium* spp, for example *Propionibacterium acnes* resistant to a drug selected from fusidic acid or retapamulin.

It may be that the bacteria is methicillin-resistant *Staphylococcus aureus* (MRSA).

It may be that the Gram-positive bacteria is not an antibiotic resistant strain.

The low mutation frequency associated with the halogenated salicylanilides may enable the halogenated salicylanilide comprised in the gel composition of the invention to be topically applied as a monotherapy in the prevention or treatment of an infection. This has the advantage that it reduces the exposure of patients to unnecessary additional therapeutic agents and in particular avoids the need to co-administer additional antibiotics, thereby further reducing the risk of resistance associated with the use of conventional antibiotics.

The halogenated salicylanilide may be applied topically to provide a treatment of an infection, by for example reducing or eliminating the Gram-positive bacteria causing the infection. The low mutation frequencies associated with the halogenated salicylanilides may also make the compounds particularly suitable for use as a maintenance therapy to maintain an infection in remission; to prevent recurrence of the infection; or to control the concentration of Gram-positive bacteria at an acceptably low level to prevent or minimise symptoms of the infection experienced by a subject.

Atopic Dermatitis

In a particular embodiment there is provided a non-aqueous composition of the invention for use in the topical treatment of atopic dermatitis.

Patients with atopic dermatitis are prone to skin infection by Gram-positive bacteria such as *Staphylococcus* and/or *Streptococcus* bacteria and there is a correlation of severity of the atopic dermatitis with bacterial colonisation.

In certain embodiments a composition of the invention is for use in the treatment of atopic dermatitis infected with Gram-positive bacteria, for example *Staphylococcus* and/or *Streptococcus* bacteria.

In certain embodiments the non-aqueous composition of the invention is for use in the topical treatment of atopic dermatitis wherein the atopic dermatitis is asymptomatic of the effects of a bacterial infection.

Acne

In a particular embodiment of the invention there is provided a composition of the invention for use in the topical prevention or treatment of acne.

It may be that the infection is disease is acne, for example acne vulgaris. The acne may be mild, moderate or severe acne. The acne may be inflammatory acne. The acne may be non-inflammatory acne. When the disease or infection is acne it may be that the Gram-positive bacteria is *Propionibacterium* spp, particularly *Propionibacterium acnes.*

It may be that the infection or disease is not acne vulgaris.

The halogenated salicylanilide comprised in the composition may be any of the halogenated salicylanilides described herein. Suitably the halogenated salicylanilide is niclosamide or a pharmaceutically acceptable salt thereof, more particularly niclosamide in the free base form.

A primary cause of acne is the obstruction of the pilosebaceous canal resulting from excess sebum production and the formation of microcomedones. These in turn can progress to open comedones ("blackheads") or closed comedones ("whiteheads"). The microenvironment rich in sebum provides ideal conditions for bacterial growth, particularly *Propionibacterium acnes* and *Staphylococcus aureus*. The bacteria such as *Propionibacterium acnes* convert sebum to free fatty acids, resulting in a local inflammatory response and the development of inflammatory acne lesions. Inflammatory lesions may be characterised by papules (small pimples or swellings) or pustules (pus filled lesions in the epidermis or dermis).

The composition of the invention may be for use in the topical treatment or prevention of acne infected with a *Propionibacterium*, for example *Propionibacterium acnes*. The *Propionibacterium* may be resistant to one or more conventional antibiotics. For example the *Propionibacterium* may be resistant to one or more of erythromycin, clindamycin and a tetracycline (for example tetracycline, minocycline or doxycycline). In this embodiment it may be that the *Propionibacterium* is *Propionibacterium acnes*

The composition of the invention may be for use in the topical treatment or prevention of acne infected with a *Staphylococcus* Sp., for example *Staphylococcus aureus*. The *Staphylococcus* may be resistant to one or more conventional antibiotics. For example the *Staphylococcus aureus* may be resistant to one or more of erythromycin or clindamycin. The *Staphylococcus aureus* may be MRSA.

The composition of the invention may be for use in the topical treatment or prevention of inflammatory acne. The inflammatory acne may be moderate or severe inflammatory acne. The gel composition of the invention may be topically applied to the skin as a prophylactic treatment to prevent the occurrence of acne. The gel composition of the invention may be topically applied to a non-inflammatory acne lesion for example a microcomedone, an open comedone or a closed comedone to prevent the acne progressing to inflammatory acne. The prophylaxis or treatment of non-inflammatory acne or the treatment of inflammatory acne (particularly early stage or acute inflammatory acne) may be particularly suitable for minimising or preventing scarring of the skin which can occur in some subjects afflicted with inflammatory acne. Inflammatory acne results in an immune response and can lead to the formation of scar tissue at the site of inflammation. The scarring may be atrophic or hypertrophic scarring. The scarring may also lead to post-inflammatory hyper-pigmentation of the skin. Atrophic scarring (associated with loss of collagen) is particularly prevalent in acne. The topical gel composition of the invention for use in the treatment of non-inflammatory acne or inflammatory acne may reduce or eliminate the inflammation resulting from the bacterial infection, thereby preventing or reducing acne scarring.

Accordingly the composition of the invention may be for use in the topical prevention or reduction of skin scarring associated with acne. This aspect of the invention may be particularly suitable for the treatment of patients with dark skin, for example, African, Hispanic or Asian patients.

The composition of the invention may be for use in the topical prevention or treatment of mild, moderate or severe acne. Mild acne (Type 1 acne) is characterized by a lack of inflammation and is usually not particularly painful. The area of the body affected by the acne is usually limited. Non-inflamed blackheads and small red bumps (papules) are common with Type 1 acne. Moderate acne (Type 2 acne) is similar to Type 1 acne, but is characterized by increased levels of inflammation and redness. Pimples can range from small red bumps to medium sized whiteheads. Unlike Type 1 acne blemishes, the increased inflammation causes pimples that are often painful to the touch. Moderate to severe acne (Type 3 acne), is characterized by the presence of mid- to large-sized nodules and pustules that are frequently painful. In Type 3 acne, pimples are often associated with significant amounts of inflammation. Large whiteheads and large, painful red bumps are common in patients with Type 3 acne. Severe acne, or Type 4 acne, is characterized by a deep seated infection and extensive inflammation. Large cysts, which are essentially large, irregular nodules are a common feature in Type 4 acne.

The composition of the invention may be topically applied in combination with another active agent for the treatment of acne, for example a topical retinoid and/or benzoyl peroxide. The other active agent may be topically applied separately to the topical application of the composition of the invention. Alternatively the composition of the invention may incorporate the other agent, for example a retinoid and/or benzoyl peroxide such that all of the actives are present in a single topical formulation. Suitable topical retinoids include any retinoid suitable for the treatment of acne, for example retinoic acid (tretinion), adapalene or tazarotene. In one embodiment the composition of the invention is for use in combination with a retinoid for the topical treatment of acne. In another embodiment the composition of the invention is for use in combination with benzoyl peroxide for the topical treatment of acne. In another embodiment the composition of the invention is for use in combination with benzoyl peroxide and a retinoid for the topical treatment of acne.

A non-aqueous composition of the herein described (for example a non-aqueous gel composition) further comprising a retinoid and/or benzoyl peroxide forms a further aspect of the present invention.

A further aspect of the invention provides a kit comprising a first and second composition, wherein the first composition comprises a non-aqueous composition of the invention; and the second composition is selected from (i) a composition comprising a retinoid and (ii) a composition comprising benzoyl peroxide. Accordingly it may be that the kit comprises a first composition comprising a non-aqueous composition of the invention (e.g. comprising niclosamide or a pharmaceutically acceptable salt thereof); and a second composition comprising a retinoid. In a further embodiment the kit comprises a first composition comprising a non-aqueous composition of the invention (e.g. comprising niclosamide or a pharmaceutically acceptable salt thereof); and a second composition comprising benzoyl peroxide.

The kits according to this aspect of the invention are particularly suitable for use in the treatment of acne. Accordingly the kits described herein may further comprise instructions for topical application of the compositions comprised in the kit for the treatment of acne, suitably wherein the instructions for use require topical application of the composition for a sufficient period t of time to effectively treat the acne, for example for 1 week or more than 2 weeks.

When the kit includes a retinoid, the retinoid in the kit may be any retinoid suitable for use in the treatment of acne, for example selected from retinoic acid, adapalene and tazarotene).

The non-aqueous composition of the invention may be for use as a topical maintenance therapy in the treatment of acne. When used as a maintenance therapy the composition of the invention may act to maintain the acne in remission or to prevent recurrence or worsening of the condition following a primary treatment of the acne. The primary treatment acts to bring the acne under control and the maintenance use of the topical composition of the invention maintains control of the acne. The primary treatment may be any known treatment of acne, for example a retinoid, benzoyl peroxide, topical antibiotics or oral antibiotics or a combination thereof. The primary therapy may also be a topical composition of the invention as described herein.

Current treatment guidelines for acne recommend that conventional topical antibiotics for the treatment of acne are used in combination with another antibacterial agent such as a retinoid or benzoyl peroxide to minimise the risk of antibiotic resistance developing. The very low frequency of mutation associated with the topical use of a halogenated salicylanilide present in the composition of the invention is expected to significantly reduce the risk of antibiotic resistance emerging and therefore the composition of the invention is expected to useful as a monotherapy for the topical treatment of acne. This may be particularly advantageous for some patients who are sensitive, or intolerant, to benzoyl peroxide and/or topical retinoids. Use of a composition of the invention as a topical monotherapy for the treatment of acne may therefore reduce side effects compared to conventional acne treatments that include benzoyl peroxide or topical retinoids.

A common side effect of certain chemotherapies, especially epidermal growth factor receptor (EGFR) inhibitors is the development of acneform rashes (folliculitis). Acneform eruptions are observed as a side-effect in a very high proportion of patients treated with EGFR inhibitors including gefitinib, erlotinib, panitumumab and cetuximab and may be a surrogate marker for the efficacy of the EGFR inhibitor (Wollenberg et al, et al. Cutaneous side effects of EGFR inhibitors—appearance and management, *Dtsch. Med. Wochenschr.* 135(4):149-54 (2010 January)).

The acneform reaction begins as facial erythema followed by papules and pustules over the face and upper trunk. Unlike true acne, the pustules are sterile. However, topical antibiotics have been shown to be effective in the treatment of acneform rashes associated with chemotherapy.

Accordingly the gel composition of the invention described herein may be for use in the topical treatment of an acneform rash, particularly an acneform rash in a subject that has been treated with or is being treated with an EGFR inhibitor.

Decolonisation

The composition of the invention may be for use to decolonise a subject carrying a Gram-positive bacteria (including any of the Gram-positive bacteria described herein, for example MRSA). Such decolonisation may be effective in preventing or reducing the spread of infection to other subjects particularly in a hospital environment. Decolonisation may also prevent or reduce the risk of surgical site infections resulting from surgical or medical procedures carried out on the patient or at the site of medical devices such as catheters or IV lines or cannula. Accordingly the composition of the invention may be for use in the decolonisation of a subject prior to carrying out a surgical procedure on the subject, wherein the composition is applied topically to the subject. Such surgical procedures include, for example elective surgical procedures such as hip or knee replacement. In one embodiment the composition of the invention may be for use in the decolonisation of a subject prior to dialysis. Pre-dialysis decolonisation may prevent or reduce the risk of infection associated with dialysis such as vascular line infection or catheter related bloodstream infections (CRBSI) infections. Decolonisation may be achieved by topically administering the gel composition comprising the halogenated salicylanilide to sites on the subject which are colonised by the Gram-positive bacteria. It is known that a common site for bacterial colonisation such as MRSA is the nose. Accordingly, the composition of the invention may be applied topically to the nose. Particularly the composition of the invention may be applied to the anterior nares (the inner surface of the nostrils).

Uses of the Gel Compositions in Methods of Treatment

Also provided are methods of treating a subject having a Gram-positive bacterial infection that include topically administering to a subject having a Gram-positive bacterial infection the composition of the invention in an amount sufficient to decrease the population of Gram-positive bacteria in the subject.

The present invention provides a method of treating a subject suffering from an infection contributed to or caused by Gram-positive bacteria as hereinbefore described, said method comprising the step of topically administering a therapeutically effective amount of the composition of the invention. The method of treatment of the invention may be characterized by a rate of developing spontaneous resistance to these bacteria of less than $10^{-6}$, such as less than $10^{-7}$ or $10^{-8}$, such as less than $4 \times 10^{-9}$. One example which is of special interest is a gel composition of the invention comprising niclosamide which may be characterized by a rate of developing spontaneous resistance to these bacteria of less than $10^{-8}$, such as less than $1 \times 10^{-9}$.

The present invention may provide the use of the composition of the invention in the manufacture of a medicament for the topical prevention and/or treatment of an infection contributed to or caused by Gram-positive bacteria.

The methods of treatment and uses described in this section may be for the treatment and/or prevention of any of the conditions described herein. The methods and uses are may be for infections caused by any of the Gram-positive bacteria described herein.

Dosages and Dosage Regimens

It may be that the composition of the invention is administered topically as an acute treatment of an infection, for example administration for a period of less than 2 weeks.

The combined effect of the potent antibacterial effect of the halogenated salicylanilide together with the low risk of bacterial resistance emerging may make the composition of the invention particularly suitable for administered as a chronic treatment of an infection, for example administration for a period of more than 2 weeks.

The duration of treatment will depend upon the nature of the infection being treated. Suitably the topical administration is continued until the infection is eradicated and/or the symptoms of the infection are reduced or eliminated. The upper limit of the period of treatment can be readily determined by a physician. The halogenated salicylanilide may, for example, be topically administered for a period selected from 1 day, 2 days, more than 3 days, more than 1 week, more than 2 weeks, more than 3 weeks, more than 4 weeks, more than 6 weeks, more than 12 weeks, more than 6 months and more than 1 year. For example the halogenated salicylanilide may be topically administered for a period of more than two weeks to about 1 year; a period 3 weeks to 1 year; a period of 4 weeks to 1 year; a period of 4 weeks to 6 months; or 4 weeks to 3 months.

The frequency of topical administration of the composition of the invention will depend upon a number of factors that may readily be determined by a physician, for example the severity of the infection, the responsiveness to initial treatment and the particular infection being treated. Suitably the gel composition of the invention may be topically administered once per day, twice per day, three times per day, four times per day, once every other day or once per week.

The dosage of the halogenated salicylanilide administered with the composition of the invention will vary depending upon a number of factors including, for example the age, weight and gender of animal or human suffering from the infection, the severity of the infection and the selected administration frequency.

A suitable dosage for topical application can be readily determined by a physician. Suitably the composition of the invention is topically applied in an amount of from about 0.01 to about 10000 $mg/cm^2$, for example from about 0.1 to about 1000 $mg/cm^2$, preferably from about 1 to about 100 $mg/cm^2$. The composition suitably comprises the halogenated salicylanilide in an amount of from about 0.1% to about 10%, preferably from about 0.1% to about 10%, more preferably from about 0.1% to about 6% and even more preferably from about 0.5% to about 4% by weight of the composition. Generally, the amount of the halogenated salicylanilide to be administered topically may be in the range of 0.01-2 $mg/cm^2$, preferably between 0.05-1 $mg/cm^2$ and even more preferably between 0.05-0.5 $mg/cm^2$, for example between 0.2 $mg/cm^2$.

The composition of the invention is suitably applied to the site of infection and is gently rubbed in to provide a cover of the composition (for example gel) over the infected site. Alternatively the composition of the invention may be applied to a suitable carrier, for example a wound dressing or a patch which is applied to the site of infection.

Subjects

The non-aqueous compositions of the invention are suitable for use in the topical treatment of subject affected by any of the diseases or infections described herein. The subject may be a warm blooded mammal. In particular embodiments the subject treated is a human. In certain embodiments the subject may be an animal. In certain embodiments the composition of the invention is for use as veterinary product for the topical treatment of an animal. In certain embodiments the non-aqueous topical compositions of the invention (for example the gel compositions described herein) are for use in the topical treatment of diseases and infections in commercial animals such as livestock (e.g. cows, sheep, chickens, pigs, geese, ducks, goats, etc.). In other embodiments the, the compositions of the present invention may be for use in the topical treatment of diseases or infections in companion animals such as cats, dogs, horses, etc.

The following examples are intended to illustrate, but not to limit, the invention in any manner, shape, or form, either explicitly or implicitly.

EXAMPLES

Example 1

Experimental tests were conducted to determine the antibacterial activity and the mutation rate conferring resistance for halogenated salicylanilides and reference compounds.

Microorganisms

The methicillin-resistant *S. aureus* (MRSA) 01 strain was used as the primary test microorganism as a representative bacteria commonly found in skin infections. This strain is a community-acquired MRSA clinical isolate of USA 300 type, from a skin abscess.

Twenty-one other MRSA and methicillin-sensitive *S. aureus* strains, and 4 *Streptococcus pyogenes* strains, were also included in the study (Table 2). These covered fusidic acid- and mupirocin-resistant strains, these two types of resistance being of clinical relevance.

Strains were conserved in Luria Bertani (LB) Broth (*S. aureus*) or Brain Heart Infusion (BHI) (*S. pyogenes*) supplemented with glycerol 15% (v/v) at −80° C., and reactivated by isolation on LB (*S. aureus*) or BHI (*S. pyogenes*) agar plates. Strains were cultivated in Mueller Hinton (MH) Broth-cation adjusted (*S. aureus*) supplemented with lysed horse blood 2.5% (v/v) (*S. pyogenes*). All strains were cultivated at 37° C., aerobically for *S. aureus* strains.

TABLE 2

| Species | Strains | Mupirocin and fusidic acid Resistance gene | USA type | MLSTSCCmec | spa type | Origin |
|---|---|---|---|---|---|---|
| S. aureus | Newman | | | | | |
| | MRSA 01 | | USA 300 | ST8-IV | t008 | SSI |
| | MRSA 02 | | | ST30-IV | t019 | SSI |
| | MRSA 03* | ND | USA 400 | ST1-IV | t127 | SSI |
| | MRSA 04 | | | ST772-V | t657 | SSI |
| | MRSA 05 | | | ST130-XI | t843 | SSI |
| | MRSA 06 | | | CC97-5C2 (V) | | SSI |
| | MRSA 07 | | | ST398 | | KU |
| | MRSA 08‡ | ND | USA 300 | ST8 | | KU |
| | MRSA 09 | | USA600 | ST45 | | KU |
| | MRSA 10 | | | ST22-IV | | KU |
| | MRSA 11 | | | ST36-II | | KU |
| | EEFIC 01* | | | CC123 | t171 | SSI |
| | EEFIC 02* | | | CC123 | t171 | SSI |
| | MRSA 12* | fusB | | CC80 | t044 | SSI |
| | MRSA 13* | fusB | | CC80 | t044 | SSI |
| | MSSA 01* | fusC | | CC1 | t127 | SSI |
| | MSSA 02* | fusC | | CC1 | t127 | SSI |
| | MRSA 14* | fusA | | CC22 | t2006 | SSI |
| | MRSA 15* | fusA | | CC30 | t166 | SSI |
| | MRSA 16‡ | mupA | | CC30 | t019 | SSI |
| | MRSA 17‡ | mupB | | CC509 | t375 | SSI |
| S. pyogenes | 01 | | | | | SSI |
| | CCUG 25571 | | | | | |
| | ATCC 19615 | | | | | |
| | ATCC 12385 | | | | | |

All Staphylococcus aureus strains but one (MRSA 07) are human clinical isolates;
MRSA 07 is a Livestock-associated MRSA;
MRSA 02 and MRS 04 are Community-associated MRSA;
*strains resistant to fusidic acid;
‡strains resistant to mupirocin;
ND: Not determined;
EEFIC: Epidemic European Fusidic acid-resistant Impetigo Clone;
MLST: Multilocus Sequence Typing;
SSCmec: staphylococcal cassette chromosome mec;
spa: S. aureus protein A;
KU: Copenhagen University;
SSI: National Reference Laboratory for Staphylococci, Statens Serum Instityt, Copenhagen, Denmark.

Antibacterial Activity

The following tests were performed to assess the antibacterial activity in vitro (FIG. 1):

Minimum Inhibitory Concentration (MIC) Assay

The MIC was determined using 96-well plates, and serial two-fold dilutions of niclosamide (from Sigma) (from 51.2 to 0.025 µg/ml) in above indicated medium, with 150 µl per well. Bacterial cultures were stopped in their exponential growth phase and plates were inoculated with the approximate concentration of $10^3$ cells per well. Plates were incubated at 37° C. for 18 hours (S. aureus) or 24 hours (S. pyogenes). Optical density at a wavelength of 600 nm was measured at the end of the incubation time. Inhibition was calculated as (Inhibition=$1-OD_{test}/OD_{no\ treatment}$) and MIC values were determined as the minimum concentration giving 100% inhibition. Experiments were performed at least as triplicate biological replicates with all strains.

The observed inhibition could have been attributable a bactericidal or a bacteriostatic activity, which could not be determined from this experiment. The following assay was thus carried out in order to determine if niclosamide kills or inhibits growth of S. aureus.

Time-Kill Assay

This assay was performed in 20 ml of medium. It included a negative control (medium without bacteria), a positive control (bacteria grown without niclosamide) and the assay (bacteria grown with niclosamide). Niclosamide was tested at 10 fold its MIC, determined in the previous experiment. This experiment was performed with the primary test microorganism indicated above.

The overnight culture was stopped and $OD_{600}$ was measured. Culture was then diluted in indicated medium to obtain an $OD_{600}$ of 0.25 in order to have about $5 \times 10^8$ cfu/ml. Two hundred µl of this diluted culture were then added in all conditions except in the negative control. Initial bacterial concentration was about $5 \times 10^6$ cfu/ml. Tubes were incubated aerobically at 37° C. for 24 hours.

Bacteria were enumerated before the incubation, after 30 minutes, 1, 2, 4, 8 and 24 hours of incubation by serial dilutions in NaCl 0.9% and plating on LB agar, with 2 plates per dilution. Plates were incubated at 37° C. and colonies enumerated after 24 hours.

The compound was considered bactericidal if the reduction of the bacterial inoculum was superior or equal to 3 logo cfu/ml, bacteriostatic if reduction was inferior to 3 $log_{10}$ cfu/ml.

Results and Conclusions

Microbiology: MIC & Kill curves—FIGS. 1 & 2 and Tables 3 and 4

TABLE 3 in-vitro susceptibility of S. aureus clinical isolates
and S. aureus ATCC 29213 reference strain.

|  |  | MIC (µg/ml) |
|---|---|---|
| S. aureus strains | Newman | 0.2 |
|  | MRSA 01 | 0.4 |
|  | MRSA 02 | 0.2 |
|  | MRSA 03* | 0.4 |
|  | MRSA 04 | 0.4 |
|  | MRSA 05 | 0.2 |
|  | MRSA 06 | 0.4 |
|  | MRSA 07 | 0.2 |
|  | MRSA 08* | 0.4 |
|  | MRSA 09 | 0.2 |
|  | MRSA 10 | 0.4 |
|  | MRSA 11 | 0.1 |
|  | EEFIC 01* | 0.4 |
|  | EEFIC 02* | 0.2 |
|  | MRSA 12* | 0.4 |
|  | MRSA 13* | 0.4 |
|  | MSSA 01* | 0.4 |
|  | MSSA 02* | 0.4 |
|  | MRSA 14* | 0.4 |
|  | MRSA 15* | 0.2 |
|  | MRSA 16* | 0.2 |
|  | MRSA 17* | 0.2 |
| S. pyogenes strains | 01 | 3.2 |
|  | CCUG 25571 | 3.2 |
|  | ATCC 19615 | 3.2 |
|  | ATCC 12385 | 1.6 |

Table 4 shows the therapeutic indices of the halogenated salicylanilides niclosamide, closantel, oxyclozanide and rafoxanide. The therapeutic index was calculated as the ratio of the $LD_{50}$ in rats to the MIC of the test compound. The $LD_{50}$ values shown in Table 3 were taken from published literature values for these compounds for example in Andrews et al. *Pharmac. Ther.* Vol 19 pp 245 (1983).

TABLE 4

Therapeutic indexes of halogenated salicylanilides, calculated from their MICs against S. aureus and S. pyogenes strains and their lethal Dose 50 (LD50) in rats and mice.

|  | $Mic_{100}$ | | | | $LD_{50}$ rats | $LD_{50}$ | |
|---|---|---|---|---|---|---|---|
|  | S. aureus | | S. pyogenes | | p.o | mice p.o | Ther. Index |
| Compound | µg/ml | µM | µg/ml | µM | (mg/kg) | (mg/kg) | ($LD_{50,rats}/MIC_{100, S.\ aureus}$) |
| Niclosamide | ≤0.4 | ≤1.25 | ≤3 | ≤3 | 5000 | >1500 | 12,500,000 |
| Closantel | ≤1.7 | ≤2.5 | 12.8‡ | 19‡ | 300 | 331 | 176,000 |
| Oxyclozanide | 1.6* | 4* | 6.4‡ | 15.9‡ | 980-3500 | 300 | 612,000-2187,000 |
| Rafoxanide | 0.8* | 1.25* | 6.4‡ | 10‡ | 1500 | 270 | 1,875,000 |

*Tested against one strain: MRSA 01
‡Tested against one strain: S. pyogenes 01

The data shows that halogenated salicylanilides such as closantel, oxyclozanide, rafoxanide and particularly niclosamide are potent against Gram-positive strains such as *S. aureus* and *S. pyogenes*. Notably the effect is independent of the resistance profile of the isolates towards other currently used antibiotics for topical treatment of these microorganisms, including fusidic acid and mupirocin. Accordingly, the halogenated salicylanilides in general and niclosamide in particular are well suited as a possible treatment for both susceptible and resistant Gram-positive strains.

Mutational Frequency Evaluation

The frequency of spontaneous single-step mutations was determined on 3 different strains (MRSA, fusidic acid-resistant and mupirocin-resistant) as described by Drago et al. (2005) (Drago, L., De Vecchi, E., Nicola, L., Tocalli, L., & Gismondo, M. R. (2005). In vitro selection of resistance in Pseudomonas aeruginosa and Acinetobacter spp. by levofloxacin alone and in combination with beta-lactams and amikacin. *The Journal of Antimicrobial Chemotherapy*, 56(2), 353-359). One hundred µl of an initial inoculum of $10^9$ cfu/ml from an overnight culture were plated on LB agar plates supplemented with the test compound (0×, 1×, 2×, 4× and 10×MIC). Adequate dilutions were plated on plates without the compound.

Viable cell growth was enumerated after 48 hours of incubation at 37° C.

Ten replicates were carried out for each strain and fusidic acid, mupirocin and retapamulin were used as controls for the MRSA 01 strain.

Spontaneous mutations conferring resistance to halogenated salicylanilides occurred at a very low frequency (mutational frequency=$5 \times 10^{-9}$, $2 \times 10^{-8}$ and $1 \times 10^{-7}$ at MIC×1 for rafoxanide, closantel, and oxyclozanide respectively) and for niclosamide at an extremely low frequency (0≤mutational frequency<$4 \times 10^{-10}$ at MIC×1) compared to currently used antibiotics such as fusidic acid, retapamulin and mupirocin (mutational frequency: ≥$4 \times 10^{-5}$ at MIC×1) (see Table 5).

TABLE 5

Mutation rates conferring resistance to halogenated salicylanilides.

| Compound | Resistance mutation rate at MIC × 1 |
|---|---|
| Niclosamide | <$4 \times 10^{-9}$ [1] |
| Closantel | =$2 \times 10^{-8}$* |
| Oxyclozanide | =$1 \times 10^{-7}$* |
| Rafoxanide | =$5 \times 10^{-9}$* |
| Fusidic acid | ≥$4 \times 10^{-5}$* |

TABLE 5-continued

Mutation rates conferring resistance to halogenated salicylanilides.

| Compound | Resistance mutation rate at MIC × 1 |
|---|---|
| Mupirocin | ≥$4 \times 10^{-5}$* |
| Retapamulin | ≥$4 \times 10^{-5}$* | footnotes:
[1] Mutation rate conferring resistance against MRSA 01, MRSA 15 (fusidic acid-resistant) and MRSA 16 (mupirocin-resistant)
* Tested against one strain: MRSA 01

The mutation frequency rate is a measure of the number of resistant mutants within a given population following exposure the antibiotic. A mutation frequency of $10^{-9}$ means that there is less than one resistant mutant in a population of $10^9$ cells.

Unexpectedly, the resistance development towards halogenated salicylanilides in general and niclosamide in particular is much slower than resistance development towards currently approved topical antibiotics such as fusidic acid, mupirocin and retapamulin.

The high potency and the low rate of resistance development makes niclosamide particularly useful as a topical treatment of infections caused by Gram-positive organisms.

Example 2: Additional More Extensive Screen of Clinical Isolates Performed with Niclosamide Methods
Microorganisms Chosen for its relevance regarding bacterial skin infections, the methicillin-resistant *S. aureus* (MRSA) 01 strain was used as the primary test microorganism. This strain is a community-acquired MRSA clinical isolate of USA 300 type, from a skin abscess.

Two-hundred-four other MRSA and methicillin-sensitive *S. aureus* strains, and 4 *Streptococcus pyogenes* strains, were also included in the study. These covered fusidic acid- and mupirocin-resistant strains, these two types of resistance being of clinical relevance.

Strains were conserved in Luria Bertani (LB) Broth (*S. aureus*) or Brain Heart Infusion (BHI) (*S. pyogenes*) supplemented with glycerol 15% (v/v) at −80° C., and reactivated by isolation on LB (*S. aureus*) or BHI (*S. pyogenes*) agar plates. Strains were cultivated in Mueller Hinton (MH) Broth-cation adjusted (*S. aureus*) or BHI (*S. pyogenes*). All strains were cultivated aerobically (microaerobically for *S. pyogenes* strains) at 37° C.

Antibacterial Activity
Minimum Inhibitory Concentration (MIC) Assay

Minimal inhibitory concentrations (MICs) of niclosamide, fusidic acid, and mupirocin were determined according to CLSI criteria with a doubling dilution concentration range (16 to 0.008 µg/ml) in Mueller Hinton Broth cation-adjusted (Fluka Analytical 90922), using 96-well plates, for 205 different *S. aureus* strains. *S. aureus* ATCC 29213 was included as a control reference strain and clindamycin and vancomycin were included as control antibiotics.

Bacterial cultures were stopped in their exponential growth phase and plates were inoculated with the approximate concentration of $5 \times 10^5$ cells per well. Plates were incubated at 37° C. for 18 hours (*S. aureus*) or 24 hours (*S. pyogenes*). Optical density at a wavelength of 600 nm was measured at the end of the incubation time. Inhibition was calculated as (Inhibition=1−$OD_{test}$/$OD_{no\ treatment}$) and MIC values were determined as the minimum concentration giving 100% inhibition.

Due to interference with blood (MIC increased by 16 with 5% lysed horse blood), the MIC determination against *S. pyogenes* strains was performed in BHI.

Results and Discussion
In Vitro MIC Determination and Breadth of Effect

Figure 3:
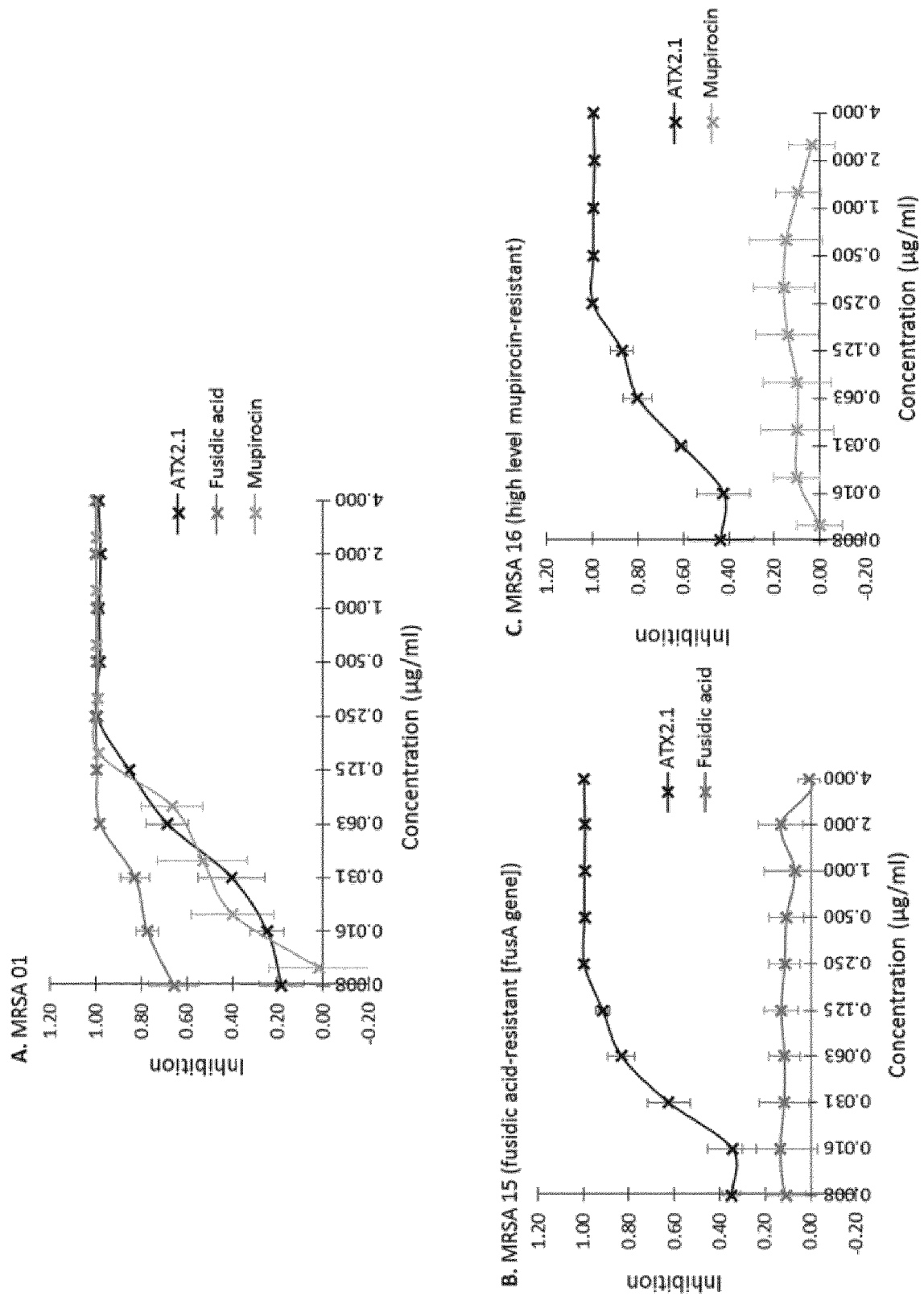
FIG. 3 shows the dose-response curves of niclosamide, fusidic acid and mupirocin against S. aureus with methicillin-resistant strains (A), fusidic acid-resistant strain (B) and mupirocin-resistant strain (C). ATX 2.1 in FIG. 3 is niclosamide
Figure 4:
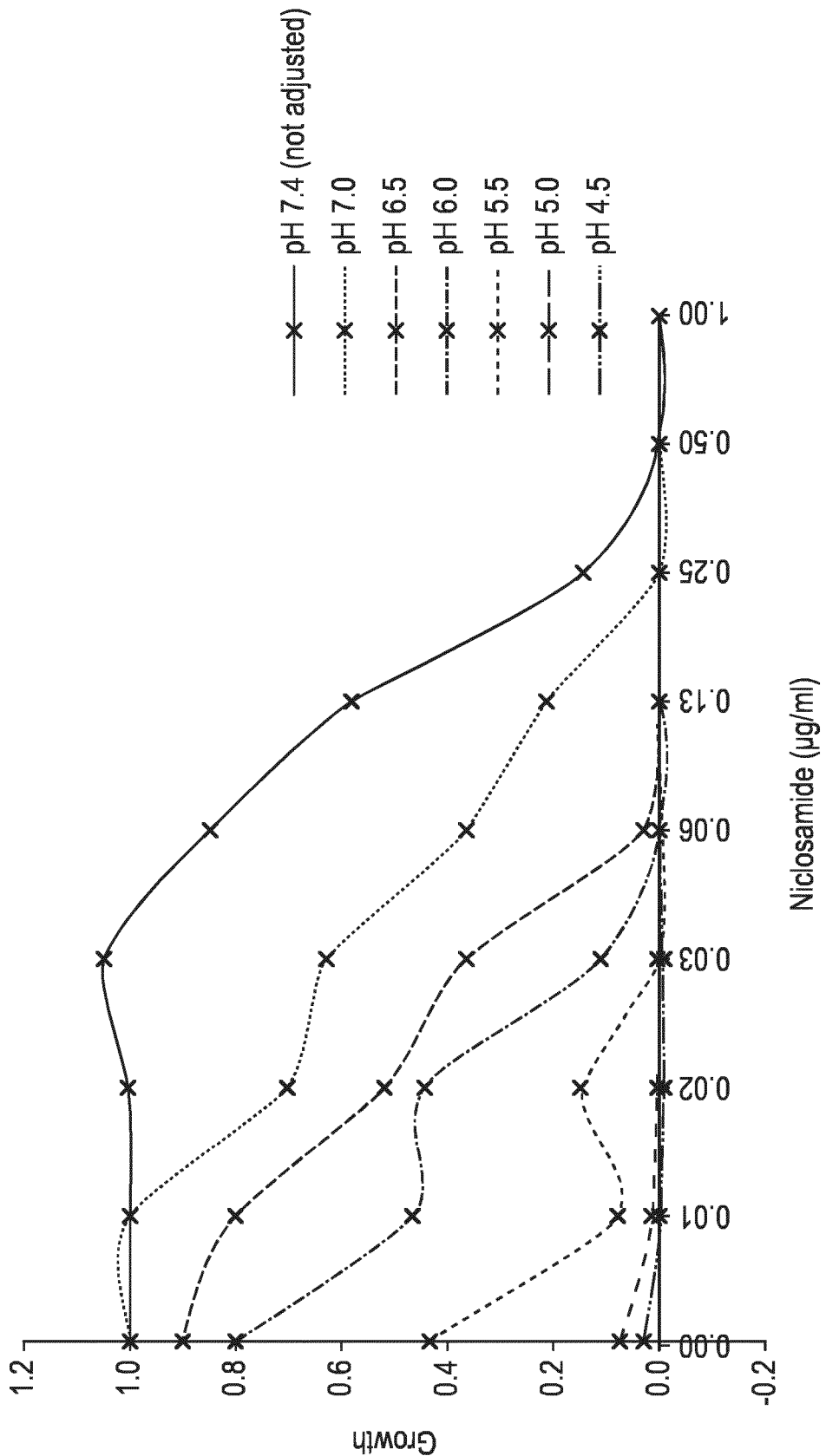
FIG. 4 shows the growth of S. aureus at different pH as a function of niclosamide concentration (average of 3 replicates). The growth of S. aureus without niclosamide (0 µg/ml) is comparable from pH 7.4 to pH 6.0. The growth without niclosamide is slightly inhibited at pH 5.5 and completely inhibited with pH equal or below 5.0.

The MIC of niclosamide was ≤0.5 µg/ml against all targeted *S. aureus* and *S. pyogenes* strains, including the strains resistant to fusidic acid, mupirocin, clindamycin and retapamulin (Table 6, Table 7, Table 8 and FIG. 3).

TABLE 6 in-vitro susceptibility of *S. aureus* clinical isolates and *S. aureus* ATCC 29213 reference strain.

| | MIC (µg/ml) | | | | | |
|---|---|---|---|---|---|---|
| | niclosamide | Fusidic acid | Mupirocin | Retapamulin | Clindamycin | Vancomycin |
| ATCC 29213 | 0.5 | 0.06 | 0.125 | 0.03 | 0.125 | 1 |
| Newman | 0.25 | 0.25 | 0.25 | 0.03 | 0.125 | 2 |
| MRSA 01 | 0.25 | 0.125 | 0.25 | 0.06 | 0.125 | 1 |
| MRSA 02 | 0.25 | 0.5 | 0.25 | 0.06 | 0.25 | 2 |
| MRSA 03 | 0.25 | 16 | 0.25 | 0.03 | 0.125 | 1 |
| MRSA 04 | 0.25 | 0.25 | 0.25 | 0.06 | 0.125 | 2 |
| MRSA 05 | 0.25 | 0.125 | 0.125 | 0.03 | 0.125 | 1 |
| MRSA 06 | 0.25 | 0.125 | 0.25 | 0.03 | 0.125 | 2 |
| MRSA 07 | 0.125 | 0.25 | 0.25 | 0.06 | 0.125 | 1 |
| MRSA 08 | 0.25 | 0.125 | >16 | 0.03 | >16 | 1 |
| MRSA 09 | 0.125 | 0.25 | 0.25 | 0.06 | 0.25 | 2 |
| MRSA 10 | 0.25 | 1 | 0.25 | 0.06 | 0.25 | 1 |
| MRSA 11 | 0.25 | 1 | 0.5 | 0.06 | >16 | 1 |
| EEFIC 01 | 0.25 | 4 | 0.125 | 0.03 | 0.125 | 1 |
| EEFIC 02 | 0.25 | 4 | 0.125 | 0.03 | 0.125 | 1 |
| MRSA 12 | 0.5 | 4 | 0.125 | 0.03 | ND | ND |
| MRSA 13 | 0.25 | 4 | 0.25 | 0.06 | 0.125 | 1 |
| MSSA 01 | 0.5 | 4 | 0.125 | 0.03 | 0.125 | 1 |
| MSSA 02 | 0.25 | 4 | 0.125 | 0.03 | 0.125 | 1 |
| MRSA 14 | 0.25 | >16 | 0.125 | 0.03 | >16 | 1 |
| MRSA 15 | 0.25 | >16 | 0.25 | 0.06 | 0.125 | 2 |
| MRSA 16 | 0.25 | 0.25 | >16 | 0.06 | 0.25 | 1 |
| MRSA 17 | 0.25 | 4 | >16 | 0.03 | >16 | 2 |
| MRSA 18 | 0.25 | 0.25 | 0.125 | 0.06 | 0.125 | 1 |
| MRSA 19 | 0.25 | 0.125 | 0.25 | 0.03 | 0.125 | 1 |
| MRSA 20 | 0.25 | 0.125 | 0.25 | 0.06 | 0.06 | 1 |
| MRSA 21 | 0.25 | 0.125 | 0.125 | 0.125 | 0.03 | 1 |
| MRSA 22 | 0.25 | >16 | 0.25 | 0.06 | 0.06 | 0.5 |
| MRSA 23 | 0.25 | 0.25 | 0.25 | 0.06 | 0.125 | 1 |
| MRSA 24 | 0.25 | 0.25 | 0.25 | 0.06 | 0.125 | 2 |

TABLE 6-continued in-vitro susceptibility of *S. aureus* clinical isolates and *S. aureus* ATCC 29213 reference strain.

| | MIC (μg/ml) | | | | | |
|---|---|---|---|---|---|---|
| | niclosamide | Fusidic acid | Mupirocin | Retapamulin | Clindamycin | Vancomycin |
| MRSA 25 | 0.25 | 16 | 0.25 | 0.06 | 0.125 | 1 |
| MRSA 26 | 0.5 | 0.5 | 0.5 | 0.06 | >16 | 1 |
| MRSA 27 | 0.5 | 0.25 | 0.25 | 0.06 | 0.125 | 1 |
| MRSA 28 | 0.25 | 0.06 | 0.5 | 0.06 | 0.06 | 1 |
| MRSA 29 | 0.5 | 4 | 0.25 | 0.06 | 0.125 | 1 |
| MRSA 30 | 0.25 | 0.125 | 0.125 | 0.03 | 0.06 | 1 |
| MRSA 31 | 0.25 | 0.25 | 0.25 | 16 | >16 | 1 |
| MRSA 32 | 0.25 | 0.5 | 0.25 | 0.06 | 0.125 | 1 |
| MRSA 33 | 0.25 | 0.5 | 0.25 | 0.06 | 0.125 | 1 |
| MRSA 34 | 0.25 | 0.25 | 0.25 | 0.06 | 0.125 | 1 |
| MRSA 35 | 0.25 | 16 | 0.5 | 0.03 | >16 | 1 |
| MRSA 36 | 0.25 | 8 | 0.25 | 0.06 | 0.06 | 1 |
| MRSA 37 | 0.25 | 0.5 | 0.25 | 0.06 | 0.125 | 1 |
| MRSA 38 | 0.25 | 8 | 0.125 | 0.06 | 0.125 | 1 |
| MRSA 39 | 0.25 | 8 | 0.25 | 0.06 | 0.06 | 1 |
| MRSA 40 | 0.25 | 0.125 | 0.25 | 0.03 | 0.06 | 1 |
| MRSA 41 | 0.25 | >16 | 0.125 | 0.02 | 0.06 | 1 |
| MRSA 42 | 0.25 | 0.25 | 0.25 | 0.06 | >16 | 1 |
| MRSA 43 | 0.25 | 0.125 | 0.25 | 0.06 | 0.06 | 1 |
| MRSA 44 | 0.25 | 4 | 0.25 | 0.02 | 0.03 | 1 |
| MRSA 45 | 0.25 | 0.06 | 0.13 | 0.02 | 0.06 | 1 |
| MRSA 46 | 0.25 | 0.06 | 0.13 | 0.02 | 0.03 | 1 |
| MRSA 47 | 0.25 | 0.06 | 0.25 | 0.02 | >16 | 0.5 |
| MRSA 48 | 0.25 | 2 | 0.13 | 0.02 | 0.03 | 0.5 |
| MRSA 49 | 0.25 | 0.25 | 0.25 | 0.02 | 0.03 | 2 |
| MRSA 50 | 0.25 | 0.03 | 0.25 | 0.02 | 0.02 | 1 |
| MRSA 51 | 0.125 | 0.13 | 0.25 | 0.03 | 0.06 | 1 |
| MRSA 52 | 0.25 | 0.06 | 0.25 | 0.02 | 0.03 | 1 |
| MRSA 53 | 0.25 | 0.25 | 0.25 | 0.03 | 0.06 | 1 |
| MRSA 54 | 0.25 | 0.125 | 0.25 | 0.03 | 0.06 | 2 |
| MRSA 55 | 0.25 | 4 | 0.25 | 0.02 | 0.03 | 0.5 |
| MRSA 56 | 0.25 | 0.06 | 0.25 | <0.01 | 0.03 | 1 |
| MRSA 57 | 0.25 | 0.125 | 0.125 | 0.02 | 0.03 | 1 |
| MRSA 58 | 0.25 | 4 | 0.125 | 0.02 | 0.06 | 1 |
| MRSA 59 | 0.25 | 0.06 | 0.125 | 0.02 | 0.03 | 1 |
| MRSA 60 | 0.25 | 8 | 0.25 | 0.02 | 0.06 | 0.5 |
| MRSA 61 | 0.25 | 0.06 | 0.25 | 0.02 | 0.03 | 2 |
| MRSA 62 | 0.25 | 0.06 | 0.25 | 0.02 | 0.06 | 2 |
| MRSA 63 | 0.25 | 0.125 | 0.125 | 0.02 | 0.06 | 1 |
| MRSA 64 | 0.25 | 0.25 | 0.25 | 0.02 | 0.06 | 1 |
| MRSA 65 | 0.25 | 0.06 | 0.25 | 0.02 | 0.03 | 1 |
| MRSA 66 | 0.25 | 0.06 | 0.25 | 0.02 | 0.03 | 1 |
| MRSA 67 | 0.25 | 0.25 | 0.125 | 0.02 | 0.03 | 1 |
| MRSA 68 | 0.25 | 0.125 | 0.25 | 0.02 | 0.03 | 1 |
| MRSA 69 | 0.25 | 4 | 0.125 | <0.01 | 0.03 | 1 |
| MRSA 70 | 0.125 | 8 | 0.25 | 0.02 | 0.06 | 1 |
| MRSA 71 | 0.25 | 0.06 | 0.125 | <0.01 | 0.02 | 1 |
| MRSA 72 | 0.25 | 16 | 0.25 | 0.03 | 0.06 | 1 |
| MRSA 73 | 0.5 | 0.25 | 0.25 | 0.03 | 0.125 | 1 |
| MRSA 74 | 0.25 | 0.25 | 0.25 | 0.03 | 0.125 | 1 |
| MRSA 75 | 0.5 | 0.5 | 0.5 | 0.03 | 0.125 | 1 |
| MRSA 76 | 0.25 | 0.25 | 0.25 | 0.03 | 0.125 | 1 |
| MRSA 77 | 0.25 | 16 | 0.25 | 0.03 | 0.125 | 2 |
| MRSA 78 | 0.5 | 0.125 | 0.25 | 0.03 | 0.06 | 1 |
| MRSA 79 | 0.25 | 0.5 | 0.25 | <0.01 | 0.03 | 1 |
| MRSA 80 | 0.5 | 0.125 | 0.25 | 0.02 | 0.06 | 1 |
| MRSA 81 | 0.5 | 0.25 | 0.25 | 0.03 | 0.125 | 1 |
| MRSA 82 | 0.25 | 8 | 0.25 | 0.03 | 0.125 | 2 |
| MRSA 83 | 0.5 | 0.06 | 0.25 | 0.03 | 0.06 | 1 |
| MRSA 27b | 0.25 | 8 | 0.25 | 0.02 | 0.06 | 1 |
| MRSA 84 | 0.25 | 8 | 0.25 | 0.03 | 0.125 | 2 |
| MRSA 85 | 0.5 | 4 | 0.25 | 0.03 | 0.125 | 1 |
| MRSA 86 | 0.25 | >16 | 0.25 | 0.03 | 0.06 | 2 |
| MRSA 87 | 0.25 | 0.125 | 0.25 | 0.02 | 0.06 | 1 |
| MRSA 88 | 0.25 | 0.06 | 0.25 | 0.03 | 0.06 | 1 |
| MRSA 89 | 0.5 | 0.06 | 0.25 | 0.02 | >16 | 1 |
| MRSA 90 | 0.5 | 16 | 0.25 | 0.06 | 0.125 | 1 |
| MRSA 91 | 0.25 | 0.25 | 0.25 | 0.06 | 0.125 | 1 |
| MRSA 92 | 0.25 | 8 | 0.25 | 0.06 | 0.06 | 1 |
| MRSA 93 | 0.25 | 0.02 | 0.25 | 0.02 | 0.03 | 2 |
| MRSA 94 | 0.25 | 0.125 | 0.25 | 0.03 | 0.125 | 2 |
| MRSA 95 | 0.25 | 8 | 0.25 | 0.03 | 0.125 | 2 |

TABLE 6-continued in-vitro susceptibility of *S. aureus* clinical isolates and *S. aureus* ATCC 29213 reference strain.

| | MIC (µg/ml) | | | | | |
|---|---|---|---|---|---|---|
| | niclosamide | Fusidic acid | Mupirocin | Retapamulin | Clindamycin | Vancomycin |
| MRSA 96 | 0.25 | 0.125 | 0.125 | 0.03 | >16 | 1 |
| MRSA 97 | 0.25 | 8 | 0.25 | 0.03 | 0.06 | 1 |
| MRSA 98 | 0.5 | 0.06 | 0.5 | 0.03 | >16 | 1 |
| MRSA 99 | 0.25 | 0.125 | 0.5 | 0.03 | 0.125 | 1 |
| MRSA 100 | 0.25 | 0.125 | 0.5 | 1 | 0.25 | 1 |
| MRSA 101 | 0.5 | 8 | 0.25 | 0.03 | 0.06 | 1 |
| MRSA 102 | 0.25 | 0.06 | 0.25 | 0.03 | 0.06 | 2 |
| MRSA 103 | 0.25 | 8 | 0.25 | 0.03 | 0.125 | 1 |
| MRSA 104 | 0.5 | 0.25 | 0.25 | 0.03 | 0.125 | 1 |
| MRSA 105 | 0.25 | 0.125 | 0.25 | 0.03 | 0.125 | 1 |
| MRSA 106 | 0.25 | 0.125 | 0.25 | 0.06 | 0.125 | 1 |
| MRSA 107 | 0.25 | 0.25 | 0.25 | 0.06 | 0.125 | 2 |
| MRSA 108 | 0.25 | 4 | 0.25 | 0.03 | 0.125 | 1 |
| MRSA 109 | 0.25 | 0.25 | 0.25 | 0.03 | 0.125 | 1 |
| MRSA 110 | 0.25 | 0.06 | 0.125 | 0.03 | 0.125 | 1 |
| MRSA 111 | 0.5 | 8 | 0.25 | 0.03 | 0.125 | 1 |
| MRSA 112 | 0.25 | 0.06 | 0.25 | 0.03 | 0.06 | 1 |
| MRSA 113 | 0.25 | 0.125 | 0.25 | 0.03 | 0.06 | 1 |
| K000796 | 0.25 | 8 | 0.5 | 0.03 | 0.125 | 1 |
| K115688 | 0.25 | 0.125 | 0.25 | 0.03 | 0.125 | 2 |
| K000866 | 0.25 | 8 | 0.5 | 0.03 | 0.125 | 1 |
| K000864 | 0.25 | 0.25 | 0.25 | 0.03 | 0.125 | 1 |
| K000863 | 0.25 | 1 | 0.5 | 0.03 | 0.125 | 1 |
| K115689 | 0.25 | 0.125 | 0.25 | 0.03 | 0.125 | 2 |
| K000772 | 0.25 | >16 | 0.125 | 0.06 | 0.125 | 1 |
| K115498 | 0.25 | 0.125 | 0.5 | 0.03 | 0.125 | 2 |
| R000024 | 0.25 | 16 | 0.5 | 0.06 | 0.125 | 1 |
| R000020 | 0.5 | 0.125 | 0.5 | 0.03 | 0.125 | 1 |
| R000019 | 0.5 | 0.125 | 0.5 | 0.06 | 0.125 | 2 |
| U115579 | 0.25 | 0.25 | 0.5 | 0.06 | 0.125 | 1 |
| 115370U | 0.25 | 0.5 | 0.125 | 0.06 | 0.125 | 1 |
| 114660U | 0.25 | 0.25 | 0.25 | 0.06 | 0.125 | 1 |
| 115584D | 0.25 | 0.25 | 0.5 | 0.06 | 0.125 | 2 |
| 115740E | 0.5 | 0.25 | 0.25 | 0.06 | 0.125 | 1 |
| 115810E | 0.25 | 0.25 | 0.25 | 0.06 | 0.125 | 1 |
| 115628T | 0.25 | 8 | 0.25 | 0.03 | 0.06 | 2 |
| 000274T | 0.25 | 0.5 | 0.5 | 0.06 | 0.125 | 1 |
| 115691T | 0.5 | 0.25 | 0.25 | 0.03 | 0.125 | 1 |
| 115903T | 0.5 | 8 | 0.5 | 0.03 | 0.125 | 1 |
| 116122T | 0.25 | 0.125 | 0.5 | 0.03 | 0.125 | 1 |
| 115015T | 0.5 | 0.25 | 0.5 | 0.06 | 0.125 | 2 |
| 115273C | 0.5 | 0.25 | 0.25 | 0.03 | 0.125 | 1 |
| 000040C | 0.5 | 0.25 | 0.25 | 0.03 | 0.125 | 1 |
| 115690C | 0.25 | 8 | 0.125 | 0.25 | 0.5 | 2 |
| 115561C | 0.25 | 0.125 | 0.5 | 0.03 | 0.125 | 1 |
| 115445C | 0.5 | 0.25 | 0.25 | 0.03 | 0.125 | 1 |
| 115263C | 0.25 | 0.125 | 0.25 | 0.03 | 0.06 | 2 |
| 115303C | 0.5 | 0.25 | 0.25 | 0.03 | >16 | 1 |
| 115268C | 0.5 | 0.25 | 0.5 | 0.03 | 0.125 | 1 |
| 115295C | 0.25 | 0.125 | 0.25 | 0.03 | 0.125 | 1 |
| 115242C | 0.5 | 8 | 0.25 | 0.03 | 0.06 | 1 |
| 115427C | 0.25 | 0.125 | 0.25 | 0.03 | 0.06 | 1 |
| 000041C | 0.25 | 0.25 | 0.25 | 0.03 | 0.06 | 1 |
| E5-1048654 | 0.25 | 0.5 | 0.25 | 0.06 | 0.125 | 1 |
| 9-2955245 | 0.25 | 0.25 | 0.25 | 0.06 | 0.125 | 1 |
| E5-1046019 | 0.25 | 0.25 | 0.25 | 0.03 | 0.125 | 1 |
| E5-1046020 | 0.5 | 0.25 | 0.25 | 0.06 | 0.125 | 1 |
| E5-1047585 | 0.25 | 0.25 | 0.25 | 0.03 | 0.125 | 1 |
| E5-1038294 | 0.5 | 0.25 | 0.25 | 0.03 | 0.125 | 1 |
| E5-1035779 | 0.5 | 0.125 | 0.5 | 0.03 | 0.125 | 1 |
| 9-1862936 | 0.5 | 0.125 | 0.25 | 0.03 | 0.125 | 1 |
| E5-1033091 | 0.5 | 0.03 | 0.25 | 0.02 | 0.06 | 1 |
| 9-26422166 | 0.5 | 8 | 0.25 | 0.03 | 0.125 | 1 |
| 9-2642158 | 0.25 | 0.25 | 0.25 | 0.06 | 0.125 | 1 |
| E5-1035775 | 0.5 | >16 | 0.25 | 0.06 | 0.125 | 1 |
| E5-1029558 | 0.25 | 16 | 0.5 | 0.03 | 0.125 | 1 |
| E5-1038279 | 0.5 | 4 | 0.25 | 0.03 | 0.125 | 1 |
| E5-1039697 | 0.25 | 0.5 | 0.25 | 0.06 | 0.125 | 1 |
| E5-1041979 | 0.5 | 0.25 | 0.5 | 0.03 | 0.125 | 1 |
| E5-1035284 | 0.25 | 0.25 | 0.25 | 0.03 | 0.125 | 1 |
| E5-1030469 | 0.25 | 0.125 | 0.25 | 0.03 | 0.125 | 2 |
| E5-1030472 | 0.5 | 0.25 | 0.5 | 0.06 | 0.125 | 1 |

TABLE 6-continued in-vitro susceptibility of *S. aureus* clinical isolates and *S. aureus* ATCC 29213 reference strain.

| | MIC (μg/ml) | | | | | |
|---|---|---|---|---|---|---|
| | niclosamide | Fusidic acid | Mupirocin | Retapamulin | Clindamycin | Vancomycin |
| E5-1041977 | 0.5 | 16 | 0.5 | 0.03 | 0.125 | 2 |
| E5-1041987 | 0.5 | 16 | 0.25 | 0.03 | 0.125 | 1 |
| E5-1039684 | 0.5 | 16 | 0.25 | 0.06 | 0.125 | 1 |
| E5-1041980 | 0.25 | 0.25 | 0.25 | 0.03 | 0.125 | 1 |
| E5-1033088 | 0.25 | 0.25 | 0.25 | 0.03 | 0.125 | 1 |
| E5-1035277 | 0.5 | 16 | 0.5 | 0.03 | 0.125 | 1 |
| E5-1046096 | 0.5 | 0.5 | 0.5 | 0.06 | 0.125 | 1 |
| E5-1046085 | 0.5 | 8 | 0.5 | 0.06 | 0.125 | 2 |
| 9-2625962 | 0.5 | 0.25 | 0.5 | 0.03 | 0.125 | 1 |
| E5-1043668 | 0.25 | 1 | 0.25 | 0.06 | 0.25 | 1 |
| E5-1048428 | 0.25 | 0.5 | 0.25 | 0.06 | 0.25 | 1 |
| E5-1047924 | 0.5 | 0.25 | 0.5 | 0.03 | 0.125 | 1 |
| E5-1047606 | 0.5 | 8 | 0.5 | 0.03 | 0.125 | 1 |
| E5-1046070 | 0.25 | 0.25 | 0.5 | 0.03 | 0.125 | 1 |
| E5-1046298 | 0.25 | 0.125 | 0.25 | 0.03 | 0.125 | 1 |
| E5-1046296 | 0.5 | 0.125 | 1 | 0.03 | 0.125 | 1 |
| E5-1046297 | 0.5 | 0.125 | 0.25 | 0.06 | 0.125 | 1 |
| E5-1043184 | 0.5 | 16 | 0.5 | 0.03 | 0.125 | 1 |
| E5-1038286 | 0.25 | 0.25 | 0.5 | 0.06 | 0.125 | 1 |
| E5-1037958 | 0.5 | 16 | 0.5 | 0.06 | 0.125 | 1 |
| E5-1037971 | 0.25 | 0.25 | 0.25 | 0.03 | 0.125 | 1 |
| E5-1033076 | 0.5 | 0.25 | 0.25 | 0.03 | 0.125 | 1 |
| E5-1033076 | 0.5 | 0.25 | 0.25 | 0.03 | 0.125 | 1 |
| E5-1029252 | 0.25 | 0.25 | 0.5 | 0.03 | 0.125 | 1 |
| E5-1030440 | 0.25 | 0.25 | 0.25 | 0.06 | 0.06 | 1 |
| E5-1030482 | 0.125 | 16 | 0.25 | 0.02 | 0.06 | 1 |
| E5-1046074 | 0.25 | 0.125 | 0.25 | 0.06 | 0.125 | 1 |
| E5-1048204 | 0.25 | 0.25 | 0.25 | 0.03 | 0.06 | 2 |
| E5-1048670 | 0.125 | 0.5 | 0.5 | 0.06 | 0.125 | 2 |
| E5-1046039 | 0.25 | 0.25 | 0.25 | 0.06 | 0.125 | 1 |
| E5-1045179 | 0.25 | 0.25 | 0.25 | 0.06 | 0.125 | 1 |
| E5-1046723 | 0.25 | 0.5 | 0.25 | 0.06 | 0.125 | 2 |

Resistances are indicated in Bold.
ND: not determined.

TABLE 7

MIC distribution of niclosamide against *Staphylococcus aureus* and *Streptococcus pyogenes* strains (percentage and ratio)

| | MIC (μg/ml) | | | |
|---|---|---|---|---|
| | 0.0625 | 0.125 | 0.25 | 0.5 |
| *Staphylococcus aureus* strains | | 3% (6/205) | 70% (144/205) | 27% (55/205) |
| *Streptococcus pyogenes* strains | 25% (1/4) | 25% (1/4) | 25% (1/4) | 25% (1/4) |

TABLE 8

MIC90, MIC50 and MIC ranges of niclosamide for *Staphylococcus aureus* strains.

| MIC90 | MIC50 | Range values |
|---|---|---|
| 0.5 μg/ml | 0.25 μg/ml | 0.125-0.5 μg/ml |

Niclosamide was inhibitory at a concentration equal or below 0.5 μg/ml for all targeted *S. aureus* and *S. pyogenes* strains, including fusidic acid- and mupirocin-resistant strains.

Example 3

A further study was carried out to examine the frequency of spontaneous mutation conferring resistance to niclosamide in 3 methicillin-resistant *Staphylococcus aureus* strains, including a fusidic acid- and a mupirocin-resistant strains. This frequency was compared with the frequencies of spontaneous mutation conferring resistance to fusidic acid, mupirocin and retapamulin in one MRSA strain.
Methods
Microorganisms Three methicillin-resistant *Staphylococcus aureus* (MRSA) clinical isolates, with different resistance profiles (MRSA 01, MRSA15 [fusidic acid-resistant strain] and MRSA 16 [mupirocin-resistant strain]) were chosen for their relevance regarding bacterial skin infections The MRSA 01 strain was used as the primary test microorganism. This strain is a community-acquired MRSA clinical isolate of USA 300 type, from a skin abscess.

Strains were conserved in Luria Bertani (LB) Broth supplemented with glycerol 15% (v/v) at −80° C., and reactivated by isolation on LB agar plates. Strains were cultivated aerobically in Mueller Hinton (MH) Broth-cation adjusted at 37° C.
Resistance Mutation Frequency Evaluation The frequency of spontaneous single-step mutations was determined on the 3 different strains as described by Drago et al. (2005) and Pannu et al. (2011). One hundred μl of an initial inoculum of about $10^9$ cfu/ml from an overnight culture were plated on LB agar plates supplemented with the test compound (0×, 1×, 2×, 4× and 10×MIC). Adequate dilutions were plated on plates without the compound.

Viable cell growth was enumerated after 48 hours of incubation at 37° C.

The spontaneous resistance frequency for an isolate-drug combination was calculated from the number of colonies that grew on plates containing drug versus the number of colonies that grew on drug-free agar.

Ten replicates were carried out for each strain and fusidic acid, mupirocin and retapamulin were used as controls for the MRSA 01 strain.

Results and Discussion

Spontaneous mutations conferring resistance to niclosamide occurred at an extremely low frequency (below the detection limit) (0≤mutational frequency<$4.10^{-9}$ at MIC×1) for all tested strains (MRSA 01, MRSA 15 (fusidic acid-resistant) and MRSA 16 (mupirocin-resistant)) compared to fusidic acid (mutational frequency: $3.10^{-7}$ at MIC×10 and ≥$4.10^{-5}$ at MIC×1) and to mupirocin and retapamulin. Results with the strain MRSA 01 are shown in Table 9.

TABLE 9

Frequencies of spontaneous mutations conferring resistance to niclosamide, fusidic acid, mupirocin and retapamulin with the strain MRSA 01. Average of 10 replicates.

| | | Niclosamide | Fusidic acid | Mupirocin | Retapamulin |
|---|---|---|---|---|---|
| Concentration | MIC × 1 | <$4 \times 10^{-9*}$ | ≥$4.10^{-5}$ | ≥$4.10^{-5}$ | ≥$4.10^{-5}$ |
| | MIC × 2 | <$4 \times 10^{-9*}$ | $2.10^{-5}$ | $8.10^{-8}$ | $3.10^{-7}$ |
| | MIC × 4 | <$4 \times 10^{-9*}$ | $1.10^{-6}$ | $1.10^{-8}$ | $2.10^{-8}$ |
| | MIC × 10 | <$4 \times 10^{-9*}$ | $3.10^{-7}$ | ≤$4.10^{-9}$ | <$4.10^{-9*}$ |

*Below the detection limit (no colony on plates)

As for MRSA 01, no colony grew on plates with niclosamide with the strains MRSA 15 and MRSA 16. These led to a mutation frequency <$3 \times 10^{-8}$ for MRSA 15 and <$1 \times 10^{-7}$ for MRSA 16 at MIC×1 (0.25 µg/ml), these differences in the detection limits being due to differences in the bacterial concentrations of overnight cultures.

Conclusions

Frequencies of spontaneous mutations conferring resistance to niclosamide in *Staphylococcus aureus* were much lower than frequencies of spontaneous mutations conferring resistance to fusidic acid, mupirocin and retapamulin in *Staphylococcus aureus*. This supports the use of niclosamide for cutaneous decolonization of *S. aureus*.

Example 4: *Propionibacterium acnes*

Evaluation of the probability of selecting spontaneous mutants of *Propionibacterium acnes* in the context of the chronic (long-term) antibiotic treatment of acne.

Microorganism

The strains of *P. acnes* used were CSS3288, CSS 3023, 998, and 1044 obtained from Luc Dubreuil.

Culture Medium

*P. acnes* strains are grown on *Brucella* blood agar with hemin and vitamin K [1], plates are incubated 48 to 72 hours at 35-37° C. under anaerobic conditions. *Brucella* blood agar with hemin and vitamin K was prepared as follows: sterile *Brucella* agar with hemin and vitamin K was tempered to 50-54° C. and the medium was supplemented with 5% lacked horse blood and poured in Petri dishes. Broth cultures are performed in Wilkins-Chalgren broth [2]. All cultures are done under anaerobic conditions in an anaerobic chamber [3]. Agar media was inoculated for single-colony isolation using sterile disposable loops.

Compounds Tested:

Niclosamide was tested as the halogenated salicylanilide. Comparator compounds were fusidic acid and retapamulin, both of which are frequently used in treatment of acne vulgaris.

Minimal Inhibitory Concentration (MIC)

The MICs of the antibacterial agents was determined by agar dilution. Bacteria were transferred into and grown in Wilkins-Chalgren Broth at 35-37° C. in the anaerobe chamber (86% $N_2$-7% $CO_2$-7% $H_2$) for 48 to 72 hours.

*Brucella* Blood Agar with hemin and vitamin K plates containing series of two-fold dilutions of antibacterial agents were prepared. The base agar was prepared and tempered to 50-54° C. Then the blood supplement and the antibiotics were added and the 7 ml were aseptically poured into six-well culture plates. Once the agar had solidified it was transferred into the anaerobe chamber for 24 hours before use to allow for pre-reduction. Twenty-five microliters of *P. acnes* culture containing $10^6$ CFU of were spotted in each well. The plates were incubated anaerobically for 72 hours at 35-37° C. The MIC is the lowest concentration that inhibits growth of *P. acnes*.

Spontaneous Mutation Frequency Assay

Cryopreserved bacteria were transferred into and grown in Wilkins-Chalgren at 35-37° C. in an anaerobe chamber (86% $N_2$-7% $CO_2$-7% $H_2$) for 72 hours.

Rucella Blood Agar with hemin and vitamin K plates containing 4× or 2×MIC (Minimal inhibitory concentration) of the test antibiotic were prepared. The base agar was prepared and tempered to 50-54° C. Then the blood supplement and the antibiotics were added and the plates were aseptically poured into petri dishes. Once the agar had solidified the plates were dried under a laminar-flow hood and then transferred into the anaerobe chamber for 24 hours before use to allow for pre-reduction.

The bacterial inoculums were taken from the Wilkins-Chalgren broth aiming to obtain a concentration close to $1 \times 10^8$ CFU/ml. These inoculums were then diluted in *Brucella* Broth and plate counted using an agar without antibiotic to enumerate the starting inoculums.

One hundred microliters of the adjusted inoculums were spread plated onto each of 25 antibiotic-containing agar plates while in the anaerobe chamber. These plates were then inverted and incubated for 72 hours at 37° C. Colonies growing on plates were transferred onto new antibiotic plates and re-incubated to confirm resistance to the antibiotic. Spontaneous mutational frequency was calculated as the ratio of resistant colonies that arose versus the starting bacterial inoculums counts Results and Discussion MICs of the antibacterial agents was as follows:
Fusidic acid: 4 µg/mL
Retapamulin: 0.016 µg/mL
Niclosamide: 0.5 µg/mL The spontaneous mutation frequencies for each of the tested compounds is shown in Table 10.

TABLE 10

Spontaneous mutation frequency against niclosamide and two comparators

| Compound | Strains | Frequency of mutation/ml |
|---|---|---|
| Fusidic acid MIC × 4 | CSS3288 | $6.15 \cdot 10^{-8}$ |
| | CSS3023 | $1.82 \cdot 10^{-8}$ |

TABLE 10-continued

Spontaneous mutation frequency against niclosamide and two comparators

| Compound | Strains | Frequency of mutation/ml |
|---|---|---|
| (16 µg/ml) | 998 | $9.17 \cdot 10^{-8}$ |
|  | 1044 | $7.21 \cdot 10^{-8}$ |
| Niclosamide | CSS3288 | $<2.70 \cdot 10^{-9}$ |
| MIC × 4 | CSS3023 | $<4.55 \cdot 10^{-9}$ |
| (2 µg/ml) | 998 | $<2.50 \cdot 10^{-9}$ |
|  | 1044 | $<1.92 \cdot 10^{-8}$ |
| Retapamulin | CSS3288 | $1.25 \cdot 10^{-8}$ |
| MIC × 4 | CSS3023 | $1.46 \cdot 10^{-8}$ |
| (0.064 µg/ml) | 998 | $2.17 \cdot 10^{-8}$ |
|  | 1044 | $1.09 \cdot 10^{-8}$ |

Conclusions

The two comparators fusidic acid and retapamulin have a frequency of mutation of resistance in the range of $1 \times 10^{-8}$. No resistant mutants to niclosamide were observed, thus frequency of mutation for niclosamide is less than $1 \times 10^{-9}$ at least 10 times lower than the two comparator compounds fusidic acid and retapamulin.

REFERENCES

[1] H.-P. Schau, "J. F. MacFaddin, Media for Isolation—Cultivation—Identification—Maintenance of Medical Bacteria, Volume I. XI+929 S., 163 Abb., 94 Tab. Baltimore, London 1985. Williams and Wilkins. ISBN: 0-683-05316-7," *J. Basic Microbiol.*, vol. 26, no. 4, pp. 240-240, 1986.
[2] T. D. Wilkins and S. Chalgren, "Medium for use in antibiotic susceptibility testing of anaerobic bacteria," *Antimicrob. Agents Chemother.*, vol. 10, no. 6, pp. 926-928, December 1976.
[3] S. M. Butler-Wu, E. M. Burns, P. S. Pottinger, A. S. Magaret, J. L. Rakeman, F. A. Matsen, and B. T. Cookson, "Optimization of Periprosthetic Culture for Diagnosis of Propionibacterium acnes Prosthetic Joint Infection," *J. Clin. Microbiol.*, vol. 49, no. 7, pp. 2490-2495, July 2011.
[4] E. J. C. Goldstein, D. M. Citron, C. V. Merriam, Y. A. Warren, K. L. Tyrrell, and H. T. Fernandez, "Comparative In Vitro Activities of Retapamulin (SB-275833) against 141 Clinical Isolates of Propionibacterium spp., Including 117 P. acnes Isolates," *Antimicrob. Agents Chemother.*, vol. 50, no. 1, pp. 379-381, January 2006.

Example 5: pH Effects on Antibacterial Activity

A study was carried out to determine the effect of pH on the antibacterial activity of niclosamide against *Staphylococcus aureus* in order to assess whether niclosamide is still active against *S. aureus* at pH levels close to those of the skin.

Methods

Microorganisms

Chosen for its relevance regarding bacterial skin infections, the methicillin-resistant *S. aureus* (MRSA) 01 strain was used. This strain is a community-acquired MRSA clinical isolate of USA 300 type, from a skin abscess.

This strain was conserved in Luria Bertani (LB) Broth supplemented with glycerol 15% (v/v) at −80° C., and reactivated by isolation on LB agar plates. It was then cultivated aerobically in Mueller Hinton (MH) Broth-cation adjusted at 37° C.

Assessment of the Effect of pH on the Antibacterial Activity of Niclosamide

The pH of Mueller-Hinton Broth cation-adjusted was adjusted with HCl 2M to 7, 6.5, 6, 5.5, 5, 4.5 and 5. Ten ml of medium for each pH were prepared. The pH of non-adjusted MHBII was equal to 7.4.

Each pH-adjusted samples were filtered on 0.2 µm filters before being used for the MIC determination assay. For each pH, minimal inhibitory concentrations (MICs) of niclosamide were determined according to CLSI criteria with a doubling dilution concentration range (16 to 0.008 µg/ml).

Bacterial culture was stopped in its exponential growth phase and plates were inoculated with the approximate concentration of $5 \times 10^5$ cells per well. Plates were incubated at 37° C. for 18 hours (*S. aureus*). Optical density at a wavelength of 600 nm was measured at the end of the incubation time. Inhibition was calculated as (Inhibition=1−$OD_{test}/OD_{no\ treatment}$) and MIC values were determined as the minimum concentration giving 100% inhibition.

The experiment was performed in triple biological replicates.

Results

The pH of each of the pH-adjusted media was checked after the addition of niclosamide in order to check that the addition of niclosamide did not have any influence on the pH. Measurements showed that the addition of niclosamide (16 µg/ml) in the pH-adjusted media had no influence on the pH (Table 11).

Figure 5:
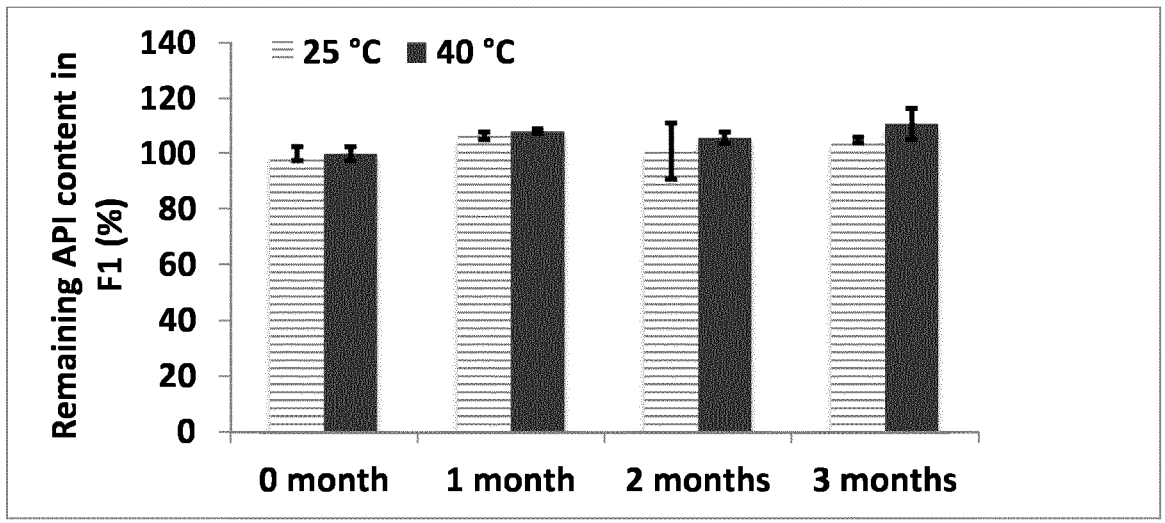
FIG. 5 shows the storage stability of non-aqueous gel compositions F1 and F4 comprising niclosamide after storage at 25° C. and 40° C. for 3 months.
Figure 5:
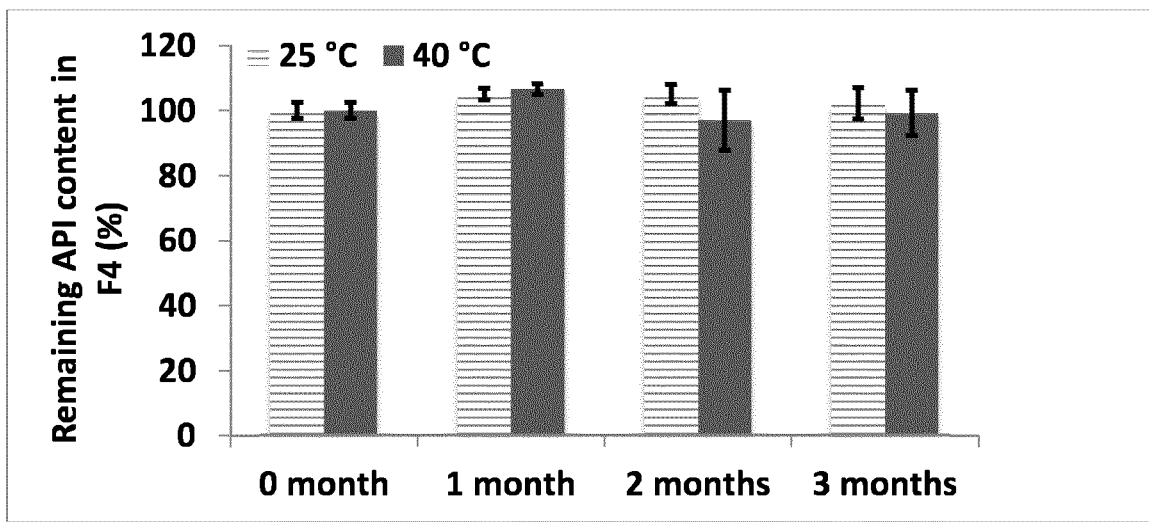

MRSA 01 grew equally well from pH 6 to pH 7.4 ($OD_{600} \approx 0.2$ in average in positive control wells) and slightly less in pH 5.5 ($OD_{600} \approx 0.1$ in average in positive control wells). However, the strain was inhibited by the lowest pH (pH 4 to pH 5) (FIG. 5).

MIC determinations showed that the inhibitory activity of niclosamide against MRSA 01 was increased when pH was decreased, with lower MICs (Table 11).

TABLE 11 pH and related MICs of niclosamide against MRSA 01 with the 3 different replicates.

| | Replicate 1 | | | Replicate 2 | | Replicate 3 | |
|---|---|---|---|---|---|---|---|
| | actual pH | pH after addition of niclosamide | MIC (µg/ml) | actual pH | MIC (µg/ml) | actual pH | MIC (µg/ml) |
| Not adjusted | 7.4 | 7.4 | 0.5 | 7.4 | 0.25 | 7.4 | 0.5 |
| pH 7.0 | 6.921 | 6.938 | 0.25 | 7.071 | 0.125 | 7.025 | 0.125 |
| pH 6.5 | 6.512 | 6.543 | 0.125 | 6.566 | 0.06 | 6.540 | 0.03 |

TABLE 11-continued pH and related MICs of niclosamide against MRSA 01 with the 3 different replicates.

| | Replicate 1 | | | Replicate 2 | | Replicate 3 | |
|---|---|---|---|---|---|---|---|
| | actual pH | pH after addition of niclosamide | MIC (µg/ml) | actual pH | MIC (µg/ml) | actual pH | MIC (µg/ml) |
| pH 6.0 | 5.893 | 5.954 | 0.06 | 5.955 | 0.06 | 5.980 | 0.016 |
| pH 5.5 | 5.569 | 5.616 | ≤0.03 | 5.547 | ≤0.008 | 5.530 | ≤0.008 |
| pH 5.0 | 5.070 | 5.095 | No | 5.068 | No | 5.008 | No |
| pH 4.5 | 4.569 | 4.589 | growth in | 4.568 | growth in | 4.550 | growth in |
| pH 4.0 | 4.076 | 4.105 | positive control. Strain inhibited by acidic pH | 4.044 | positive control. Strain inhibited by acidic pH | 4.023 | positive control. Strain inhibited by acidic pH |
| Initial bacterial concentration | | 2.E+05 cfu/ml | | | 2.E+05 cfu/ml | 3.E+05 cfu/ml | |

Conclusions

The maximal inhibitory effect of niclosamide was observed at pH 5.5, which is close to the pH of the skin.

Example 6: Non-Aqueous Gel Compositions

The formulations (F1 and F4) shown in Table 12 below were prepared as follows, wherein the amounts shown in Table 12 w/w.

TABLE 12

Gel formulations comprising niclosamide

| Component | F1 | F4 | Function |
|---|---|---|---|
| Niclosamide | 2 | 2 | Active agent |
| PEG 400 | 95.6 | 70.6 | Solvent |
| Carbomer 974P | 2.4 | 2.4 | Gel forming agent |
| Propylene glycol | — | 25 | Absorption enhancer |

Niclosamide 0.20 g, PEG 400 (9.56 g for F1 and 7.06 g for F4) and propylene glycol (2.5 g for F4) were weighed in blue cap bottles. The mixture was stirred at room temperature until a clear solution formed. 240 mg Carbomer 974P was then dispersed in the niclosamide PEG 400 solution. The dispersion was homogenized and degassed. The suspension was then heated at 70° C. and stirred mechanically at 250 rpm until a homogeneous dispersion formed after about 30 minutes. The final solution was then cooled to give the title non-aqueous gel compositions.

The final formulations were protected from light prior to further use.

Storage Stability of Formulations F1 and F4

The formulations tested where stored in aluminium tubes in incubators kept at 80% relative humidity and at 25 and 40° C.

FIG. 5, niclosamide is stable in the gel formulations F1 and F4 in the aluminium tubes with 104.8±1.0%/104.8±1.0% and 102.2±4.8%/99.2±7.0% remaining drug after three months' storage at both 25 and 40° C. respectively. No degradation products were observed by using HPLC analysis.

Light Stability of Formulations F1 and F4

Formulations F1 and F4 were exposed to ambient light for 24 hours. At predetermined time points, a small amount of exposed gel formulation was removed and analysed by HPLC.

Figure 6:
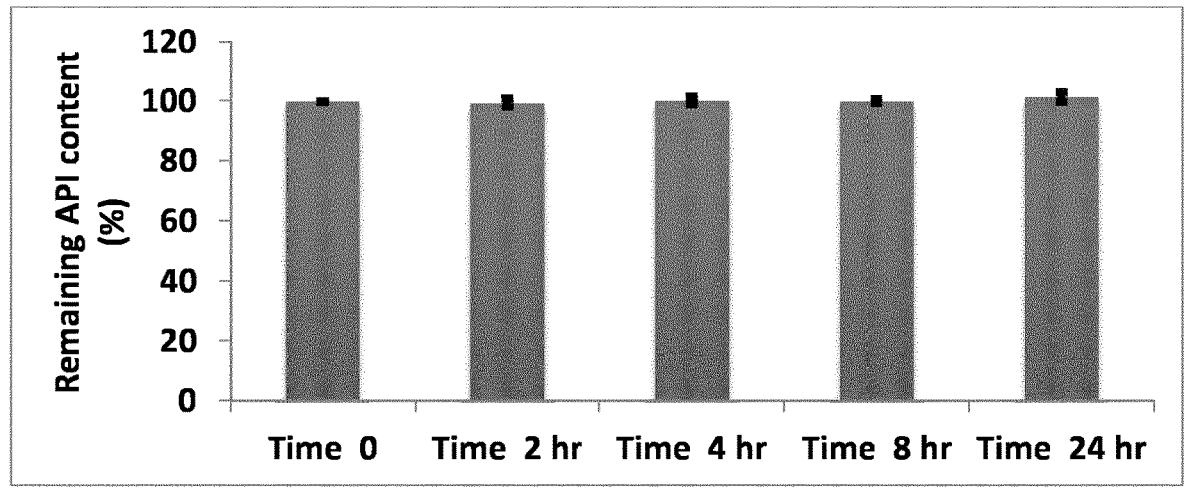
FIG. 6 shows the storage stability of non-aqueous gel compositions F1 and F4 comprising niclosamide after exposure to light for 24 hours. (n=3). Results are expressed as averages±SDs

As illustrated in FIG. 6, the non-aqueous gel compositions showed no signs of degradation after 24 hours exposure to light Skin Absorption and Penetration of the Different Topical Formulations.

Methods

Tissue Source

Human cadaver skin tissue was purchased from a tissue bank in the U.S. These tissues are recovered within 24 hours of death. Three lots of the dermatomed skin tissue were received. Donor demographics: tissue 4838 (average thickness=537 µm): sex=male, age=31, race=Caucasian and anatomical site=abdomen; tissue 4830 (average thickness=610 µm): sex=male, age=53, race=Caucasian and anatomical site=abdomen; tissue 4950 (average thickness=633 µm): sex=male, age=46, race=Caucasian and anatomical site=abdomen). The tissue was received in dry ice packaging. Tissue 4830 and tissue 4848 were stored in the freezer (−20° C.) for about 4.5 month; tissue 4950 was stored in the freezer (−20° C.) for about 3.5 months. All tissues were wetted with a Zyleris' proprietary storage medium to preserve barrier integrity during the storage. It was stored at −20° C. until use.

Skin Barrier Integrity Testing

After passing initial visual inspection, barrier integrity of the skin tissue was evaluated using trans-epidermal electrical impedance measurement (TEER measurement, Z value).

Measurement was conducted using a LCR meter at frequency of 100 Hz at room temperature. The measurement medium was 0.9% NaCl solution using a pair of stainless steel electrodes.

Prior to the screening study, electrical impedance value for the lot of skin tissue was evaluated. Due to potential lot-to-lot variation in donor age, gender, race, anatomical site and tissue harvest time, objective of the measurement was to establish threshold value for intact cadaver tissue for the lot to be used in the present skin absorption and penetration study. Twelve (12) tissue samples from selected spots from the lot were taken. Electrical impedance value (Z value) was measured. All reported Z values are net values after subtraction of the measurement medium blank (1.0 KOhms). It was found that large majority of the tissues for #4848 and 4950 had Z value 5.0 KOhms or greater; and for 4830 had Z value 7.0 KOhms or greater. For those tissues with visible defects, the Z value was found in the range of 0.1-0.5 KOhms. Therefore, 5.0 and 7.0 KOhms was used as threshold value for the three lots.

After the tissues were mounted on High-Throughput Screening (HTS) cells, skin integrity was measured before incubation at 32° C. Any tissue having Z value lower than 5.0 or 7.0 KOhms was discarded.

In Vitro Percutaneous Absorption and Penetration Study

The formulation screening study was carried out in Zyleris' High-Throughput Screening (HTS) station. This technology is developed based on the Franz Cell principle. The main technical feature includes a unique 81-cell screening station with ability to conduct various types of skin absorption and penetration study in each individual cell. It is fully validated against the standard Franz Cell technology. The skin samples after being washed with 1× phosphate buffer solution (PBS), pH 7.4 (10 mM phosphate, 137 mM NaCl, 2.7 mM KCl, pH 7.4) were mounted on diffusion cells in HTS station.

A total of 18 diffusion cells were used in the study. Each cell in the station has a diffusion area of 0.503 $cm^2$ (8 mm in diameter). Each individual cell is static Franz-Cell type. The receptor chamber was filled with 3.0 ml of 4% Bovine Serum Albumin (BSA) in water supplemented with 0.01% gentamicin sulfate. pH 7.1, which was vigorously and continuously mixed. The rational for using this medium is that 4% BSA can mimic the protein level in the blood and can easily be removed before analysis. In addition, this medium with 0.01% gentamicin is best in maintaining the skin integrity through the experiments, compared with normal PBS buffer. The temperature was set at 32±0.1° C. The tissue samples in the HTS cells were equilibrated at 32±0.1° C. for 1 hour before dosing. Each formulation was run in six replicates (N=6, Table 2). All laboratory activities with niclosamide were performed under yellow lights (λ=570 nm), because niclosamide is yellow and can absorb UV lights (λ=290-450 nm).

TABLE 13

Tissue number and tested groups

| Tissue Number | Tested groups |
|---|---|
| 4838 | F11, F12; F41, F42; |
| 4830 | F13, F14; F43, F44; |
| 4950 | F15, F16; F45, F46; |

Note:
F11-F16 are the replicates for formulation 1 (F1);
F41-F46 are the replicates for formulation 4 (F4).

At time points 2, 4, and 8 hours, the entire receptor fluid was collected and replaced with a fresh batch of receptor fluid (pre-incubated at 32° C.). The samples collected from the receptor medium were stored in a freezer (−20° C.).

At 24 hours, after removal of the skin tissue from the HT Franz Cell, the tissue surface and the donor chamber were carefully wiped with cotton swabs wetted by distilled water, followed by wiping with wet cotton swabs, then another cycle of wet cotton swabs to remove the "unabsorbed and unpenetrated" API. The standard tape-stripping method was used to remove the stratum corneum (SC) layer. It is a validated procedure that the first two tape strips were also counted as "non-absorbed API. The collected cotton swabs and first two strips were combined and extracted with 5.0 ml of DMSO/acetonitrile (50/50 v/v) at room temperature overnight using an orbit shaker.

The tape-stripping cycle was continued for additional 15 times for each skin sample to remove SC layer completely. The tape strips were combined and extracted with 5.0 ml of DMSO/acetonitrile (50/50 v/v) at room temperature overnight using an orbital shaker. For each stripping cycle, all applied tapes/tissues were lined up on a teflon plate. Then a hard rubber-lined roller was pressed against the tapes/tissues to apply equal pressure across all samples to ensure uniformity for each cycle and entire procedure. Then, the tape strip was removed in a quick motion from each tape/tissue pair. The tape strip was then collected. The extracts were collected and stored in a freezer (−20° C.).

After removal of SC layer, the remaining tissue was cut into small pieces and extracted with 5.0 ml of DMSO/acetonitrile (50/50 v/v) at room temperature overnight using an orbital shaker. The supernatants were collected and stored in a freezer (−20° C.). The receptor fluid was collected and stored in a freezer (−20° C.).

Drug Absorption Profile In Vitro Percutaneous Absorption and Penetration Study

Figure 7:
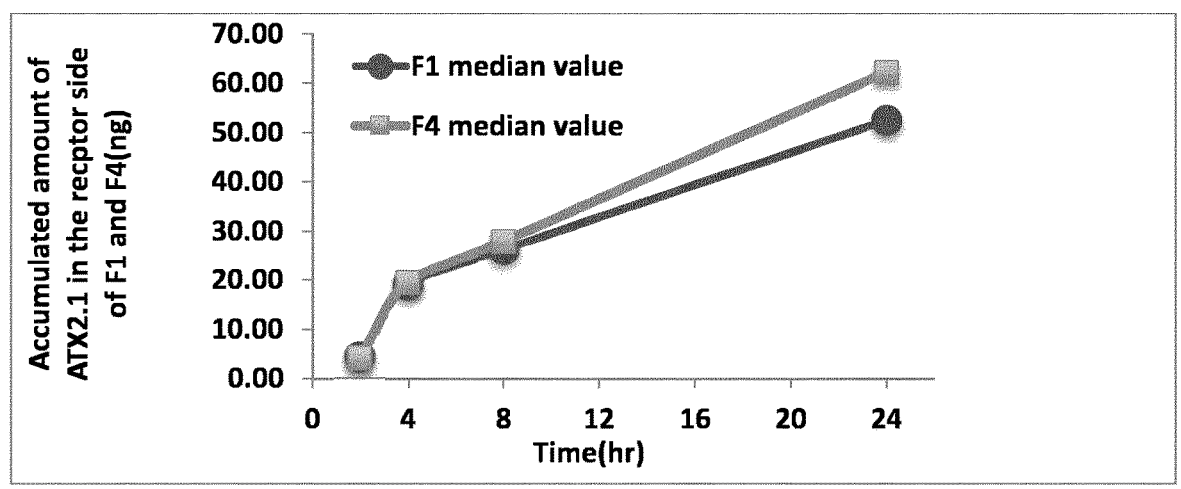
FIG. 7 shows the results of an in vitro percutaneous absorption and penetration study of the permeation of the non-aqueous gel compositions F1 and F4 comprising niclosamide across human skin with time (n=6).

The accumulated drug amount in the receptor fluid for F11-F16 and F41-F46 at 2, 4, 8 and 24 hours were calculated. In the F42 group, the accumulated amount of niclosamide was about 5-10 times of the values in other groups (F41, F43, F44, F45 and F46) at 2 hours. This may have been due to damage to the integrity of the skin during the experiment, although the skin integrity was validated prior to the experiment. Thus, the data of group F42 was discarded in the present calculation. Absorption curves of niclosamide were acquired by plotting the accumulated drug amount against time (FIG. 7). The equations, slope and $R^2$ were acquired by using the last three time points for linearity fitting in F1 and F4, assuming steady state was reached after 2 hours for F1 and F4.

The permeation parameters of niclosamide from different formulations across the human skin are set out in Table 13. The steady-state fluxes of niclosamide from different formulations were calculated based on the slope values from the absorption curves.

Data Analysis

The permeation data was analysed according to OECD guideline 428[1]. The steady-state flux ($J_s$), lag time ($T_L$), diffusion coefficient (D), skin/vehicle partition coefficient (K) and apparent permeation coefficient (Papp) are defined by equations (Eqs). (1-3)[2].

$$Js=(dQ/dt)_{ss}*1/A=DKC/h \tag{1}$$

$$D=h^2/6T_L \tag{2}$$

$$Papp=dQ/dt*1/A*1/C \tag{3}$$

For statistical calculations, student's t-test with two-tail type 1 was used and p<0.05 was considered significant.

1. Oecd, Test No. 428: Skin Absorption: In Vitro Method. OECD Publishing.
2. Cho, Y. A.; Gwak, H. S., Transdermal delivery of ketorolac tromethamine: effects of vehicles and penetration enhancers. *Drug development and industrial pharmacy* 2004, 30 (6), 557-564

The permeation parameters of niclosamide through human skin for formulations F1 and F4 were calculated using the equations above. According to the Eq. (1 and 3), the permeability is determined by the diffusion coefficient ($D_s$) and skin/vehicle partition coefficient (K), considering the applied dose is completely solubilized in three formulations (around 20 mg/ml). No significant difference was observed between F1 and F4 in the permeability values. These results indicate that the penetration enhancer propylene glycol did not significantly influence the absorption profile of niclosamide in F4.

TABLE 13

Average Permeation parameters of niclosamide through human skin for F1 and F4 (n = 6)

| Formulations | Area (cm²) | Js(ng * cm$^{-2}$ * h$^{-1}$) | Concentration (mg * ml$^{-1}$) | Permeability (*10$^{-7}$ * cm * hr$^{-1}$) | $T_L$ (hr) | Ds (10³ * μm² * h$^{-1}$) | K(skin/donor) | h (μm) |
|---|---|---|---|---|---|---|---|---|
| F1 | 0.5 | 3.75 | 21.02 | 1.78 | 2 | 29.48 | 3.64 | 537-633 |
| F4 | 0.5 | 7.02 | 22.38 | 3.14 | 2 | 32.30 | 6.07 | 537-633 |

Note:
The steady-state flux ($J_s$), lag time ($T_L$), diffusion coefficient ($D_s$), skin/vehicle partition coefficient (K) and apparent permeation coefficient ($P_{app}$).

FIG. 7 shows the median accumulated niclosamide in the receptor fluid for the tested compositions F1 and F4.

Drug Penetration Profile after 24 Hour Application

The distribution of niclosamide in the skin samples after 24 hours, i.e. the amount expressed as ng and % of the applied dose present in receptor fluid, viable epidermis and dermis, stratum corneum was determined. The amount of niclosamide on skin surfaces and on the walls of the donor chambers was also determined, and was considered to be non-penetrated drug. The average of the results for formulations F1 and F4 results are shown in Table 14.

TABLE 14

Average drug penetration profile of niclosamide through human skin after applying F1 and F4 for 24 hr (n = 6)

| Formulation | Receptor fluid (ng) | Non-penetrated drug (ng) | Stratum corneum (ng) |
|---|---|---|---|
| F1 | 60.68 | 100359.66 | 3014.82 |
| SD | 11.62 | 40278.62 | 3037.78 |
| F4 | 111.01 | 80194.08 | 1808.92 |
| SD | 68.34 | 30324.72 | 2429.59 |

| Formulation | Epidermis and dermis (ng) | Receptor fluid % | Stratum corneum % | Epidermis and dermis % |
|---|---|---|---|---|
| F1 | 5070.80 | 0.06 | 2.56 | 7.19 |
| SD | 5983.05 | 0.02 | 2.36 | 9.74 |
| F4 | 7338.23 | 0.15 | 1.84 | 8.22 |
| SD | 6025.55 | 0.11 | 2.10 | 7.69 |

No significant difference was observed between F1 and F4 with respect to the amount and percentage of niclosamide in the receptor fluid. This result is consistent with the permeability data discussed above. Therefore, the permeation enhancer propylene glycol at 25% by weight in F4 did not significantly influence the absorption profile of niclosamide from the gel composition in this study. Furthermore, no statistically significant differences were observed between formulations F1 and F4 in the drug distribution in the stratum corneum as well as in the dermis and epidermis ($p > 0.05$).

Active Drug Exposure in the Human Skin Tissue

According to previous research, the average thickness of stratum corneum layer of adult abdomen is about 22.38 μm (Holbrook, K. A.; Odland, G. F., Regional differences in the thickness (cell layers) of the human stratum corneum: an ultrastructural analysis. *Journal of Investigative Dermatology* 1974, 62 (4), 415-422.). The thickness of the epidermis and dermis was calculated by subtracting the stratum corneum layer from the thickness of the whole piece of skin (Table 14). Thus, the volume of stratum corneum and epidermis plus dermis can be calculated. The concentrations of niclosamide in different skin layers can be calculated by using the deposited niclosamide amount and the calculated volume. As shown in Table 15, 5,000-10,000 times the MIC of niclosamide was present in the stratum corneum layer after applying F1 (220.17 μg/cm²) and F4 (191.01 μg/cm²) for 24 hours.

688 times and 975 times the MIC of niclosamide was present in the epidermis and dermis after applying F1 (220.17 μg/cm²) and F4 (191.01 μg/cm²) for 24 hr. It is generally believed that 10× the MIC of drug exposure for 24 hours will be sufficient to provide effective killing of bacteria. These results suggest that the present gel formulations will be highly potent topical antibacterial.

TABLE 15

Average values of active drug exposure in human skin tissue after applying F1 and F4 for 24 hr (n = 6)

| Formulation | Active drug concentration in stratum corneum layer (ng/ml) | Active drug concentration in Epidermis and dermis layer (ng/ml) | Fold MIC[1] in stratum corneum layer | Fold MIC[1] in epidermis and dermis layer |
|---|---|---|---|---|
| F1 | 2555935.33 | 172051.30 | 10223.74 | 688.21 |
| SD | 2575408.91 | 202371.31 | 10301.64 | 809.49 |
| F4 | 1533587.61 | 243810.63 | 6134.35 | 975.24 |
| SD | 2059788.97 | 197418.26 | 8239.16 | 789.67 |

[1]MIC, minimum inhibitory concentration (ng/ml) against methicillin-resistant *staphylococcus aureus* (MRSA) = 250

Synergy Between Niclosamide and PEG (In Vivo Data)

*Staphylococcus aureus* 43484 is a CA-MRSA clinical isolate from a skin abscess of USA300 type (ST8-t008-IV, PVL⁺) (Statens Serum Institute, Copenhagen, Denmark). Bacterial suspensions for inoculation of mice were prepared from overnight cultures on 5% blood agar plates (SSI Diagnostica, Hillerød, Denmark) immediately before inoculation by suspending colonies in sterile 0.9% saline to 9 $\log_{10}$ CFU/mL. (MRSA 01).

Experimental Skin Wound Infection Model

The experiments were conducted essentially as described in (Vingsbo Lundberg C, Frimodt-Møller N. Efficacy of topical and systemic antibiotic treatment of meticillin-resistant *Staphylococcus aureus* in a murine superficial skin wound infection model. *Int. J Antimicrob. Agents.* 2013 September; 42(3):272-5. doi: 10.1016/j.ijantimicag.2013.05.008. Epub 2013 Jul. 6. PubMed PMID: 23837927.

Female BALB/c mice, 10-12 weeks old were anaesthetised and shaved on a 2-3 cm² skin area of the lower back. A disposable dermal curette (Integra, York, PA, USA) was used to induce a minor superficial skin wound on a 1 cm² area, which was inoculated with 7 $\log_{10}$ CFU of bacteria.

Mice were sacrificed and the entire infected skin area with underlying tissue was cut out and homogenised in 1 mL of saline using a Dispomix® Drive (Medic Tools AG, Zug, Switzerland). Tissue homogenates were serially diluted in saline containing 0.1% Triton X-100 (T-8787; Sigma-Aldrich Inc., St Louis, MO). Then, 20 µL spots were applied in duplicate to NaCl agar supplemented with polymyxin B (SSI Diagnostica). Plates were incubated at 35° C. in ambient air for 20-48 h.

Figure 8:
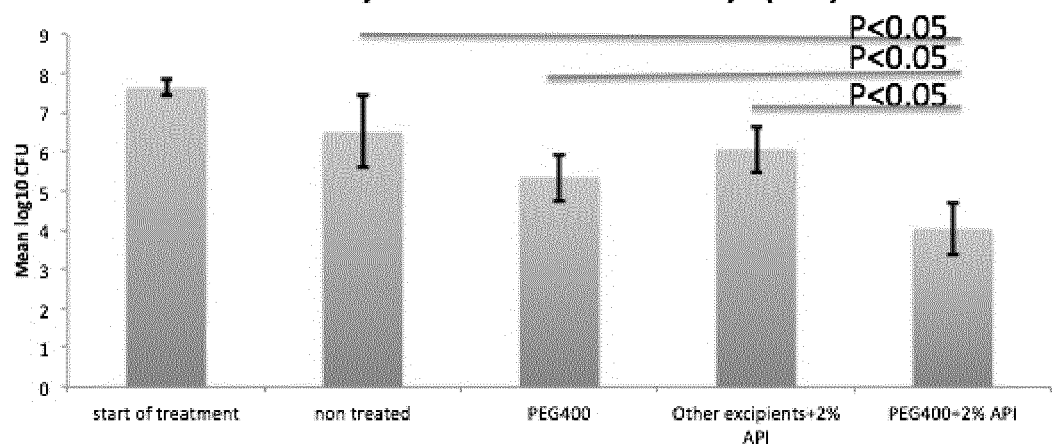
FIG. 8 shows the reduction of MRSA Colony Forming Units (CFU) on mouse skin following twice daily topical application of formulation F1 for three days compared to a positive control, application of PEG 400 alone, and the topical application of a comparator composition comprising an aqueous cream composition comprising 2% by weight niclosamide" The data shows the beneficial effect of niclosamide and the PEG 400 when used in combination in the gel composition.

Treatment was initiated the day after inoculation and mice were treated twice daily for 3 days, with 5-6 mice in each treatment group. Briefly, 0.05 mL of antibiotic formulation was applied topically to the lesion area. Skin samples were collected the day after completed treatment for CFU determination. Carry-over effect was minimised by performing the CFU determinations >18 h after the last treatment and homogenizing, diluting and plating the samples immediately. The mice were tested with the following compositions: F1 in Table 12 (see "PEG 400+2% API" in FIG. 8 (a gel composition of the invention));

The composition F1 but excluding niclosamide (see "PEG 400" in FIG. 8 (a comparative composition))

A 2% niclosamide aqueous cream composition containing the excipients shown in Table 16 (see "other excipients+2% API in FIG. 8; (a comparative composition))

TABLE 16

| Comparative composition | |
|---|---|
| Excipient | % (w/w) |
| Niclosamide | 2 |
| Polysorbate 80 | 5 |

TABLE 16-continued

| Comparative composition | |
|---|---|
| Excipient | % (w/w) |
| Cetostearyl alcohol | 10 |
| Paraffin oil | 25 |
| Glycerin | 10 |
| Butylated Hydroxyanisole | 0.1 |
| Water | 47.9 |

The MRSA reduction on mice skin after twice daily treatment for three days results are illustrated in FIG. 8. The results show that the non-aqueous gel composition comprising niclosamide and PEG 400 exhibited an improved effect compared to the use of PEG 400 alone or the cream formulation comprising niclosamide alone.

Concentrated polyethylene glycol 400 (PEG400) solutions have been reported (Antibacterial Agents and Chemotherapy, 24(3), 409-412 (1983)) to have some antibacterial activity against bacteria such as *Klebsiella pneumoniae, Pseudomonas aeruginosa, Escherichia coli* and *Staphylococcus aureus*. The experiments reported were performed in an aqueous media and the effect of PEG 400 was believed to be attributed to two effects: lowering of water activity and, superimposed on this, the specific action of PEG 400 on bacterial cells.

The apparent synergistic effect between niclosamide and PEG in reducing MRSA on the mouse skin was unexpected because the tested compositions were non-aqueous gels topically applied to the mouse skin under essentially non-aqueous conditions.

Example 7: Further Non-Aqueous Topical Compositions

The non-aqueous topical compositions shown in Tables 17, 18 and 19 were prepared

TABLE 17

| | Composition | | | |
|---|---|---|---|---|
| | Formulation D | Formulation E | Formulation F | Formulation G |
| | Appearance | | | |
| Raw material INCI or PhEur name (trade name) | Very shiny, soft yellow ointment % (w/w) | Shiny rather hard yellow ointment, becomes soft upon shearing % (w/w) | Very shiny hard yellow ointment, becomes soft upon shearing % (w/w) | Slightly shiny hard yellow ointment, becomes soft upon shearing % (w/w) |
| Hydrophilic Phase | | | | |
| Niclosamide anhydrous | 2.0 | 2.0 | 2.0 | 2.0 |
| Macrogol 400 | 30.0 | 20.0 | 27.5 | 30.0 |
| Propylene glycol | 25.0 | 15.0 | 17.5 | 15.0 |
| Ethoxydiglycol (Transcutol) | | 15.0 | 5.0 | 15.0 |
| Glycerol | 19.7 | | | |
| Hydroxyethyl cellulose (Natrosol 250G Pharm) | 0.25 | | | |
| Hydrophobic Phase and emulsifiers | | | | |
| Polysorbate 80 | | 1.0 | 1.0 | 1.0 |
| Ceteareth-20 (Cetomacrogol 1000-PA) | 6.0 | | | |
| Caprylocaproyl Macrogol 8 glycerides (Labrasol) | 10.0 | | | |

TABLE 17-continued

| | Composition | | | |
|---|---|---|---|---|
| | Formulation D | Formulation E | Formulation F | Formulation G |
| | Appearance | | | |
| Raw material INCI or PhEur name (trade name) | Very shiny, soft yellow ointment % (w/w) | Shiny rather hard yellow ointment, becomes soft upon shearing % (w/w) | Very shiny hard yellow ointment, becomes soft upon shearing % (w/w) | Slightly shiny hard yellow ointment, becomes soft upon shearing % (w/w) |
| Steareth-21 (Brij S721) | | 5.0 | 5.0 | 5.0 |
| Steareth-2 (Brij S2) | | 5.0 | 5.0 | 5.0 |
| Macrogol stearyl ether (Arlamol PS11E) | | | 5.0 | |
| Paraffin, liquid | | 10.5 | 5.5 | 6.5 |
| Medium chain triglycerides | | 6.0 | 6.0 | |
| Paraffin, Type 5205, hard | | 6.5 | 6.5 | 6.5 |
| Cetostearyl alcohol (Kolliwax CSA 50) | 7.0 | 12.0 | 12.0 | 12.0 |
| Glyceryl stearate, Type II (Kolliwax GMS II) | | 2.0 | 2.0 | 2.0 |

TABLE 18

| | Composition | | |
|---|---|---|---|
| | Formulation H | Formulation I | Formulation J |
| | Appearance | | |
| Raw material INCI or PhEur name (trade name) | Shiny rather hard yellow ointment, becomes soft upon shearing, liquefies at skin temp. % (w/w) | Very shiny very soft yellow ointment, becomes softer upon shearing % (w/w) | Soft shiny yellow ointment, becomes softer upon shearing % (w/w) |
| Hydrophilic Phase | | | |
| Niclosamide, anhydrous | 2.0 | 0.5 | 0.5 |
| Macrogol 400 | 10.0 | 20.0 | 10.0 |
| Propylene glycol | 20.0 | 10.0 | 20.0 |
| Ethoxydiglycol (Transcutol) | 15.0 | 15.0 | 15.0 |
| Hydrophobic Phase and emulsifiers | | | |
| Polysorbate 80 | 1.0 | 1.0 | 1.0 |
| Steareth-21 (Brij S721) | 5.0 | 5.0 | 5.0 |
| Steareth-2 (Brij S2) | 5.0 | 5.0 | 5.0 |
| Paraffin, liquid | 11.5 | 14.5 | 14.5 |
| Medium chain triglycerides | 10.0 | 10.0 | 10.0 |
| Paraffin, Type 5205, hard | 6.5 | 5.0 | 5.0 |
| Cetostearyl alcohol (Kolliwax CSA 50) | 12.0 | 12.0 | 12.0 |
| Glyceryl stearate, Type II (Kolliwax GMS II) | 2.0 | 2.0 | 2.0 |
| Carbomer 974P (Carbopol 974P) | | | |

TABLE 19

| Raw material INCI or PhEur name (trade name) | Composition Formulation B Appearance Dark yellow clear gel % (w/w) |
|---|---|
| Niclosamide, anhydrous | 4.0 |
| Macrogol 400 | 93.6 |
| Carbomer 974P (Carbopol 974P) | 2.4 |

The ointment formulations D, E, F, G, H, I and J set out in Tables 17 and 18 were prepared as non-aqueous emulsions using the following general method.

The hydrophilic phase of the emulsion and the anhydrous niclosamide (see under heading "hydrophilic phase" in Tables 17 and 18) were mixed together with stirring in a vessel to form a solution of the niclosamide in the hydrophilic phase. Generally the hydrophilic phase was heated gently at a temperature of about 60 to 75° C. (generally at about 70° C.) to aid dissolution of the niclosamide.

A hydrophobic phase comprising the oils and emulsifiers under the heading "Hydrophobic phase and emulsifiers" were mixed together by stirring in a heated vessel. The temperature was about 60 to 75° C. (generally at about 70° C.).

The hydrophobic phase and the hydrophilic phases were mixed together with gentle stirring so as to avoid phase separation and the mixture was cooled to a temperature of about 40 to 50° C. The mixture was then homogenised to give the final composition.

The gel formulation B was prepared using an analogous method to that described for the preparation of the gel composition F1 described above in Example 6.

The appearance and some of the properties of the resulting compositions is described in the row marked "Appearance" in Tables 17 and 18.

Example 8: Dermal Tolerance and PK Study in Mini-Pigs

Aim

The aim of the study was to assess the local tolerability of the non-aqueous dermal niclosamide formulations B, D, E, F, G, H, I and J in Tables 17 and 18. The study also assessed the distribution of niclosamide into the dermis and epidermis following 2 days and 28 days of application.

Reason for the Choice of Animal Species, Route of Administration and Doses

The skin of pigs and Mini-pigs has been extensively described and is considered useful for dermatological-related evaluations and dermal toxicity testing as the skin architecture, development and function was considered to resemble human skin closely.

Animals

The study was performed in 3 male and 3 female Göttingen SPF mini-pigs from Ellegaard Göttingen Mini-pigs A/S, DK-4261 Dalmose, Denmark. At the start of the acclimatization period, the animals were approximately 6 months old and the body weight was 12.1 to 13.4 kg. An acclimatization period of at least 1 week was allowed, during which the animals were observed daily.

Dosing

The compositions were applied dermally to a test area on the skin of the mini-pigs at an applied daily dose of 10 mg/m$^2$ niclosamide for 28 days. All test fields were semi-occluded with Mefix® (Mölnlycke Health Care, Sweden), allowing the sites to "breathe" while keeping the test substance in place. The Mefix® was kept in place with adhesive tape (Tensoplast, BSN medical, Germany) for 6 hours±30 minutes after application to ensure that the compounds were absorbed into the skin.

Skin Biopsies and PK Analysis

Skin biopsies were taken from the mini-pigs on Day 28. Subdermal tissue was removed and the biopsies were placed in an Eppendorf tube and immersed in a 55° C. water bath for 5 minutes. After that, each biopsy was divided between the epidermal and dermal layer of the skin with tweezers. The weight of the dermal biopsy was recorded and the epidermal biopsy weight was estimated from weighing of epidermal slices from 6 mm biopsies of pig skin. The epidermal and the dermal biopsy samples were placed in separate Eppendorf tubes and snap-frozen in liquid nitrogen prior to analysis.

The skin biopsies were analysed using a validated HPLC method to assess the concentration of niclosamide in the dermis and epidermis.

Blood Sampling

Blood samples were also taken at day 28 and plasma from the blood was analysed for niclosamide concentration.

Skin Reactions

Reactions at the application sites were observed daily after dosing and on the day of necropsy. Any dermal irritation was scored according to the OECD Guideline for Testing of Chemicals No. 404, adopted 24 Apr. 2002: "Acute Dermal Irritation/Corrosion" as follows:

| Erythema and Eschar Formation | Grade |
|---|---|
| No erythema | 0 |
| Very slight erythema (barely perceptible) | 1 |
| Well-defined erythema | 2 |
| Moderate to severe erythema | 3 |
| Severe erythema (beet redness) to eschar formation preventing grading of erythema | 4 |

| Edema Formation | Grade |
|---|---|
| No edema | 0 |
| Very slight edema (barely perceptible) | 1 |
| Slight edema (edges of area well-defined by definite raising) | 2 |
| Moderate edema (raised approximately 1 mm) | 3 |
| Severe edema (raised more than 1 mm, extending beyond area of exposure) | 4 |

Any other reaction was recorded and the area involved scored as follows:

| Size of area of other reactions | Score |
|---|---|
| <10% of test area | 0 |
| 10-25% of test area | 1 |
| 26-50% of test area | 2 |
| 51-75% of test area | 3 |
| 76-100% of test area | 4 |

Results

Skin Reactions

All dermal formulations tested were well tolerated in all mini-pigs following repeated dosing for 28 days.

In a comparison of the results of all the tested topical formulations, the following observations were made.

The scoring of skin reactions revealed that formulation B (non-aqueous gel formulation) only caused slight erythema one day in one pig (Pig No. 6) indicating that Formulation B was extremely well tolerated.

Formulations F and G only revealed scores up to well defined in 3 pigs (Pig Nos. 1, 2, and 3) and up to slightly in 3 pigs (Pig Nos. 4, 5, and 6), meaning that all pigs were affected to a minor degree by formulations F and G. Formulation I affected three pigs (Pig Nos. 1, 4, and 5) up to slight erythema, while two pigs (Pig Nos. 2 and 3) were affected up to a moderate degree in erythema.

Formulations D, E, H, and J showed scores of up to moderate in all pigs, however the female pigs would never exceed scores of slight erythema. None of the formulations caused edema in any of the pigs throughout the study.

In conclusion, the anhydrous formulations dosed topically daily for 28 days in the local tolerance study in 3 female and 3 male mini-pigs revealed erythema macroscopically of slight to a moderate degree, however the erythema disappeared within 9 days of the last dosing. Additionally histopathology did not find any observable reactions caused by application of the formulations. Gel formula B was particularly well tolerated.

Bioanalysis in the Dermis, Epidermis and Plasma

Bioanalysis showed that niclosamide was mainly located in the epidermis, and the dermis, with only a slight concentration in the plasma (generally less than 0.651 ng/mL), indicting a highly local effect. The formulations that were observed to have the highest exposure in the epidermis and dermis, were formulations B (all pigs) and H (in four pigs).

Figure 9:
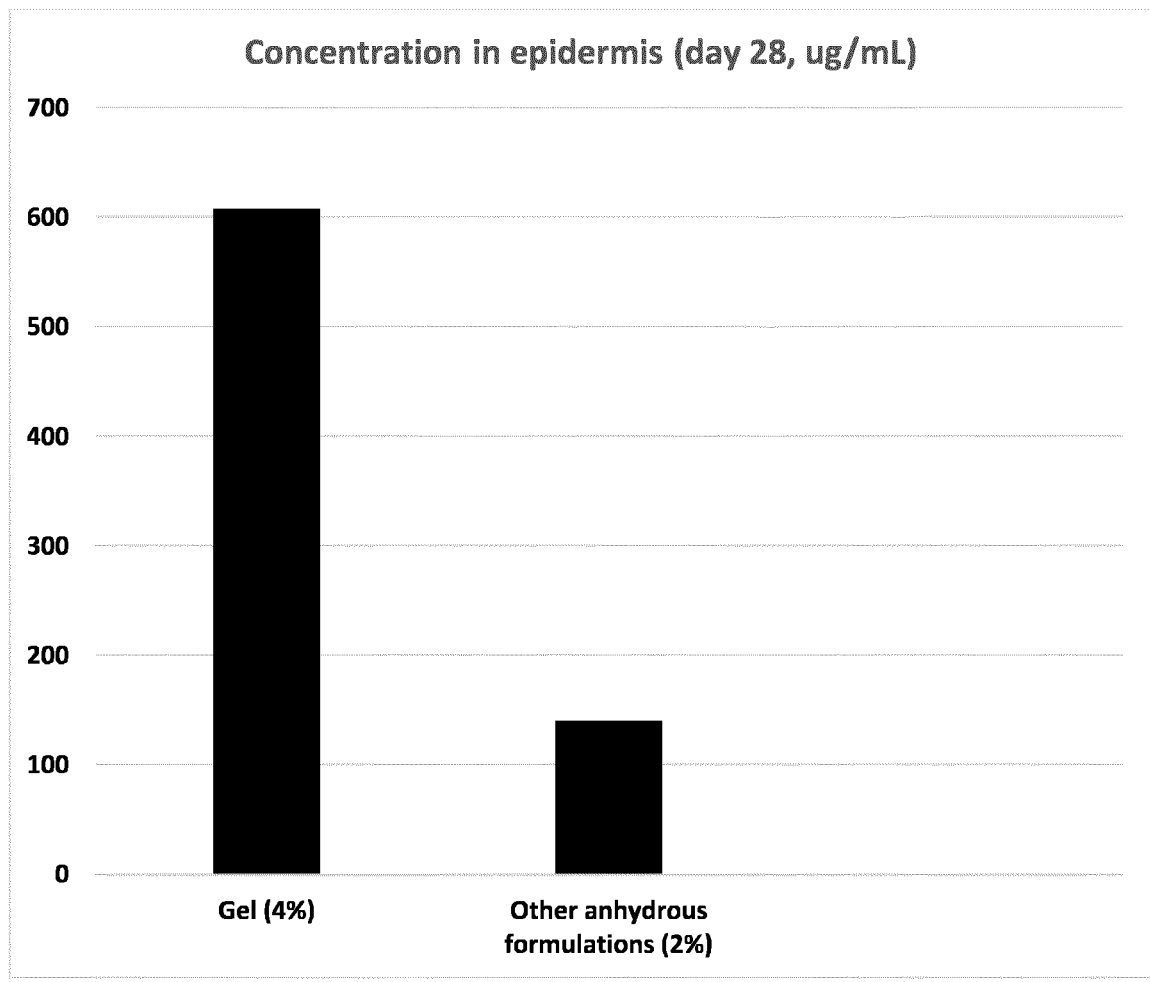
FIG. 9 shows the concentration of niclosamide in the epidermis of a mini-pig treated topically for 28 days with a gel composition comprising 4% by weight niclosamide, PEG 400 and a carbomer (Formulation B) and the mean concentration of niclosamide in the epidermis obtained with the other non-aqueous compositions tested containing 2% by weight niclosamide (Formulations D, E, F, G and H, labelled "other anhydrous formulations" in FIG. 9). The y-axis in FIG. 9 shows the niclosamide concentration in the epidermis in µg/mL.

FIG. 9 compares the concentration of niclosamide in the epidermis at day 28 with the gel formulation B with the average concentration observed for the ointment formulations D, E, F, G and H. The concentration of niclosamide in the epidermis from the gel Formulation B was significantly higher than that resulting from the other formulations tested.

The invention is further illustrated by the following numbered clauses:

1. A non-aqueous topical composition comprising:
   (i) a halogenated salicylanilide, or a pharmaceutically acceptable salt thereof; and
   (ii) greater than 60% by weight of a polyethylene glycol (PEG), wherein the average molecular weight of the PEG is less than 600.

2. The composition of clause 1 wherein the composition is a non-aqueous gel composition comprising:
   (i) a halogenated salicylanilide, or a pharmaceutically acceptable salt thereof;
   (ii) greater than 60% by weight of a PEG, wherein the average molecular weight of the PEG is less than 600; and
   (iii) a gel-forming agent.

3. The composition of clause 2 wherein the gel-forming agent is a gel-forming polymer, for example a hydrophilic gel-forming polymer 4. The composition of clause 2 or clause 3, wherein the gel-forming polymer is a thermo-reversible gel-forming polymer, for example carrageenan, gelatin, agar, agarose, pectin or a cellulose derivative.

5. The composition of clause 2, wherein the gel-forming polymer is an ionotrophic gel-forming polymer, for example chitosan or an alginate.

6. The composition of clause 2, wherein the gel-forming polymer is selected from gelatin; agar; agarose; pectin; carrageenan; chitosan; alginate; starch; starch components; tragacanth gum; xanthan gum; gum arabic; guar gum; gellan gum; locust bean gum; a polyurethane; a polyether polyurethane; cellulose; a cellulose ether; a cellulose ester, a cellulose acetate, a cellulose triacetate; cross-bonded polyvinyl alcohol; a polymer or copolymer of acrylic acid, hydroxyalkyl acrylates, hydroxyethyl acrylate, diethylene glycol monoacrylate, 2-hydroxypropylacrylate or 3-hydroxypropyl acrylate; a carbomer; a polymer or copolymer of methacrylic acid, hydroxyethyl methacrylate, diethyleneglycol monomethacrylate, 2-hydroxypropyl methacrylate, 3-hydroxypropyl methacrylate or dipropylene glycol monomethylacrylate; a vinylpyrrolidone polymer; a polymer or copolymer of acrylamide, N-methylacrylamide, N-propylacrylamide or methacrylamide, N-isopropylmethacrylamide or N-2-hydroxyethylmethacrylamide; a poloxamer; and gels comprising cross-linked polyalkylene glycols and combinations thereof.

7. The composition of clause 2 wherein the gel-forming polymer is a carbomer.

8. The composition of clause 7, wherein the carbomer is selected from carbomer 910, carbomer 934P, carbomer 940GE, carbomer 941GE, carbomer 971P and carbomer 974P.

9. The composition of clause 7, wherein the carbomer is carbomer 974P.

10. The composition of any of clauses 2 to 9, wherein the gel-forming agent is present in an amount of up to about 10% by weight of the composition, for example from 1% to 5% by weight of the composition.

11. The composition of any preceding clause wherein the PEG has an average molecular weight of from about 200 to about 600.

12. The composition of clause 11, wherein the PEG is PEG 400.

13. The composition of any preceding clause wherein the PEG is present in an amount of from about 70% to about 98% by weight of the composition, for example from 80% to 95% by weight.

14. The composition of any preceding clause wherein the halogenated salicylanilide is a compound of the formula (I):

15.

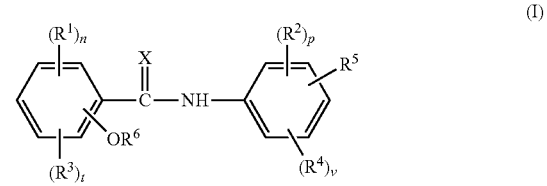

(I)

wherein
X is O or S;
$R^1$ and $R^2$ are at each occurrence independently selected from halo;
$R^3$ and $R^4$ are at each occurrence independently selected from H, $C_{1-6}$-alkyl, —$OR^{41}$, —$NO_2$ and —CN;
$R^5$ is H or -$L^1$-$R^7$;
$R^6$ is H or —$C(O)R^{42}$;
$L^1$ is selected from a bond, O, S, or —$(CR^{43}R^B)_o$—, wherein o is 1 or 2;
$R^7$ is phenyl, unsubstituted or substituted with 1, 2, or 3 groups selected from halo, $C_{1-4}$-alkyl, —$OR^{44}$, —$NO_2$ and —CN;
$R^{41}$, $R^{42}$, $R^{43}$ and $R^{44}$ are at each occurrence independently selected from H and $C_{1-4}$-alkyl;
$R^B$ is at each occurrence selected from H, $C_{1-4}$-alkyl and —CN;

n and p are each independently selected from 0, 1, 2, 3 or 4, with the proviso that n+p is at least 1;

t and v are independently selected from 0, 1 and 2;

or a pharmaceutically acceptable salt thereof.

16. The composition of any preceding clause wherein the halogenated salicylanilide is selected from the group consisting of niclosamide, closantel, oxyclozanide and rafoxanide, or a pharmaceutically acceptable salt thereof.

17. The composition of clause 16, wherein the halogenated salicylanilide is niclosamide, or a pharmaceutically acceptable salt thereof.

18. The composition of any preceding clause wherein the halogenated salicylanilides is present in an amount of up to up to 10% by weight of the composition, for example from 0.05 to 4.5% by weight of the composition.

19. The composition of any preceding clause wherein the composition comprises a polar a polar organic solvent having a dielectric constant of from about 10 to about 45, for example a dielectric constant of from about 10 to about 20 when measured at 20-25° C.

20. The composition of clause 19, wherein the polar organic solvent is present in an amount of up to 35% by weight of the composition, for example from 1% to 30% by weight.

21. The composition of any preceding clause wherein the composition comprises an absorption enhancer.

22. The composition of clause 21, wherein the absorption enhancer is selected from a sulfoxide; dimethylacetamide; dimethylformamide; a urea; a fatty alcohol; a polyol (for example glycerol, a glycol, such as propylene glycol or hexylene glycol or; 1-dodecylazacycloheptan-2-one; an essential oil; a pyrrolidone; an oxazolidinone; and a surfactant (for example a non-ionic, anionic or cationic surfactant), optionally the absorption enhancer is propylene glycol or glycerol, suitably the absorption enhancer is propylene glycol.

23. The composition of clause 21 or clause 22, wherein the absorption enhancer is present in an amount of up to 35% by weight of the composition, for example from 1% to 30% by weight of the composition.

24. A non-aqueous gel composition comprising
 (i) 1 to 3% by weight of niclosamide, or a pharmaceutically acceptable salt thereof;
 (ii) 94 to 98% by weight of PEG 400; and
 (iii) 1 to 3% by weight of a carbomer, for example carbomer 974P.

25. The composition of any preceding clause, wherein the composition does not comprise ethanol.

26. The composition of any preceding clause, wherein the halogenated salicylanilide is dissolved in the composition.

27. The composition of any preceding clause, wherein the composition provides a local pH of less than 5.5 at the site of infection following topical application of the composition, for example a local pH in the range of about 4.5 to about 5.5.

28. A composition of any of clauses 1 to 27 for use in the topical prevention or treatment of an infection or disease caused by Gram-positive bacteria.

29. The composition of any of clauses 1 to 27 for the use according to clause 28, wherein the Gram-positive bacteria develops spontaneous mutations which confer resistance to the halogenated salicylanilide at a frequency of less than $10^{-6}$ at the minimum inhibitory concentration (MIC) of the halogenated salicylanilide to the Gram-positive bacteria.

30. The composition for the use according to clause 29, wherein the Gram-positive bacteria develops spontaneous mutations which confer resistance to the halogenated salicylanilide at a frequency of less than $4 \times 10^{-9}$, for example less than $10^{-9}$ at the MIC of the halogenated salicylanilide to the Gram-positive bacteria.

31. The composition for the use according to any of clauses 28 to 30, wherein the Gram-positive bacteria is selected from *Staphylococcus* spp., *Streptococcus* spp. or *Propionibacterium* spp.

32. The composition for the use of any of clauses 28 to 31, wherein the Gram-positive bacteria is not a *Propionibacterium*.

33. The composition for the use according to any of clauses 28 to 32, wherein the infection or disease is selected from the group consisting of impetigo, bacterial conjunctivitis, atopic dermatitis, sycosis barbae, superficial folliculitis, paronychia erythrasma, secondary infected dermatoses, carbuncles, furonculosis, ecthyma, cellulitis, erysipelas, necrotising fasciitis, secondary skin infections of wounds, dermatitis, scabies, diabetic ulcer and acne.

34. The composition for the use of any of clause 33, wherein the infection or disease is acne.

35. The composition for the use of clause 34, wherein the acne is non-inflammatory acne.

36. The composition for the use of clause 34, wherein the acne is inflammatory acne.

37. The composition for the use of any of clauses 34 to 36, wherein the acne is severe acne.

38. The composition for the use of any of clauses 34 to 37, wherein the acne is mild or moderate acne.

39. The composition for the use according to any of clauses 34 to 38, wherein the Gram-positive bacteria is *Propionibacterium acnes*.

40. The composition for the use of any of clauses 28 to 39, wherein the Gram-positive bacteria is not an antibiotic resistant strain.

41. The composition for the use of any of clauses 28 to 39, wherein the Gram-positive bacteria is an antibiotic resistant strain.

42. The composition for the use of clause 41, wherein the Gram-positive bacteria is an antibiotic strain resistant to a drug selected from fusidic acid, mupirocin, retapamulin, erythromycin, clindamycin and a tetracycline.

43. The composition for the use of clause 42, wherein the Gram-positive bacteria is resistant to a drug selected from fusidic acid, mupirocin and retapamulin.

44. The composition for the use of clause 42, wherein the Gram-positive bacteria is resistant to a drug selected from erythromycin and clindamycin.

45. The composition for the use of clause 42, wherein the Gram-positive bacteria is resistant to a drug selected a tetracycline, for example tetracycline, minocycline or doxycycline.

46. The composition for the use of clause 41, wherein the Gram-positive bacteria is a *propionibacterium* Spp which is resistant to a drug selected from erythromycin and clindamycin.

47. The composition for the use of clause 41, wherein the Gram-positive bacteria is bacteria is methicillin-resistant *Staphylococcus aureus*.

48. The composition for the use according to any one of clauses 28 to 47, wherein the infection or disease is in a human or animal, for example wherein the infection is in a human.

49. The composition for the use according to any of clauses 28 to 48, wherein the composition is administered topically as a maintenance therapy.

50. The composition for the use according to any of clauses 28 to 49, wherein the composition is administered as a monotherapy for the prevention or treatment of the infection or disease.

51. The composition for the use according to any of clauses 34 to 39 or clause 46, wherein the composition is used in combination with benzoyl peroxide and/or a retinoid.

52. The composition for the use according to any of clauses 28 to 51, wherein the composition is administered topically for less than 2 weeks, for example 1 day or 1 week.

53. The composition for the use according to any of clauses 28 to 51, wherein the composition is administered topically for a period selected from more than 2 weeks, more than 3 weeks, more than 4 weeks, more than 6 weeks, more than 12 weeks, more than 6 months and more than 1 year.

54. The composition for the use according to any of clauses 28 to 53, wherein the treatment is administered topically once or twice per day.

55. A method of treating or preventing a disease or infection caused by Gram-positive bacteria in a subject, the method comprising topically administering to the subject a therapeutically effective amount of the composition of any of clauses 1 to 27.

56. The method of clause 55, wherein the Gram-positive bacteria is resistant to a drug selected from fusidic acid, mupirocin, retapamulin, erythromycin and clindamycin.

57. The method of clause 55, wherein the Gram-positive bacteria is methicillin-resistant *Staphylococcus aureus* (MRSA).

58. The method of clause 55, wherein the Gram-positive bacteria is not a *propionibacterium*.

59. The method of clause 55 to 58, wherein the Gram-positive bacteria develops spontaneous mutations which confer resistance to the halogenated salicylanilide at a frequency of less than $10^{-6}$ at the MIC of the halogenated salicylanilide to the Gram-positive bacteria.

60. The method of 58, wherein the Gram-positive bacteria develops spontaneous mutations which confer resistance to the halogenated salicylanilide at a frequency of less than $10^{-9}$ at the MIC of the halogenated salicylanilide to the Gram-positive bacteria.

61. The method of any of clauses 55 to 60, wherein the Gram-positive bacteria is selected from *Staphylococcus* spp. or *Streptococcus* spp.

62. The method of any of clauses 55 to 61, wherein the infection or disease is selected from the group consisting of impetigo, infected eczema, rosacea, bacterial conjunctivitis, atopic dermatitis and related infections, sycosis barbae, superficial folliculitis, paronychia erythrasma, secondary infected dermatoses, carbuncles, furonculosis, ecthyma, cellulitis, erysipelas, necrotising fasciitis, secondary skin infections of wounds, dermatitis, scabies, diabetic ulcers and acne.

63. The method of clause 62, wherein the infection or disease is selected from the group consisting of impetigo, infected eczema, rosacea, bacterial conjunctivitis and atopic dermatitis.

64. The method of clause 62, wherein the infection or disease is acne.

65. The method of any of clauses 55 to 64, wherein the formulation is administered topically for a period selected from more than more than 2 weeks, 3 weeks, more than 4 weeks, more than 6 weeks, more than 12 weeks, more than 6 months and more than 1 year.

66. The method of any of clauses 55 to 64, wherein the formulation is administered topically for a period of less than 2 weeks.

67. The method of any of clauses 55 to 66, wherein the treatment is administered topically once or twice per day.

68. A non-aqueous gel composition obtainable by a process gel-forming agent is a carbomer, a particular process for the preparation of the gel composition of the invention comprises:
(i) dissolving the halogenated salicylanilide in a PEG with an average molecular weight of less than 600;
(ii) combining the solution from step (i) with a carbomer to form a mixture; and
(iii) heating the mixture to form a gel.

69. A composition according to any one of clauses 1 to 27 comprising a retinoid and/or benzoyl peroxide.

70. A kit comprising a first and second composition, wherein the first composition comprises a topical composition according to any one of clauses 1 to 27; and the second composition is selected from (i) a composition comprising a retinoid and (ii) a composition comprising benzoyl peroxide.

71. The composition of clause 69 or the kit of clause 70, for use in the topical prevention or treatment of an infection or disease caused by Gram-positive bacteria.

The invention claimed is:

1. A composition comprising:
(i) a halogenated salicylanilide selected from niclosamide, or a pharmaceutically acceptable salt or hydrate thereof;
(ii) greater than 60% of a polyethylene glycol (PEG), wherein the average molecular weight of the PEG is 600 or less; and
(iii) 1% to 5% of a gel forming polymer;
wherein the halogenated salicylanilide is present in an amount of from 2.5% to 8%;
wherein the percent (%) is % by weight of the composition;
wherein the composition does not comprise ethanol or isopropanol; and
wherein the composition is a non-aqueous topical composition.

2. The composition of claim 1, wherein the gel-forming polymer is selected from a thermo-reversible gel-forming polymer and an ionotropic gel-forming polymer.

3. The composition of claim 1, wherein the gel-forming polymer is selected from gelatin; agar; agarose; pectin; carrageenan; chitosan; alginate; starch; starch components; tragacanth gum; xanthan gum; gum arabic; guar gum; gellan gum; locust bean gum; a polyurethane; a polyether polyurethane; cellulose; a cellulose ether; a cellulose ester, a cellulose acetate, a cellulose triacetate; cross-bonded polyvinyl alcohol; a polymer or copolymer of acrylic acid, hydroxyalkyl acrylates, hydroxyethyl acrylate, diethylene glycol monoacrylate, 2-hydroxypropylacrylate or 3-hydroxypropyl acrylate; a carbomer; a polymer or copolymer of methacrylic acid, hydroxyethyl methacrylate, diethyleneglycol monomethacrylate, 2-hydroxypropyl methacrylate, 3-hydroxypropyl methacrylate or dipropylene glycol monomethylacrylate; a vinylpyrrolidone polymer; a polymer or copolymer of acrylamide, N-methylacrylamide, N-propylacrylamide or methacrylamide, N-isopropylmethacrylamide or N-2-hydroxyethylmethacrylamide; a poloxamer; and gels comprising cross-linked polyalkylene glycols and combinations thereof.

4. The composition of claim 1, wherein the gel-forming polymer is a carbomer.

5. The composition of claim 1 wherein the PEG has an average molecular weight of from about 200 to about 600.

6. The composition of claim 1, wherein the PEG is PEG 400.

7. The composition of claim 1 wherein the PEG is present in an amount of from about 70% to about 95% by weight of the composition.

8. The composition of claim 1, wherein the halogenated salicylanilide is niclosamide, or a pharmaceutically acceptable salt thereof.

9. The composition of claim 1, wherein the composition comprises an absorption enhancer.

10. The composition of claim 9, wherein the absorption enhancer is selected from a sulfoxide; dimethylacetamide; dimethylformamide; a urea; a fatty alcohol; a polyol; 1-dodecylazacycloheptan-2-one; an essential oil; a pyrrolidone; an oxazolidinone; a surfactant; and 2-(2-ethoxyethoxy)ethanol.

11. The composition of claim 1, wherein the composition does not comprise a C1-4 alkyl monohydroxy alcohol or benzyl alcohol.

12. The composition of claim 1, wherein the composition does not comprise an alkanolamine.

13. The composition of claim 1, wherein the halogenated salicylanilide is dissolved in the composition.

14. The composition of claim 1, wherein the composition provides a local pH of less than 5.5 at a site of application.

15. A method of treating an infection caused by the Gram-positive bacteria: methicillin-resistant *Staphylococcus aureus* (MRSA) in a subject, the method comprising topically administering to the subject a therapeutically effective amount of the composition of claim 1.

16. The method of claim 15, wherein the Gram-positive bacteria is resistant to a drug selected from fusidic acid, mupirocin, retapamulin, erythromycin and clindamycin.

17. The method of claim 15, wherein the infection caused by the Gram-positive bacteria: methicillin-resistant *Staphylococcus aureus* (MRSA) selected from the group consisting of impetigo, infected eczema, rosacea, bacterial conjunctivitis, atopic dermatitis, sycosis barbae, superficial folliculitis, paronychia erythrasma, secondary infected dermatoses, carbuncles, furonculosis, ecthyma, cellulitis, erysipelas, necrotising fasciitis, secondary skin infections of wounds, dermatitis, scabies, diabetic ulcers and acne.

18. The method of claim 15, wherein the infection caused by the Gram-positive bacteria: methicillin-resistant *Staphylococcus aureus* (MRSA) selected from the group consisting of infected eczema, infected dermatitis, impetigo, infected diabetic ulcers, infected insect bites, infected burns, infected wounds, acne, rosacea, folliculitis, prosthetic joint infections rhinosinusitis, and chronic rhinosinusitis.

19. The method of claim 15, wherein the infection caused by the Gram-positive bacteria: methicillin-resistant *Staphylococcus aureus* (MRSA) selected from the group consisting of impetigo, infected eczema, rosacea, bacterial conjunctivitis and atopic dermatitis.

20. The method of claim 15, wherein the infection or disease is acne.

21. The method of claim 15, wherein the composition is administered topically to the subject for a period selected from more than 2 weeks, more than 3 weeks, more than 4 weeks, more than 6 weeks, more than 12 weeks, more than 6 months and more than 1 year.

22. The method of claim 15, wherein the composition is administered topically to the subject for a period of less than 2 weeks.

23. The method of claim 15, wherein the composition is administered topically to the subject once or twice per day.

24. The composition according to claim 1, further comprising at least one of a retinoid and benzoyl peroxide.

25. The method of claim 15, wherein the infection caused by the Gram-positive bacteria: methicillin-resistant *Staphylococcus aureus* (MRSA) is impetigo.

26. A method of treating atopic dermatitis in a subject, the method comprising topically administering to the subject a therapeutically effective amount of the composition of claim 1.

27. The composition of claim 1, wherein the halogenated salicylanilide is present is an amount of from 2.5% to 6% by weight of the composition.

28. The composition of claim 1, wherein the halogenated salicylanilide is present is an amount of from 3% to 6% by weight of the composition.

29. The composition of claim 1, wherein the halogenated salicylanilide is present is an amount of about 4% by weight of the composition.

30. The composition of claim 4, wherein the carbomer is characterized in that a 0.5% by weight solution of the carbomer in water neutralized to pH 7.3-7.8 has a viscosity of 29400 to 39400 cP when measured at 25° C. using a viscometer, 20 rpm with spindle #6.

* * * * *